United States Patent
Flyckt et al.

(10) Patent No.: US 11,913,035 B2
(45) Date of Patent: *Feb. 27, 2024

(54) MODIFIED SEED OIL CONTENT BY GENE EDITING

(71) Applicant: PIONEER HI-BRED INTERNATIONAL, INC., Johnston, IA (US)

(72) Inventors: Kayla S Flyckt, Ankeny, IA (US); Kristin Haug Collet, Des Moines, IA (US); Zhan-Bin Liu, Clive, IA (US); Keith R Roesler, Urbandale, IA (US); Bo Shen, Johnston, IA (US); Laura L Wayne, Des Moines, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,358

(22) Filed: Sep. 19, 2022

(65) Prior Publication Data
US 2023/0151338 A1 May 18, 2023

Related U.S. Application Data

(63) Continuation of application No. 17/057,056, filed as application No. PCT/US2019/034606 on May 30, 2019, now Pat. No. 11,479,759.

(60) Provisional application No. 62/796,847, filed on Jan. 25, 2019, provisional application No. 62/679,116, filed on Jun. 1, 2018.

(51) Int. Cl.
*C12N 9/10* (2006.01)
*C12N 15/82* (2006.01)

(52) U.S. Cl.
CPC ....... *C12N 9/1029* (2013.01); *C12N 15/8213* (2013.01); *C12N 15/8247* (2013.01); *C12Y 203/0102* (2013.01)

(58) Field of Classification Search
None
See application file for complete search history.

(56) References Cited

U.S. PATENT DOCUMENTS

| 2009/0293152 A1 | 11/2009 | Roesler et al. |
| 2015/0275223 A1 | 10/2015 | Roberts et al. |
| 2016/0348124 A1* | 12/2016 | Roesler ............ C12Y 203/0102 |

FOREIGN PATENT DOCUMENTS

WO 2009/143397 A2 11/2009

OTHER PUBLICATIONS

Caldo, "Diacylglycerol Acyltransferase 1 is Regulated by its N-Terminal Domain in Response to Allosteric Effectors," Plant Physiology, Oct. 2017.
Lam, H. M.; et al.: Diacylglycerol O-acyltransferase 1 [Glycine soja]. Genbank Entry [online]. Dec. 17, 2014 (Dec. 17, 2014), [Retrieved on Aug. 26, 2019]. Retrieved from the Internet: <URL: https://www.ncbi.nlm.nih.gov/protein/KHN06629.1>: p. 1.
Lung, "Diacylglycerol Acyltransferase: A Key Mediator of Plant Triacylglycerol Synthesis," Lipids, 2006, vol. 41, No. 12, pp. 1073-1088.
Luo, "Applications of CRISPR/Cas9 technology for targeted mutagenesis, gene replacement and stacking of genes in higher plants," Plant Cell Reports, 2016.
Roesler, K.; et al.: "An Improved Variant of Soybean Type 1 Diacylglycerol Acyltransferase Increases the Oil Content and Decreases the Soluble Carbohydrate Content of Soybeans", Plant Physiology, Jun. 2016, Epub Apr. 19, 2016 (Apr. 19, 2016), vol. 171, No. 2, pp. 878-893.
International Search Report and Written Opinion for International Application No. PCT/US19/34606, dated Sep. 24, 2019.

* cited by examiner

*Primary Examiner* — Weihua Fan
*Assistant Examiner* — Brian James Sullivan

(57) ABSTRACT

Provided are compositions comprising polynucleotides encoding modified diacylglycerol acyltransferase-1 (DGAT1) polypeptides having improved properties, such as increased enzymatic activity and/or increased stability. Plants, plant cells, seed, grain and comprising the polynucleotides are provided which have one or more of increased fatty acid or protein content. Methods of generating the polynucleotides in plant cells include transformation and genetic modification. Methods of employing the polynucleotides in plants, methods for increasing DGAT1 activity in a plant, and methods for increasing fatty acid content or protein content in a plant are provided.

20 Claims, 13 Drawing Sheets

Figure 1:
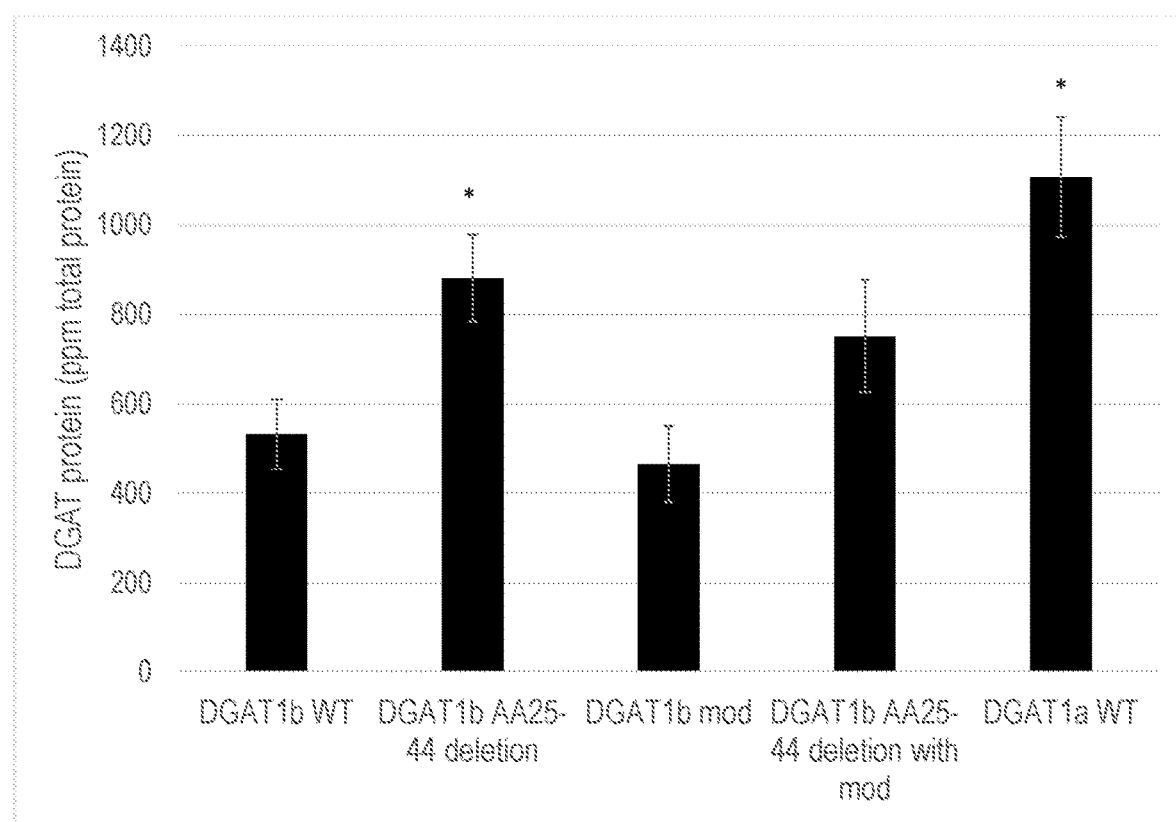

Specification includes a Sequence Listing.

```
              1                                                50
GmDGAT1A   (1) ---------------MAISDEPE---------TVATALNHSSLRRRP-----
GmDGAT1B   (1) ---------------MAISDEPE---------SVATALNHSSLRRRPSA--T
GmGDAT1c   (1) ---------------MAISDVPAAAG-----TTATTTSDSDLRQPSLRRRS
BnDGAT1a   (1) ---------------MAILDSGG-------VAVPPTENGVADLDRLHRRK--
EgDGAT1-1  (1) ---------------MAVSKNPE-----TLAPDQEPSKESDLRRRPASSPS
HvDGAT1    (1) ------------------------------------------MAPPPSV
TaDGAT1    (1) -MSKGNPDPPPPRQLPPFPRRAAHRNPKPRPEPS-GTSPPVPPMAPPPSV
ZmDGAT1-2  (1) ------------------------------------------MAPPPSM
OsDGAT1    (1) MVGSDGDGDGGGGEAHAPAAPAHHHRRPPRPRGGSGAIVEGFAAALRRRI
SbDGAT1b   (1) ----------MADTDDAPPAPAVHRR-PPRPARG-AAAAQGFAAKLRRRL
HaDGAT1    (1) ----MALLDTSDIGDSTAIRGEIRRRSVKPDAG-FGIGDGLYDSSSSSR
GhDGAT1    (1) ---------------MAMFESPEISGSSTATVIGTSRSESDLNHFAPRR-R
Substitution   --------------------------------------------*----

51                                              100
GmDGAT1A  (24) TAAGLFNSP--------ETTTDSSGDDLAKDSG-SDDSISSDAANSQPQQ-
GmDGAT1B  (27) STAGLFNSP--------ETTTDSSGDDLAKDSG-SDDSINSDDAAVNSQQQ
GmGDAT1c  (32) SAGVLFDAARDSGSDNSLTGKITDDDNIKDHKPNNHAASDDNVGAAANDA
BnDGAT1a  (29) SSS---DSSNG---LLSDTSPSDDVGAAAAERDRVDSAAEEEAQGTANLA
EgDGAT1-1 (32) STAASPAVPDSSSRTSSSITGSWTTALDGDSGAGAVRIGDPKDRIGEAND
HvDGAT1    (8) AAAHDCDDP---------SLRLRRADG---------GSSGVHGEARPQE-
TaDGAT1   (49) AAAHDRDDP---------SLRLRRAP----------AADGVHGEAEPQE-
ZmDGAT1-2  (8) PAASDRAGPGRDA-GDSSSLRLRRAPSADAGDLAGDSSGGLRENGEPQSP
OsDGAT1   (51) RSGAAAAARASFG-GDSGDEAASGEPSSSSSSSPSRRRGGDSNGAEASSA
SbDGAT1b  (39) SSGAAAAARASFA-ADSGDESGPGEPSS------SRRR---DNGGDASSA
HaDGAT1   (46) TNSSEEEGE---------SLTNGFDENER------IRAGDETQTTQENKQ
GhDGAT1   (36) AVNNAVDAG-----TRVVERNNSGNGETVDARDRMESANFSRENVNENP-
Substitution   --------*-----------------------------*-----------

101                                             150
GmDGAT1A  (65) -----KQDTDFSVLKFAYRPSVPAHRKVKESPLSSDTIFRQSHAGLFNLC
GmDGAT1B  (69) N---EKQDTDFSVLKFAYRPSVPAHRKVKESPLSSDTIFRQSHAGLFNLC
GmGDAT1c  (82) G---QEHRQPVADFKYAYRPSVPAHRRIKESPLSSDNIFRQSHAGLFNLC
BnDGAT1a  (73) GGDAETRESAGGDVRFTYRPSVPAHRRTRESPLSSDAIFKQSHAGLFNLC
EgDGAT1-1 (82) IGEKKKACSGEVPVGFVDRPSAPVHVRVVESPLSSDTIFQQSHAGLLNLC
HvDGAT1   (39) -------QPQRQHEMPCYRASAPAHRRVKESPLSSDAIFRQSHAGLLNLC
TaDGAT1   (79) -------QPQRQHEMPCYRASAPAHRRVKESPLSSDAIFRQSHAGLLNLC
ZmDGAT1-2 (57) TNP--PPQEQQQHEMLYYRASAPAHRRVKESPLSSDAIFRQSHAGLLNLC
OsDGAT1  (100) AGGGGGRGGGGDFSAFTFRAAAPVHRKAKESPLSSDAIFKQSHAGLFNLC
SbDGAT1b  (79) ADG--GRGGAGDFSAFTFRAAAPVHRKAKESPLSSDAIFKQSHAGLFNLC
HaDGAT1   (81) KTD--QRRDKTSLLQYAYRASSPAHRRIKESPLSSDAIFKQSHAGLFNLC
GhDGAT1   (80) ---------TNSDTRFTYRPSVPAHWRIKESPLSSDNIFQQSHAGLFNLC
Substitution   --------------------------------------------------
```

FIG. 4A

```
              151                                                  200
GmDGAT1A  (110) IVVLVAVNSRLIIENLMKYGWLIKSGFWFSSKSLRDWPLFMCCLSLVVFP
GmDGAT1B  (116) IVVLVAVNSRLIIENLMKYGWLIKSGFWFSSKSLRDWPLFMCCLSLVVFP
GmGDAT1c  (129) IVVLVAVNSRLIIENLMKYGWLIKYGFWFSSKSLRDWPLFMCCLSLAIFP
BnDGAT1a  (123) VVVLVAVNSRLIIENLMKYGWLIRTDFWFSSTSLRDWPLFMCCLSLSVFP
EgDGAT1-1 (132) VVVLIAVNSRLIIENLMKYGLLIGSGFFFSSRLLRDWPLLICSLTLPVFP
HvDGAT1   (82)  IVVLIAVNSRLIIENLMKYGLLIRAGFWFSARSLGDWPLLMCCLTLPIFP
TaDGAT1   (122) IVVLIAVNSRLIIENLMKYGLLIRAGFWFSARSLGDWPLLMCCLTLPIFP
ZmDGAT1-2 (105) IVVLIAVNSRLIIENLMKYGLLIRAGFWFSARSLGDWPLLMCCLTLPVFP
OsDGAT1   (150) IVVLVAVNSRLIIENLMKYGLLIRAGFWFNDKSLRDWPLLMCCLSLPAFP
SbDGAT1b  (127) IVVLVAVNSRLIIENLMKYGLLIRSGFWFNATSLRDWPLLMCCLSLPVFP
HaDGAT1   (129) IVVLVAVNGRLIIENLMKYGLLINSNFWFSSRSLRDWPLLMCCVSLLFFP
GhDGAT1   (121) VVVLVAVNSRLIIENLMKYGWLIRTGFWFSSRSLRDWPLFMCCLSLPIFP
Substitution    --------------------------------------------------

201                                                  250
GmDGAT1A  (160) FAAFIVEKLAQQKCIPEPVVVVLHIIITSASLFYPVLVILRCDSAFLSGV
GmDGAT1B  (166) FAAFIVEKLAQRKCIPEPVVVVLHIIITSTSLFYPVLVILRCDSAFVSGV
GmGDAT1c  (179) LAAFVVERLAQQKCISEPVVVLHLIISTVELCYPVLVILRCDSAFVSGV
BnDGAT1a  (173) LAAFTVEKMVLQKFISEPVAIILHVIITMTEVLYPVYVTLRCDSAFLSGV
EgDGAT1-1 (182) LGSYMVEKLAYKKFISEPVVVSLHVILIIATIMYPVFVILRCDSPILSGI
HvDGAT1   (132) LAALMTEKWAQRKLIRDHVSILLHIIITATVLIYPVVVILKCESAVLSGF
TaDGAT1   (172) LAALMTEKWAQRKLIRDHVSILLHIIITTTVLIYPVVVILKCESAVLSGF
ZmDGAT1-2 (155) LVALMAEKLITRKLIGEHVVILLHIIITTSAIVYPVVVTLKCDSAVLSGF
OsDGAT1   (200) LGAFAVEKLAFNNVITDAVATCLHIFLSTTEIVYPVLVILKCDSAVLSGF
SbDGAT1b  (177) LGAFAVEKLAFNNLITDAAATCFHIFLTTLEIVYPVLVILKCDSAVLSGF
HaDGAT1   (179) LAAYIVEKLAWKKRISDPVVITLHVIVTTTAILYPVFMILRVDSVVLSGV
GhDGAT1   (171) IAAFVVEKLLQQNQISERTLILLHILISTLAVLYPVVVILRCDSAFLSGI
Substitution    ----------------*-------------------------*-----

251                                                  300
GmDGAT1A  (210) TLMLFACVVWLKLVSYAHTNYDMRALTKSVEKGEALPDTLNMDYPYNVSF
GmDGAT1B  (216) TLMLFSCVVWLKLVSYAHTNYDMRALTKLVEKGEALLDTLNMDYPYNVSF
GmGDAT1c  (229) TLMLLTCIVWLKLVSYAHTNYDMRALTVSNEKGETLPNTLIMEYPYTVTF
BnDGAT1a  (223) TLMLLTCIVWLKLVSYAHTSYDIRTLANSADKVDP-------EISYYVSL
EgDGAT1-1 (232) NLMLFVSSICLKLVSYAHANYDLRSSSNSIDKGIHK--------SQGVSF
HvDGAT1   (182) VLMFIASITWLKLVSFAHTNHDIRVLSQSIEKGATHGSSIDEETIKGPTT
TaDGAT1   (222) VLMFIASITWLKLVSFAHTNYDIRVLSQSIEKGATHGSSIDEENIKGPTI
ZmDGAT1-2 (205) VLMFLASIMWMKLVSYAHTNYDIRVLSKSTEKGAAYGNYVDPENMKDPTF
OsDGAT1   (250) LLIFIACIVWLKLVSFAHTNHDIRQLTMGGKKVDNELSTVDMDNLQPPTL
SbDGAT1b  (227) VLMFIACIVWLKLVSFAHTNHDIRKLITSGKKVDNELTVADIDNLQAPTL
HaDGAT1   (229) SLMLCACINWLKLTSFVHTSYDMRSLVNSTDKGETESESLDIELFYDADF
GhDGAT1   (221) ALMLFACIVWLKLVSYAHTNSDMRSVAKSTEKG-------SEGCMYNVSF
Substitution    *-----------------------*---------------*------*-
```

FIG. 4B

```
                        301                                               350
GmDGAT1A    (260) KSLAYFLVAPTLCYQPSYPRTPYIRKGWLFRQLVKLIIFTGVMGFIIEQY
GmDGAT1B    (266) KSLAYFLVAPTLCYQPSYPRTPYIRKGWLFRQLVKLIIFTGVMGFIIEQY
GmGDAT1c    (279) RSLAYFMVAPTLCYQTSYPRTPSVRKGWVFRQLVKLIIFTGVMGFIIEQY
BnDGAT1a    (266) KSLAYFMVAPTLCYQPSYPRSPCIRKGWVARQLAKLVIFTGLMGFIIEQY
EgDGAT1-1   (274) KSLVYFIMAPTLCYQPSYPRTTCIRKGWVICQLVKLVIFTGVMGFIIEQY
HvDGAT1     (232) NSVVYFMLAPTLCYQPSYPRTAFVRKGWVAQQLIKCIVFTGLMGFIIEQY
TaDGAT1     (272) NSVVYFMLAPTLCYQPSYPRTAFTRKGWVTRQLIKCVVFTGLMGFIIEQY
ZmDGAT1-2   (255) KSLVYFMLAPTLCYQPTYPQTTCIRKGWVTQQLIKCVVFTGLMGFIIEQY
OsDGAT1     (300) GNLIYFMMAPTLCYQPSYPRTSCVRKGWLIRQIILYLIFTGLQGFIIEQY
SbDGAT1b    (277) GSLTYFMMAPTLCYQPSYPRTPYVRKGWLVRQVILYLIFTGLQGFIIEQY
HaDGAT1     (279) KSLVYFLLAPTLCYQLRYPRTAFIRKGWVLRQLIKLIIFTGLMGFIIEQY
GhDGAT1     (264) RSLAYFMAAPTLCYQTSYPRTASIRKNWVVRQFIKLIIFTGLMGFIIEQY
Substitution      --------------------------------------------------

351                                               400
GmDGAT1A    (310) INPIVQNSQHPLKGNLLYAIERVLKLSVPNLYVWLCMFYCFFHLWLNILA
GmDGAT1B    (316) INPIVQNSQHPLKGNLLYATERVLKLSVPNLYVWLCMFYCFFHLWLNILA
GmGDAT1c    (329) MNPIVQNSTHPLKGNLLYAIERILKLSVPNVYVWLCMFYCFFHLWLNILA
BnDGAT1a    (316) INPIVRNSKHPLKGDLLYAIERVLKLSVPNLYVWLCMFYCFFHLWLNILA
EgDGAT1-1   (324) IDPIIKNSQHPLKGNVLNAMERVLKLSIPTLYVWLCVFYCTFHLWLNILA
HvDGAT1     (282) INPIVQNSKHPLKGNFLDAIERVLKLSVPTLYVWLCMFYCFFHLWLNILA
TaDGAT1     (322) INPIVQNSKHPLKGNFLDAIERVLKLSVPTLYVWLCMFYSFFHLWLNILA
ZmDGAT1-2   (305) INPIVKNSKHPLKGNFLNAIERVLKLSVPTLYVWLCMFYCFFHLWLNIVA
OsDGAT1     (350) INPIVVNSQHPLKGGLLNAVETVLKLSLPNVYLWLCMFYAFFHLWLSILA
SbDGAT1b    (327) INPIVVNSQHPLKGGLLNAVETVLKLSLPNVYLWLCMFYCLFHLWLNILA
HaDGAT1     (329) INPIVQNSQHPLNGDILYAIERVLKLSVPNLYVWLCMFYCFFHLWLNILA
GhDGAT1     (314) INPIVQNSQHPLKANFLYAIERILKLSVPNTYVWLCMFYSFFHLWLNILA
Substitution      -------------*-------------------------*--------*-

401                                               450
GmDGAT1A    (360) ELLRFGDREFYQDWWNAKTVEDYWRMWNMPVHKWMIRHLYFPCLRHGIPK
GmDGAT1B    (366) ELLRFGDREFYKDWWNAKTVEDYWRMWNMPVHKWMIRHLYFPCLRHGLPK
GmGDAT1c    (379) ELVRFGDREFYKDWWNAKTVEEYWRMWNMPVHKWMVRHIYFPCLRRGIPK
BnDGAT1a    (366) ELLCFGDREFYKDWWNAKSVGDYWRMWNMPVHKWMVRHVYFPCLRIKIPK
EgDGAT1-1   (374) ELLCFGDREFYKDWWNAKTIEEYWRMWNMPVHKWMLRHVYLPCIRNGIPK
HvDGAT1     (332) ELLRFGDREFYKDWWNARTVEEYWRMWNMPVHKWIVRHIYFPCIRNGLSK
TaDGAT1     (372) ELLRFGDREFYKDWWNAKTVEEYWRMWNMPVHKWIVRHIYFPCIRNGLSK
ZmDGAT1-2   (355) ELLCFGDREFYKDWWNAKTVEEYWRMWNMPVHKWIIRHIYFPCIRKGFSR
OsDGAT1     (400) EILRFGDREFYKDWWNAKTIDEYWRKWNMPVHKWVVRHIYFPCMRNGISK
SbDGAT1b    (377) EILRFGDREFYKDWWNAKTIDEYWRKWNMPVHKWMLRHIYFPCIRNGISK
HaDGAT1     (379) ELLRFGDREFYKDWWNAQTIEEYWRLWNMPVHKWIVRHLYFPCLRNGIPK
GhDGAT1     (364) ELLRFGDREFYKDWWNAKTVEEYWRMWNMPVHKWMVRHIYLPCLRNGIPK
Substitution      --------------------*-----------------------------

FIG. 4C
```

```
             451                                                        500
GmDGAT1A  (410) AVALLIAFLVSALFHELCIAVPCHIFKLWAFGGIMFQVPLVFITNYLQNK
GmDGAT1B  (416) AAALLIAFLVSALFHELCIAVPCHIFKLWAFGGIMFQVPLVLITNYLQNK
GmGDAT1c  (429) GAASLIAFLVSAVFHELCIAVPCHMFKLWAFIGIMFQVPLVLITNYLQNK
BnDGAT1a  (416) VPAIIIAFLVSAVFHELCIAVPCRLFNLWAFMGIMFQVPLVFITNFLQER
EgDGAT1-1 (424) GVAMVISFFISAIFHELCIGIPCHIFKFWAFIGIMFQVPLVILTKYLQNK
HvDGAT1   (382) GCAILISFLVSAVFHELCIAVPCHIFKLWAFSGIMFQIPLLFLTKYLQDK
TaDGAT1   (422) GCAILIAFLVSAVFHELCIAVPCHIFKLWAFSGIMFQIPLLFLTKYLQEK
ZmDGAT1-2 (405) GVAILISFLVSAVFHEICIAVPCHIFKFWAFSGIMFQIPLVFLTRYLHAT
OsDGAT1   (450) EVAVLISFLVSAVLHEICVAVPCRILKFWAFLGIMLQIPLIVLTAYLKSK
SbDGAT1b  (427) EVAAFIAFFVSAVFHELCVAVPCHILKFWAFLGIMLQIPLIILTSYLKNK
HaDGAT1   (429) GAAILVAFFMSAVFHELCIAVPCHIFKFWAFIGIMFQVPLVLLTNYLQNK
GhDGAT1   (414) GVAILIAFLVSAIFHELCIAVPCHLFKLWAFFGIMFQAPLVLITSYLQNK
Substitution    ------------------------*-------------------------

501                            541
GmDGAT1A  (460)FRNSMVGNMIFWFIFSILGQPMCVLLYYHDLMNRKGKLD--(SEQ ID NO: 4)
GmDGAT1B  (466)FRNSMVGNMIFWFIFSILGQPMCVLLYYHDLMNRKGKLD--(SEQ ID NO: 2)
GmGDAT1c  (479)YRNSMVGNMIFWFIFCILGQPMSVLLYYHDLMNRKGEVD--(SEQ ID NO: 6)
BnDGAT1a  (466)FG-SMVGNMIFGSASCIFGQPMCGLLYYHDLMNRKGSMS--(SEQ ID NO: 8)
EgDGAT1-1 (474)FKSAMVGNMIFWFFFSIYGQPMCVLLYYHDVMNRKVGTE--(SEQ ID NO: 24)
HvDGAT1   (432)FKNTMAGNMIFWFFFSIVGQPMCVLLYYHDVMNRQAQTNG-(SEQ ID NO: 14)
TaDGAT1   (472)FKNTMVGNMIFWFFFSIVGQPMCVLLYYHDVMNRQAQTNG-(SEQ ID NO: 20)
ZmDGAT1-2 (455)FKHVMVGNMIFWFFFSIVGQPMCVLLYYHDVMNRQAQASR-(SEQ ID NO: 22)
OsDGAT1   (500)FRDTMVGNMIFWFFFCIYGQPMCLLLYYHDVMNRIEKAR--(SEQ ID NO: 16)
SbDGAT1b  (477)FNDTMVGNMIFWFFFCIYGQPMCVLLYYHDVMNRTEKTK--(SEQ ID NO: 18)
HaDGAT1   (479)FQNSMVGNIIFWCFFSILGQPMCVLLYYHDVMNQKVNSK--(SEQ ID NO: 12)
GhDGAT1   (464)FQSSMVGNMIFWFIFCILGQPTCVLLYYHDLMNRKGSAD--(SEQ ID NO: 10)
```

FIG. 4D

SEQUENCE LISTING

```
Sequence total quantity: 42
SEQ ID NO: 1            moltype = DNA  length = 1515
FEATURE                 Location/Qualifiers
source                  1..1515
                        mol_type = genomic DNA
                        organism = Glycine max
SEQUENCE: 1
atggcgattt ccgatgagcc tgaaagtgta gccactgctc tcaaccactc ttccctgcgc   60
cgccgtccct ccgccacctc caccgccggc ctcttcaatt cgcctgagac aaccaccgac  120
agttccggtg atgacttggc caaggattct ggttccgacg actccatcaa cagcgacgac  180
gccgccgtca attcccaaca gcaaaacgaa aaacaagaca ctgatttctc cgtcctcaaa  240
ttcgcctacc gtccttccgt ccccgctcac cgcaaagtga aggaaagtcc gctcagctcc  300
```

```
gacactattt tccgtcagag tcacgcgggc ctcttcaacc tttgtatagt agtccttgtt    360
gctgtgaata gccgactcat cattgagaat ttaatgaagt atggttggtt gatcaaatct    420
ggcttttggt ttagttcaaa gtcattgaga gactggcccc ttttcatgtg ttgtctttct    480
cttgtggtat ttcctttcgc tgcctttata gtggagaagt tggcacaacg gaagtgtata    540
cccgaaccag ttgttgttgt acttcatata atcattacct caacttcgct tttctatcca    600
gttttagtta ttctcaggtg tgattctgct tttgtatcag gtgtcacgtt aatgctgttt    660
tcttgtgttg tatggttaaa attggtgtct tatgcacata caaactatga tatgagagca    720
cttaccaaat tagttgaaaa gggagaagca ctgctcgata ctctgaacat ggactatcct    780
tacaacgtaa gcttcaagag cttggcatat ttcctggttg cccctacatt atgttaccag    840
ccaagctatc ctcgcacacc ttatattcga aggggttggt tgtttcgcca acttgtcaag    900
ctgataatat ttacaggagt tatgggattt ataatagaac aatatattaa tcccatagta    960
caaaattcac agcatcctct caagggaaac cttctttacg ccaccgagag agttctgaag   1020
cttctctgtt caaatttata tgtgtggctc tgcatgttct attgcttttt ccacctttgg   1080
ttaaatatcc tggcagagct tcttcgattt ggtgatcgtg aattctacaa ggattggtgg   1140
aatgccaaaa ctgtcgaaga ttattggagg atgtggaata tgcctgttca caaatggatg   1200
atccgccacc tatattttcc atgtttaagg cacggtctac caaaggctgc tgctctttta   1260
attgccttcc tggtttctgc tttattccat gagctgtgca ttgctgttcc ttgccacata   1320
ttcaagttgt gggtttcgg tggaattatg tttcaggttc ctttggtctt gatcactaat   1380
tatctgcaaa ataaattcag aaactcaatg gttggaaata tgattttttg gttcatattc   1440
agtatccttg gtcaacctat gtgtgtactg ctatactacc atgactttgat gaataggaaa   1500
ggcaaacttg actga                                                    1515

SEQ ID NO: 2         moltype = AA  length = 504
FEATURE              Location/Qualifiers
source               1..504
                     mol_type = protein
                     organism = Glycine max
SEQUENCE: 2
MAISDEPESV ATALNHSSLR RRPSATSTAG LFNSPETTTD SSGDDLAKDS GSDDSINSDD    60
AAVNSQQQNE KQDTDFSVLK FAYRPSVPAH RKVKESPLSS DTIFRQSHAG LFNLCIVVLV   120
AVNSRLIIEN LMKYGWLIKS GFWFSSKSLR DWPLFMCCLS LVVFPFAAFI VEKLAQRKCI   180
PEPVVVVLHI IITSTSLFYP VLVILRCDSA FVSGVTLMLF SCVVWLKLVS YAHTNYDMRA   240
LTKLVEKGEA LLDTLNMDYP YNVSFKSLAY FLVAPTLCYQ PSYPRTPYIR KGWLFRQLVK   300
LIIFTGVMGF IIEQYINPIV QNSQHPLKGN LLYATERVLK LSVPNLYVWL CMFYCFFHLW   360
LNILAELLRF GDREFYKDWW NAKTVEDYWR MWNMPVHKWM IRHLYFPCLR HGLPKAAALL   420
IAFLVSALFH ELCIAVPCHI FKLWAFGGIM FQVPLVLITN YLQNKFRNSM VGNMIFWFIF   480
SILGQPMCVL LYYHDLMNRK GKLD                                          504

SEQ ID NO: 3         moltype = DNA  length = 1497
FEATURE              Location/Qualifiers
source               1..1497
                     mol_type = genomic DNA
                     organism = Glycine max
SEQUENCE: 3
atggcgattt ccgatgagcc tgaaactgta gccactgctc tcaaccactc tttccctgcgc    60
cgccgtccca ccgccgctgg cctcttcaat tcgcccgaga cgaccaccga cagttccggt   120
gatgacttgg ccaaggattc cggttccgac gactccatca gcagcgacgc cgccaattgc   180
caaccgcaac aaaaacaaga cactgatttc tccgtcctca aattcgccta ccgtccttcc   240
gtccccgctc atcgcaaagt gaaggaaagt ccgtcagct ccgacaccat tttccgtcag   300
agtcacgcgg gcctcttcaa cctctgtata gtagtccttg ttgctgtgaa tagccgactc   360
atcattgaga atttaatgaa gtatggttgg ttgatcaaat ctggcttttg gttttagtca   420
aagtcattga gagactggcc cctcttcatg tgttgtcttt ctcttgtggt atttcctttt   480
gctgcattta gtggagaa gttggcacag cagaagtgta tacccgaacc agttgttgtt   540
gtacttcata taatcattac ctcagcttca cttttctatc cagttttagt aattctcagg   600
tgtgattctg cttttgtatc aggtgttacg ttaatgctat ttgcttgtgt tgtatggtta   660
aaattggtgt cttatgcaca tacaaactat gatatgagag cacttaccaa atcagttgaa   720
aagggagaag ctctgccgga tactctgaac atggactatc cttacaatgt aagcttcaag   780
agcttagcat atttcctggt tgcccctaca ttatgttacc agccaagcta tcctcgcaca   840
ccttatattc gaaagggttg gctgtttcgc caacttgtca agcttgataat attacagga   900
gttatggaga ttataataga acaatacatt aatcccattg tacaaaattc acagcatcct   960
ctcaagggaa accttcttta cgccatcgag agagttctga agcttctgt tccaaattta   1020
tatgtgtggc tctgcatgtt ctattgcttt ttccaccttt ggttaaatat attggcagag   1080
cttcttcgat ttggtgatcg tgaattctac aggattggt ggaatgccaa actgttgaa   1140
gattattgga ggatgtggaa tatgcctgtt cacaaatgga tgatccgcca cctatatttt   1200
ccatgtttaa ggcacggtat accaaaggc gttgctcttt taattgcctt cctggtttct   1260
gctttattcc atgagctgtg catcgctgtt ccttgccaca tattcaagtt gtgggctttc   1320
ggtggaatta tgtttcaggt tcctttggtc ttcatcacta attatctgca aaataaattc   1380
agaaactcga tggtggaaa tatgattttt tggttcatat tcagtattct ggtcaacct   1440
atgtgcgtac tgctatatta ccatgactta atgaatagga aggcaaact tgactga      1497

SEQ ID NO: 4         moltype = AA  length = 498
FEATURE              Location/Qualifiers
source               1..498
                     mol_type = protein
                     organism = Glycine max
SEQUENCE: 4
MAISDEPETV ATALNHSSLR RRPTAAGLFN SPETTTDSSG DDLAKDSGSD DSISSDAANS    60
QPQQKQDTDF SVLKFAYRPS VPAHRKVKES PLSSDTIFRQ SHAGLFNLCI VVLVAVNSRL   120
IIENLMKYGW LIKSGFWFSS KSLRDWPLFM CCLSLVVFPF AAFIVEKLAQ QKCIPEPVVV   180
```

```
VLHIIITSAS LFYPVLVILR CDSAFLSGVT LMLFACVVWL KLVSYAHTNY DMRALTKSVE        240
KGEALPDTLN MDYPYNVSFK SLAYFLVAPT LCYQPSYPRT PYIRKGWLFR QLVKLIIFTG        300
VMGFIIEQYI NPIVQNSQHP LKGNLLYAIE RVLKLSVPNL YVWLCMFYCF PHLWLNILAE        360
LLRFGDREFY QDWWNAKTVE DYWRMWNMPV HKWMIRHLYF PCLRHGIPKA VALLIAFLVS        420
ALFHELCIAV PCHIFKLWAF GGIMFQVPLV FITNYLQNKF RNSMVGNMIF WFIFSILGQP        480
MCVLLYYHDL MNRKGKLD                                                      498

SEQ ID NO: 5              moltype = DNA   length = 1554
FEATURE                   Location/Qualifiers
source                    1..1554
                          mol_type = genomic DNA
                          organism = Glycine max
SEQUENCE: 5
atggcgatct ccgatgtgcc tgcagccgct ggcacgaccg ccactaccac cagcgactca         60
gatctccgac agccttctct gcggcgcagg tcctccgccg gagtcctctt cgacgctgcc        120
agagattccg gctccgacaa ttccctgacc ggcaaaatca ccgacgacga caacatcaaa        180
gatcacaagc cgaataatca cgcagcctcc gacgacaatg tgggcgccgc cgccaatgac        240
gctgggcagg agcaccgaca accggtcgcc gatttcaaat acgcttaccg tccctccgtt        300
cccgcgcacc gcagaatcaa ggagagcccc cttagctccg acaacatctt cagacagagt        360
catgcaggac tgttcaatct ctgcatagta gtgcttgttg ccgtgaacag cagacttatc        420
attgagaatt taatgaagta tggttggttg atcaagtatg gcttttggtt tagttcaaaa        480
tcattgagag attggcctct cttcatgtgc tgtcttagtc ttgccatatt tccacttgct        540
gcctttgttg tggaaaggtt ggcacaacaa aagtgtattt ctgaaccagt tgttgttcta        600
cttcatctaa taatatcaac tgttgaactg tgctatccgg ttttagtaat actcaggtgt        660
gattctgctt ttgtatctgg tgtcacgttg atgctattaa cttgcattgt gtggttaaaa        720
ttggtgtcat atgcacatac aaaactatgat atgagagcac ttactgtttc gaatgaaaaa        780
ggagaaacat acccaatac tttgattatg gagtatccgt acactgtgac cttcaggagt        840
ttggcatact tcatggttgc tcctacatta tgctatcaga caagctatcc tcgcacacct        900
tcagttcgaa agggttgggt gtttcgtcaa cttgtcaagc tgataatatt tacaggagtt        960
atgggattta ataagaaca atatatgaat cctattgtac aaaactcaac tcatccttg        1020
aagggaaacc ttctatatgc cattgagaga attctgaagc tttctgtccc aaatgtatat        1080
gtgtggctct gcatgttcta ctgctttttc caccttggt taaatatact tgcagagctt        1140
gttcgatttg gtgatcgtga gttctataaa gattggtgga atgccaaaac tgttgaagag        1200
tattgatgga gtgtggaatat gcctgtgcac aaatggatgg ttcgccacat atattttcca        1260
tgcttaaggc gtggtataacc caagggtgct gcttcattaa ttgcattcct ggttctgct        1320
gtgtttcatg agttatgcat tgccgttcct tgccacatgt tcaagttgtg ggcttttata        1380
ggaattatgt tcaggttcc tttggtcttg atcactaatt acctccaaaa taatacaga        1440
aactcaatgg ttggaaatat gatttttgg ttcatatttt gtattcttgg tcaaccaatg        1500
agcgtactat tgtactacca tgacttgatg aatagaaaag gagaagttga ctaa              1554

SEQ ID NO: 6              moltype = AA    length = 517
FEATURE                   Location/Qualifiers
source                    1..517
                          mol_type = protein
                          organism = Glycine max
SEQUENCE: 6
MAISDVPAAA GTTATTTSDS DLRQPSLRRR SSAGVLFDAA RDSGSDNSLT GKITDDDNIK         60
DHKPNNHAAS DDNVGAAAND AGQEHRQPVA DFKYAYRPSV PAHRRIKESP LSSDNIFRQS        120
HAGLFNLCIV VLVAVNSRLI IENLMKYGWL IKYGFWFSSK SLRDWPLFMC CLSLAIFPLA        180
AFVVERLAQQ KCISEPVVVL LHLIISTVEL CYPVLVILRC DSAFVSGVTL MLLTCIVWLK        240
LVSYAHTNYD MRALTVSNEK GETLPNTLIM EYPYTVTFRS LAYFMVAPTL CYQTSYPRTP        300
SVRKGWVFRQ LVKLIIFTGV MGFIIEQYMN PIVQNSTHPL KGNLLYAIER ILKLSVPNVY        360
VWLCMFYCFF HLWLNILAEL VRFGDREFYK DWWNAKTVEE YWRMWNMPVH KWMVRHIYFP        420
CLRRGIPKGA ASLIAFLVSA VFHELCIAVP CHMFKLWAFI GIMFQVPLVL ITNYLQNKYR        480
NSMVGNMIFW FIFCILGQPM SVLLYYHDLM NRKGEVD                                 517

SEQ ID NO: 7              moltype = DNA   length = 1509
FEATURE                   Location/Qualifiers
source                    1..1509
                          mol_type = genomic DNA
                          organism = Brassica napus
SEQUENCE: 7
atggcggttt ggattctgg aggcgtcgct gtgccgacgg agaacggcgt cgcggatctc          60
gacaggctcc atcgtcgtaa atcgagatcg gattcttcca acggactcct ccccgatact        120
tccccgtcgg acgatgttgg agctgcggcg gccgaaaggg atcggggttga ttccgctgcc        180
gaggaggagg ctcagggaac agcgaattta gctggcggag atgccgaaac tagggaatcc        240
gccgaggcg atgtaaggtt tacgtatcga ccgtcggttc cagctcatcg gaggacgagg        300
gagagtcctc tcagctctga cgctatcttc aaacaaagca atgcaggatt gttcaactcg        360
tgtgtagttg ttcttgttgc tgttaacagt agactcatca tcgaaaacct catgaagtat        420
ggttggttga tcagaactga ttttttggtt agttctacat ccttacgaga ctggccgctt        480
ttcatgtgtt gtctttcact ttcgqtcttt cctttggctg ccttcacggt cgagaaaatg        540
gtacttcaga gattcatatc tgagcctgtt gccatcattc ttcatgttat tataaccttg        600
acagaggtct tgtatccagt ctacgtcaca ctgaggtgtg attctgcctt cttgtcaggt        660
gtcacgttga tgctgctcac ttgcattgtg tggtttctta cgctcatact        720
agctacgaca taagaaccct agctaattca gctgataagg tcgatcctga aatcctctac        780
catgttagct tgaagagctt ggcgtatttc atggttgctc ctacactgtg ttatcagcca        840
agctatccac gttccccatg tatacggaag ggttgggtgg ctcgtcaatt tgcgaaactg        900
gtcatattca ctggactcat gggatttata atagagcagt atataaatcc tattgtaagg        960
aactcaaagc atccgttgaa aggggatctt ctatacgcta ttgaaagagt gttgaagctt       1020
```

```
tcagttccaa atctatatgt gtggctctgc atgttctact gcttcttcca cctttggtta  1080
aacatattgg cagagctgct ctgcttcggg gaccgtgaat tctacaaaga ttggtggaat  1140
gcaaaaagcg ttggagatta ttggagaatg tggaatatgc ctgttcataa atggatggtt  1200
cgacatgtat actttccgtg cctgcgcatc aagataccaa aagtacccgc cattatcatt  1260
gctttcttag tctctgcagt ctttcatgag ttatgcatcg cagttcctg ccgtctcttc  1320
aatctatggg ctttcatggg aattatgttt caggtccctt tggtctttat cacaaacttt  1380
ttacaagaaa ggtttggctc catggtggga aacatgatct tctggttcag cttctgcatt  1440
ttcggacaac ccatgtgtgt tcttctttat taccatgacc tgatgaaccg caaaggatcc  1500
atgtcctga                                                           1509
```

```
SEQ ID NO: 8           moltype = AA   length = 503
FEATURE                Location/Qualifiers
source                 1..503
                       mol_type = protein
                       organism = Brassica napus
SEQUENCE: 8
MAILDSGGVA VPPTENGVAD LDRLHRRKSS SDSSNGLLSD TSPSDDVGAA AAERDRVDSA   60
AEEEAQGTAN LAGGDAETRE SAGGDVRFTY RPSVPAHRRT RESPLSSDAI FKQSHAGLFN  120
LCVVVLVAVN SRLIIENLMK YGWLIRTDFW FSSTSLRDWP LFMCCLSLSV FPLAAFTVEK  180
MVLQKFISEP VAIILHVIIT MTEVLYPVYV TLRCDSAFLS GVTLMLLTCI VWLKLVSYAH  240
TSYDIRTLAN SADKVDPEIS YYVSLKSLAY FMVAPTLCYQ PSYPRSPCIR KGWVARQLAK  300
LVIFTGLMGF IIEQYINPIV RNSKHPLKGD LLYAIERVLK LSVPNLYVWL CMFYCFFHLW  360
LNILAELLCF GDREFYKDWW NAKSVGDYWR MWNMPVHKWM VRHVYFPCLR IKIPKVPAII  420
IAFLVSAVFH ELCIAVPCRL FNLWAFMGIM FQVPLVFITN FLQERFGSMV GNMIFGSASC  480
IFGQPMCGLL YYHDLMNRKG SMS                                          503
```

```
SEQ ID NO: 9           moltype = DNA   length = 1509
FEATURE                Location/Qualifiers
source                 1..1509
                       mol_type = genomic DNA
                       organism = Gossypium hirsutum
SEQUENCE: 9
atggcgatgt ttgagtcacc ggagatttca gggagtagta cggcgacggt gatcggtacc   60
tcacgtagcg agtcagatct taatcatttt gcgcccgtc gtcgagccgt gaataacgca  120
gtcgatgcag ggactagagt tgtggagcgt aacaattccg gtaatggcga gacagtggac  180
gctagggatc gaatgaatc ggctaatttc tcgaggaaa acgtgaatga gaatccgact  240
aattcagata cgaggttcac gtatcggcct tctgttcctg ctcattggag atcaaagaa  300
agccctctca gctctgacaa tatcttccaa cagagtcatg caggcctgtt taacctatgt  360
gttgtagtgc ttgttgctgt aaacagccgg cttattattg agaacctgat gaagtatggga  420
tggttgatca gaactggctt ttggtttagt tcgagatcat tgagggattg gcctcttttt  480
atgtgctgtc tttctctccc aatattccca atcgcggcct tgtagttga aaagttgttg  540
caacagaatc aaatatctga acgaactctt attttacttc atatactgat tagcacgctt  600
gcagttctat atccagttgt tgttattctc aggtgtgatt ctgcattctt atcaggcatt  660
gcattgatgc tatttgcttg cattgtctgg ttaaaattgg tatcctatgc tcatactaac  720
agtgatatga atcagttgc gaagtcgact gaaaagggaa gtgaaggctg catgtacaat  780
gttagcttca ggagtctggc atacttcatg gcagctccca cattatgtta ccagacaagc  840
tatcctcgta ctgcatcaat tagaaaaaat tgggtggttc gtcaattat caagttaata  900
atatttactg gactcatggg tttcataata gaacagtata tcaatccaat tgttcagaac  960
tctcagcacc ctttgaaggc gaacttttta tatgccatag aaagaattt gaagctttca 1020
gttccaaata catatgtctg gctttgcatg ttctacagct tctttcatct ctggttaaat 1080
atactggctg agcttcttcg ttttggggac cgcgagtttt ataaagattg gtggaatgca 1140
aaaactgttg aggagtattg gagaatgtgg aatatgcctg ttcataaatg gatggttcgc 1200
catatctatt tgccatgctt aaggaacggg ataccaaagg gagttgccat tcttatcgcc 1260
ttcttggttt ctgctatatt tcatgagctc tgcattgctg ttccttgcca cttatttaag 1320
ttatgggctt tcttttggcat catgtttcag gctcccttgg tcttgatcac tagttatctt 1380
caaaataagt tccagagttc aatggtggga aatatgatat tctggttcat attctgcatt 1440
cttggtcaac caacgtgcgt actttatat tatcatgatt tgatgaatcg caaggatcg 1500
gcagattaa                                                          1509
```

```
SEQ ID NO: 10          moltype = AA   length = 502
FEATURE                Location/Qualifiers
source                 1..502
                       mol_type = protein
                       organism = Gossypium hirsutum
SEQUENCE: 10
MAMFESPEIS GSSTATVIGT SRSESDLNHF APRRRAVNNA VDAGTRVVER NNSGNGETVD   60
ARDRMESANF SRENVNENPT NSDTRFTYRP SVPAHWRIKE SPLSSDNIFQ QSHAGLFNLC  120
VVVLVAVNSR LIIENLMKYG WLIRTGFWFS SRSLRDWPLF MCCLSLPIFP IAAFVVEKLL  180
QQNQISERTL ILLHILISTL AVLYPVVVIL RCDSAFLSGI ALMLFACIVW LKLVSYAHTN  240
SDMRSVAKST EKGSEGCMYN VSFRSLAYFM AAPTLCYQTS YPRTASIRKN WVVRQFIKLI  300
IFTGLMGFII EQYINPIVQN SQHPLKANFL YAIERILKLS VPNTYVWLCM FYSFFHWLN  360
ILAELLRFGD REFYKDWWNA KTVEEYWRMW NMPVHKWMVR HIYLPCLRNG IPKGVAILIA  420
FLVSAIFHEL CIAVPCHLFK LWAFFGIMFQ APLVLITSYL QNKFQSSMVG NMIFWFIFCI  480
LGQPTCVLLY YHDLMNRKGS AD                                           502
```

```
SEQ ID NO: 11          moltype = DNA   length = 1554
FEATURE                Location/Qualifiers
source                 1..1554
                       mol_type = genomic DNA
```

```
                        organism = Helianthus annuus
SEQUENCE: 11
atggcgttac tagatacgtc agatatcgga gactccaccg ccatacgcgg cgagataaga    60
cggcggagga gcgtgaagcc tgatgccgga ttcggaatcg gagacggttt gtatgattct   120
tcatccgtct tctcgaacga actcgtctga agaagaggtg agagtttgac taacggtttc   180
gatgaaaatg aacggatccg agctggtgat gaaactcaaa caacacagga aaataaacag   240
aagacagatc agagaagaga taaaacgagt ctgttgcaat atgcgtatcg tgcttcttct   300
ccagcgcatc gtagaattaa agagtctccg cttagctccg atgctatctt caagcagagt   360
catgcaggcc tttttaacct tgcatagtg gtgcttgttg ctgtaaatgg taggctcatt    420
attgaaatc tgatgaagta cggattattg atcaattcca attttttggtt cagttcaaga   480
tcattaagag attggcccct tctgatgtgc tgcgtctctc ttctgttctt ccctcttgct   540
gcttacattg ttgagaaatt ggcatggaaa aaacgtatat cagaccctgt tgtaatcact   600
ctccatgtta tagtaactac aactgcgatt ttatatccgg ttttcatgat tctgagggtt   660
gattcagttg ttctatcagg tgtttcattg atgctgtgtg cttgcatcaa ttggttaaaa   720
ttgacatctt ttgtgcatac tagttatgac atgcggtccc ttgtgaattc aaccgataag   780
ggagagacag agtccgagtc tttagatata gagttatttt atgatgctga cttcaaaagc   840
ttggtttatt tcttgcttgc tcctactttg tgttaccagt tacgctatcc ccgcactgca   900
tttattcgaa aggggtgggt gttacggcaa ctgatcaagc taataatatt tacagggtta   960
atgggattca tcattgaaca atatatcaat ccgattgtac aaaactctca gcatccattg  1020
aacggcgaca ttttatacgc aattgaacgt gttttaaagc tttcagttcc aaatttatac  1080
gtttggctct gtatgttcta ctgtttttt cacctttggt tgaatatact tgctgagctt  1140
cttcgttttg gggatcgtga gttttataaa gattggtgga agcacaaac tattgaagag  1200
tattggagac tatggaatat gcctgttcat aaatggattg tacggcatct ctacttccca  1260
tgcttgcgta atgggatacc taagggtgct gccatcttgg ttgcgttttt catgtctgct  1320
gtgttccatg agctttgtat tgctgttccc tgccacatt tcaaatttg ggcttttatt    1380
gggatcatgt ttcaggtgcc cttggtctta ctcacgaatt acttgcagaa caagttccaa   1440
aactcaatgg ttggaaatat aatcttctgg tgcttcttta gcatccttgg tcaacccatg   1500
tgtgtattac tctactatca tgatgtcatg aatcaaaagg tgaatagcaa ataa         1554

SEQ ID NO: 12              moltype = AA  length = 517
FEATURE                    Location/Qualifiers
source                     1..517
                           mol_type = protein
                           organism = Helianthus annuus
SEQUENCE: 12
MALLDTSDIG DSTAIRGEIR RRRSVKPDAG FGIGDGLYDS SSSSRTNSSE EEGESLTNGF    60
DENERIRAGD ETQTTQENKQ KTDQRRDKTS LLQYAYRASS PAHRRIKESP LSSDAIFKQS   120
HAGLFNLCIV VLVAVNGRLI IENLMKYGLL INSNFWFSSR SLRDWPLLMC CVSLLFFPLA   180
AYIVEKLAWK KRISDPVVIT LHVIVTTTAI LYPVFMILRV DSVVLSGVSL MLCACINWLK   240
LTSFVHTSYD MRSLVNSTDK GETESESLDI ELFYDADFKS LVYFLLAPTL CYQLRYPRTA   300
FIRKGWVLRQ LIKLIIFTGL MGFIIEQYIN PIVQNSQHPL NGDILYAIER VLKLSVPNLY   360
VWLCMFYCFF HLWLNILAEL LRFGDREFYK DWWNAQTIEE YWRLWNMPVH KWIVRHLYFP   420
CLRNGIPKGA AILVAFFMSA VFHELCIAVP CHIFKFWAFI GIMFQVPLVL LTNYLQNKFQ   480
NSMVGNIIFW CFFSILGQPM CVLLYYHDVM NQKVNSK                            517

SEQ ID NO: 13              moltype = DNA  length = 1416
FEATURE                    Location/Qualifiers
source                     1..1416
                           mol_type = genomic DNA
                           organism = Hordeum vulgare
SEQUENCE: 13
atggccccgc cccgtccgt ggccgctgcc cacgactgcg acgacccctc cctccgcctc     60
cgccgcgccg acgcggctc ctccggcgtc cacggagagg cgcgtccgca ggagcagccg   120
cagcggcagc acgagatgcc ctgctaccgg gcgtccgcgc ccgcacaccg ccgggtgaag   180
gagagcccgc tcagctccga cgccatcttc cgacagagcc atgcaggtc tctgaatcta   240
tgcattgttg tgctgattgc agtgaacagc aggctcatta tcgagaactt aatgaagtat   300
ggcttattaa taagagctgg attttggttt agtgcaagat cgctgggaga ttggccactt   360
ctgatgtgct gcctaacttt accaatttc ccacttgctg cactcatgac cgagaagtgg    420
gctcaaagaa agctccattc tgatcatgtg tctattcttc tccatatcat tattacagcc   480
actgtcctta tctatccggt tgttgtgatt cttaagtgtg aatcagcagt attatctgga   540
tttgtgttaa tgttcattgc aagcattact tggttgaagc ttgtctcttt tgctcataca   600
aatcatgata taagggtatt gtcccaaagt attgaaaagg tgctacaca tggcagttcc    660
atcgatgaag aaaccattaa aggtccaact accaacagtg ttgtgtattt catgttggcc   720
ccaacactt gttaccagcc aagttatccc cggacagat tgttaggaa aggctgggtg      780
gcccagcagc ttataaatg catagttttt acaggcttga tgggcttcat aattgagcaa   840
tacattaatc caattgtgca gaattccaag catccattga aggaaattt cttggatgct   900
attgagagag tcctgaaact ctcagtgccg acattgtatg tatggctttg tatgttctat   960
tgcttttcc atctgtggtt gaatattctt gccgaactct ccgtttttgg tgatcgtgaa   1020
ttctataagg actggtggaa tgccagaaca gttgaagagt actggagaat gtggaatatg   1080
cctgttcata gtggatcgt tcgacatata tattttccat gcataaggaa tggcttgtca  1140
aagggttgtg ccattctcat ctcatttctt gtttcagctg tatttcatga gctatgtatt  1200
gctgttccgt gccacatttt caaactatgg gcatttctg gaatcatgtt tcagattccc   1260
ctgctattct tgacgaagta tcttcaagat aagttcaaga taacaatggc gggcaacatg   1320
atattttggt tcttcttcag catagttggg cagccaatgt gtgttctctt gtactaccac   1380
gatgtcatga acagacaagc tcagacaaat ggctag                             1416

SEQ ID NO: 14              moltype = AA  length = 471
FEATURE                    Location/Qualifiers
source                     1..471
```

```
                        mol_type = protein
                        organism = Hordeum vulgare
SEQUENCE: 14
MAPPPSVAAA HDCDDPSLRL RRADGGSSGV HGEARPQEQP QRQHEMPCYR ASAPAHRRVK    60
ESPLSSDAIF RQSHAGLLNL CIVVLIAVNS RLIIENLMKY GLLIRAGFWF SARSLGDWPL   120
LMCCLTLPIF PLAALMTEKW AQRKLIRDHV SILLHIIITA TVLIYPVVVI LKCESAVLSG   180
FVLMFIASIT WLKLVSFAHT NHDIRVLSQS IEKGATHGSS IDEETIKGPT TNSVVYFMLA   240
PTLCYQPSYP RTAFVRKGWV AQQLIKCIVF TGLMGFIIEQ YINPIVQNSK HPLKGNFLDA   300
IERVLKLSVP TLYVWLCMFY CFFHLWLNIL AELLRFGDRE FYKDWWNART VEEYWRMWNM   360
PVHKWIVRHI YFPCIRNGLS KGCAILISFL VSAVFHELCI AVPCHIFKLW AFSGIMFQIP   420
LLFLTKYLQD KFKNTMAGNM IFWFFFSIVG QPMCVLLYYH DVMNRQAQTN G           471

SEQ ID NO: 15           moltype = DNA length = 1434
FEATURE                 Location/Qualifiers
source                  1..1434
                        mol_type = genomic DNA
                        organism = Oryza sativa
SEQUENCE: 15
atggccccgc ccccctcgct cgcccccgat cgcggcggcg gcgaacccga cgacgccctc    60
cgcctgcggg cccgcgccgc cgccgccgcc ggtgacgctc ccgctccgca gcagcagcag   120
gagcagaggc atcaggagca gcagcagcag ctgctctggt accgcgcgtc ggcgcccgcc   180
caccgccgcg tcaggagag ccccctcagc tccgacgcca tcttccgcca gagccatgca   240
ggccttctga acctatgcat tgttgtgctg gttgctgtga acagcagact tattattgag   300
aatttaatga agtatggcct actaattaga gctggatttt ggtttagtgg aacatcgctg   360
gcagattggc ctcttctcat gtgctgtctc actttaccaa ctttcccgct tgctgcactt   420
atggttgaga agttggctca aagaaaactt attagtaaac atgtggttat tcttctccat   480
atcgttatta caacatctgt ccttgtctat ccagttgttg tgattctaaa gtgtgattcc   540
gcagtattat ctggatttgt gttgatgttt cttgcaagca ttatttggtt gaagcttgtt   600
tcttttgctc atacaaatta tgatataaga atgctgtcca aaagtattga aaagggcgtg   660
acacatgaca tttctataga tccggagaac attaaatggc caaccttta aaggctatcc   720
tacttcatgt tggccccaac actttgttac cagccaagtt atcccgaac tacatatatt   780
agaaaaggtt gggtggtccg acaactgata aaatgccttg tttttacagg cttgatgggt   840
tttataattg agcaatacat aaatccaatt gtgaagaatt cgaagcatcc attgaaaggg   900
aatttcttga atgctataga gagagtattg aaattatgcc aacattatgt atatctgtg   960
ctttgcatgt tctactgttt tttccatctc tggttgaata ttcttgctga gctcctctgt  1020
tttggtgatc gtgaattcta caaggactgg tggaatgcca aaacagttga agagtattgg  1080
agaatgtgga atatgcctgt tcacaagtgg gtcattcgac atatatattt tccatgcata  1140
aggaatggtt ttctcaaagg gtgttgctatc ctaatctcgt tcctggtttc agctgcattt  1200
catgacgtat cgtgttgctgt tccatgccac atttttaaat tctgggcatt tattgggatc  1260
atgtttcaga ttcccctggt attcttgacg aaataccttc aagataaatt caataacaca  1320
atggtgggca acatgatatt ttggttcttc ttcagcatcc tggggcaacc aatgtgtgtt  1380
ctcttatact accatgatgt catgaacagg caacaagccc aaacaaatag atag         1434

SEQ ID NO: 16           moltype = AA length = 538
FEATURE                 Location/Qualifiers
source                  1..538
                        mol_type = protein
                        organism = Oryza sativa
SEQUENCE: 16
MVGSDGDGDG GGGEAHAPAA PAHHHRRPPR PRGGSGAIVE GFAAALRRRI RSGAAAAARA    60
SFGGDSGDEA ASGEPSSSSS SSPSRRRGGD SNGAEASSAA GGGGRGGSG DFSAFTFRAA   120
APVHRKAKES PLSSDAIFKQ SHAGLFNLCI VVLVAVNSRL IIENLMKYGL LIRAGFWFND   180
KSLRDWPLLM CCLSLPAFPL GAFAVEKLAF NNVITDAVAT CLHIFLSTTE IVYPVLVILK   240
CDSAVLSGFL LIFIACIVWL KLVSFAHTNH DIRQLTMGGK KVDNELSTVD MDNLQPPTLG   300
NLIYFMMAPT LCYQPSYPRT SCVRKGWLIR QIILYLIFTG LQGFIIEQYI NPIVVNSQHP   360
LKGGLLNAVE TVLKLSLPNV YLWLCMFYAF FHLWLSILAE ILRFGDREFY KDWWNAKTID   420
EYWRKWNMPV HKWVVRHIYF PCMRNGISKE VAVLISFLVS AVLHEICVAV PCRILKFWAF   480
LGIMLQIPLI VLTAYLKSKF RDTMVGNMIF WFFFCIYGQP MCLLLYYHDV MNRIEKAR    538

SEQ ID NO: 17           moltype = DNA length = 1473
FEATURE                 Location/Qualifiers
source                  1..1473
                        mol_type = genomic DNA
                        organism = Sorghum bicolor
SEQUENCE: 17
atggccccgc ccccctccat ggccgccgcc tccgatcgcg ccgtcccggg cgccgacgcg    60
accgaggcgt cctccctccg cctcgccgc gccccctcag ccgacgccgg cgaccttgcc   120
gacgattcct caggagaccg gcgggagaac ggcgagccgc aaccgccgca ggagcagcag   180
cagcagcacg agatgctgta ctaccgcgcg tcggccgcca ccgccgcgg cgtcaaggag   240
agcccccctca gctccgacgc catcttccgc cagagccatg ctggtcttct gaatctatgc   300
atcgttgttc tgattgcagt gaacagcaga ctcattattg agaatttaat gaagtatggc   360
ctattgataa gagctggatt tggtttagt gcaagatcgc tgggtgactg gcccttcta   420
atgtgctgcc tcactttacc agttttccca cttgttgccc tcatggctga agctgatt    480
agaagaaagc tcattggtga atatcatggtt attctacatct atcatcattat tacaacatct   540
gtcattgtct atccagttgt tgtgactctt aagtgcgact cagcagtgct atctggattc   600
ttgctaaagt ttcttgcgag catcatgtgg atgaagcttg tctcttatgc acatacaaat   660
tatgatataa gggcattgtc caaaagtact gaaaagggtg ctgcatatgg aaattatgtc   720
gatcctgaga gtatgaaaga tccaaccttt aaaagtctag tgtacttcat gttggcccca   780
acactttgtt accagccaac ttatccccga actacatgta ttaggaaggg ttgggtgacc   840
```

-continued

```
cgacaactta taaagtgcct ggttttttaca ggcttgatgg gcttcataat tgagcaatat    900
ataaacccaa ttgtgaagaa ttccaaacat ccactgaaag ggaatttctt gaatgctata    960
gaaagagtct taaaactctc agtgccaaca ttatatgtat ggctttgcat gttctattgc   1020
ttttttcatt tatggctgaa cattctagct gaactcctct gtttcggtga ccgtgaattc   1080
tacaaggact ggtggaatgc caaaactgtt gaagagtact ggaggatgtg gaacatgcct   1140
gttcataaat ggatcatcag acacatatat tttccatgta taaggaaagg cttttccagg   1200
ggtgtagcta ttctagtctc gtttctggtt tcagctgtat ttcatgagat atgtattgcg   1260
gtgccgtgcc acattttcaa attctgggca ttttctggga tcatgtttca gataccgttg   1320
gtattcttga caagatatct ccaggctacg ttcaagaata taatggtggg caacatgata   1380
ttttggttct tcttcagtat agtcgggcag ccgatgtgtg tccttttata ctaccatgat   1440
gtcatgaaca ggcaggccca ggcaagtaga taa                                1473

SEQ ID NO: 18         moltype = AA  length = 515
FEATURE               Location/Qualifiers
source                1..515
                      mol_type = protein
                      organism = Sorghum bicolor
SEQUENCE: 18
MADTDDAPPA PAVHRRPPRP ARGAAAAQGF AAKLRRRLSS GAAAAARASF AADSGDESGP     60
GEPSSSRRRD NGGDASSAAD GGRGGAGDFS AFTFRAAAPV HRKAKESPLS SDAIFKQSHA    120
GLFNLCIVVL VAVNSRLIIE NLMKYGLLIR SGFWFNATSL RDWPLLMCCL SLPVFPLGAF    180
AVEKLAFNNL ITDAAATCFH IFLTTLEIVY PVLVILKCDS AVLSGFVLMF IACIVWLKLV    240
SFAHTNHDIR KLITSGKKVD NELTVADIDN LQAPTLGSLT YFMMAPTLCY QPSYPRTPYV    300
RKGWLVRQVI LYLIFTGLQG FIIEQYINPI VVNSQHPLKG GLLNAVETVL KLSLPNVYLW    360
LCMFYCLFHL WLNILAEILR FGDREFYKDW WNAKTIDEYW RKWNMPVHKW MLRHIYFPCI    420
RNGISKEVAA FIAFFVSAVF HELCVAVPCH ILKFWAFLGI MLQIPLIILT SYLKNKFNDT    480
MVGNMIFWFF FCIYGQPMCV LLYYHDVMNR TEKTK                              515

SEQ ID NO: 19         moltype = DNA  length = 1536
FEATURE               Location/Qualifiers
source                1..1536
                      mol_type = genomic DNA
                      organism = Triticum aestivum
SEQUENCE: 19
atgtcaaaag ggaacccaga cccgccacct cccggcagc ttcctccctt cccacggcgg      60
gccgccacc gaaacccaaa accccgcccc gaaccttccg gaaccctccc tccagttcca    120
cccatggccc cgccccgtc cgtggccgct gcccacgatc gcgacgaccc ctccctccgc    180
ctccgccgcg ccctgccgc cgacggcgtc cacggagagg cggagccgca ggagcagccg    240
cagccggcagc acgagatgcc ctgctaccgg gcgtcggccg ccgcccaccg ccgggtcaag    300
gagagcccgc ttagctccga cgccatcttc cgacagagcc atgcaggtct tctgaatcta    360
tgcattgttg tgctgattgc agtgaacagc aggctcatta tcgagaactt aatgaagtat    420
ggcctattaa taagagctgg gttttggttt agtgcaagat cgctgggaga ttggccactt    480
ctgatgtgct gcctcacttt acccattttc ccacttgctg cactcatgac cgagaagtgg    540
gctcaaagaa agctcatccg tgatcatgtg tctattcttc tccatataat tattacaacc    600
actgtcctta tctatccggt tgttgtgatt cttaagtgtg aatcagcagt attatctgga    660
tttgtgttaa tgttcattgc aagcattact tggttgaagc ttgtctcttt tgctcataca    720
aattatgata taagggtgtt gtcccaaagt attgaaaagg gcacatgtta tggcagttct    780
atcgatgagg aaaacattaa aggcccaact atcaacagtg ttgtgtattt catgttggcc    840
ccaaacacttt gttaccagcc aagttatccc cggacagcat ttactaggaa aggctgggtc    900
actcggcagc ttataaaatg cgtagttttt acaggcttga tgggcttcat aattgagcaa    960
tacattaatc caattgtgca gaattccaag catccattaa aaggaaattt cttggatgct   1020
attgagagag tcttgaaact gtcagtgcca acattatatg tatggctttg tatgttctat   1080
tccttttttcc atctgtggtt gaatattctt gccgaactcc tccgttttgg tgatcgtgaa   1140
ttctacaagg actggtggaa tgccaaaaca gttgaagagt actggagaat gtggaatatg   1200
cctgttcata agtggatcgt tcgccatata tttttccat gcataaggaa tggcttgtca   1260
aagggttgtg ccattctcat cgcatttctg gtttcagctg tatttcatga gctatgtatt   1320
gctgttccat gccacatttt caaattatgg cgctttctg gaatcatgtt tcagattccc   1380
ctgctattct tgacgaaata tcttcaagaa agttcaaga acacaatggt gggcaacatg   1440
atattttggt tcttcttcag catagttggg cagccaatgt gtgttctctt gtactaccat   1500
gatgtcatga acagacaggc tcagacaaat ggctag                             1536

SEQ ID NO: 20         moltype = AA  length = 511
FEATURE               Location/Qualifiers
source                1..511
                      mol_type = protein
                      organism = Triticum aestivum
SEQUENCE: 20
MSKGNPDPPP PRQLPPFPRR AAHRNPKPRP EPSGTSPPVP PMAPPPSVAA AHDRDDPSLR     60
LRRAPAADGV HGEAEPQEQP QRQHEMPCYR ASAPAHRRVK ESPLSSDAIF RQSHAGLLNL    120
CIVVLIAVNS RLIIENLMKY GLLIRAGFWF SARSLGDWPL LMCCLTLPIF PLAALMTEKW    180
AQRKLIRDHV SILLHIIITT TVLIYPVVVI LKCESAVLSG FVLMFIASIT WLKLVSFAHT    240
NYDIRVLSQS IEKGATHGSS IDEENIKGPT INSVVYFMLA PTLCYQPSYP RTAFTRKGWV    300
TRQLIKCVVF TGLMGFIIEQ YINPIVQNSK HPLKGNFLDA IERVLKLSVP TLYVWLCMFY    360
SFFHLWLNIL AELLRFGDRE FYKDWWNAKT VEEYWRMWNM PVHKWIVRHI YFPCIRNGLS    420
KGCAILIAFL VSAVFHELCI AVPCHIFKLW AFSGIMFQIP LLFLTKYLQE KFKNTMVGNM    480
IFWFFFSIVG QPMCVLLYYH DVMNRQAQTN G                                  511

SEQ ID NO: 21         moltype = DNA  length = 1485
FEATURE               Location/Qualifiers
```

```
source                  1..1485
                        mol_type = genomic DNA
                        organism = Zea mays
SEQUENCE: 21
atggccccgc cccctccat gcctgccgcc tccgatcgcg ccggccctgg ccgcgacgcg    60
ggcgactcgt cctcccttcg cctccgccgc gcccccctcag ccgacgccgg cgaccttgcc   120
ggcgattcct cgggaggctt gcgggagaac ggcgagccgc aatcgccgac gaatccgccg   180
ccgcaggagc agcagcagca cgagatgcta tactaccgcg cgtcggcgcc cgcccaccgc   240
cgcgtcaagg agagccccct cagctctgac gccatcttcc ggcagagcca tgctggtctt   300
ctgaatctat gcattgttgt tctgatcgca gtgaacagca gactcattat tgagaattta   360
atgaagtatg gcctgttgat aagagctgga ttttggttta gtgcaagatc gctgggtgac   420
tggccccttc taatgtgctg cctcactcta ccagttttcc cactagttgc actcatggct   480
gagaagctga tcacaagaaa gctcattggt gaacatgtgg ttattctact ccatatcatt   540
attacaacat ctgccattgt ctatccagtt gttgtgactc ttaagtgtga ctcagcagta   600
ctatctggat ttgtgctaat gtttcttgcg agcatcatgt ggatgaagct tgtctcttat   660
gcacatacaa attatgatat aagggtattg tccaaaagta ctgaaaaggg tgctgcatat   720
ggaaattatg tcgatcctga aatatgaaa gatccaacct taaaagtct agtgtacttt    780
atgttggccc caacactttg ttaccagcca acttatcctc aaactacatg tattagaaag   840
ggttgggtga cccagcaact cataaagtgc gtggtttta caggcttgat gggcttcata    900
attgagcaat atataaaccc aattgtgaag aattccaaac atccactgaa agggaatttt   960
ttgaatgcta tagaaagagt cttaaaactc tcagtgccaa cattatatgt atggctttgc  1020
atgttctatt gctttttttca tttatggctg aacattgtag tgcaactcct ctgtttcggt  1080
gaccgtgaat tctataagga ctggtggaat gccaaaactg ttgaagagta ctggaggatg   1140
tggaacatgc ctgttcataa gtggatcatc agacacatat attttccatg tataaggaaa   1200
ggcttttcca ggggtgtagc tattctaatc tcgtttctgg tttcagctgt atttcatgag   1260
atatgtattg cggtgccttg ccacattttc aaattctggg cattttctgg gatcatgttt   1320
cagatacccc tggtattctt gacaagatat ctccatgcta cgttcaagca tgtaatggtg   1380
ggcaacatga tattttggtt cttcttcagt atagtcggac agccgatgtg tgtccttcta   1440
tactaccatg acgtcatgaa caggcaggcc caggcaagta gatag                   1485

SEQ ID NO: 22          moltype = AA   length = 494
FEATURE                Location/Qualifiers
source                 1..494
                       mol_type = protein
                       organism = Zea mays
SEQUENCE: 22
MAPPPSMPAA SDRAGPGRDA GDSSSLRLRR APSADAGDLA GDSSGGLREN GEPQSPTNPP    60
PQEQQQHEML YYRASAPAHR RVKESPLSSD AIFRQSHAGL LNLCIVVLIA VNSRLIIENL   120
MKYGLLIRAG FWFSARSLGD WPLLMCCLTL PVFPLVALMA EKLITRKLIG EHVVILLHII   180
ITTSAIVYPV VVTLKCDSAV LSGFVLMFLA SIMWMKLVSY AHTNYDIRVL SKSTEKGAAY   240
GNYVDPENMK DPTFKSLVYF MLAPTLCYQP TYPQTTCIRK GWVTQQLIKC VVFTGLMGFI   300
IEQYINPIVK NSKHPLKGNF LNAIERVLKL SVPTLYVWLC MFYCFFHLWL NIVAELLCFG   360
DREFYKDWWN AKTVEEYWRM WNMPVHKWII RHIYFPCIRK GFSRGVAILI SFLVSAVFHE   420
ICIAVPCHIF KFWAFSGIMF QIPLVFLTRY LHATFKHVMV GNMIFWFFFS IVGQPMCVLL   480
YYHDVMNRQA QASR                                                    494

SEQ ID NO: 23          moltype = DNA   length = 1539
FEATURE                Location/Qualifiers
source                 1..1539
                       mol_type = genomic DNA
                       organism = Elaeis guineensis
SEQUENCE: 23
atggcggtct cgaagaatcc agaaacccta gccccgatc aagaaccgtc gaaggagtcg     60
gatctccgcc ggaggccggc ttcctccccc tcctccaccg ccgcttcgcc ggcggttccg   120
gactcgtctt caagaacgag ctcttccatc accgggagct ggaccacggc gttagatgga   180
gattctggtg caggagctgt ccgcattggt gatccaaagg atcggatagg cgaggcgaac   240
gatattggtg aaaagaagaa ggcctgttcg ggtgaagttc cggtgggtt cgtggaccgg    300
ccttcagctc cggtgcatgt gagagtggtg gagagcccgc tgagctcgga tacgatcttt   360
caacagagcc atgcaggtct cttgaacctt tgtgtagtag ttctgattgc agttaacagc   420
aggcttatta ttgagaactt gatgaagtat ggtttactaa taggaagtgg attttcttc    480
agttcaagat tactgaggga ttggccacta cttatatgta gtctcactct acctgttttc   540
cctcttggat cttacatggt tgaaaagctg gcatataaga agttcatttc tgaacctgtt   600
gttgtctcac ttcatgtaat actcataata gctaccatca tgtatccagt tttcgtgatt   660
ctaaggtgcg attctcctat tttatctggc atcaatctaa tgctcttttg gagctcatt    720
tgcctaaagc ttgtttcata tgcacatgca aattacgatt taaggtcatc atccaactct   780
attgataagg ggatacacaa gtctcaaggt gttagcttca aaagtttggt gtatttata    840
atggctccca cgctatgtta ccagccaagt tatcctcgga ctacgtgcat cagaaagggt   900
tgggtgattt gtcagcttgt taagttggtg atatttactg gggtgatggg cttcatcatt   960
gagcagtaca ttgacccgat tatcaagaat tctcaacatc ctctaaaagg aaatgtctta  1020
aatgctatgg agagagtctt gaagctatca ataccaactt gtacgtgtg ctttgtgta    1080
ttctattgca ccttccattt gtggttaaac attcttgctg agctcctttg ttttggtgat  1140
cgtgaattct ataagattg gtggaatgca aaaacaattg aagagtattg gagaatgtgg   1200
aacatgcctg ttcataaatg gatgcttcgc catgtttatc ttccatgcat acggaatggt  1260
ataccaaagg gagttgcgat ggtcatctca ttttcattt cctgtctatt ccatgagcta   1320
tgcattggta tccccctgcca tatattcaag ttctgggctt tcataggat aatgtttcag  1380
gttccacttg tcatcttgac aaagtaccct cagaataaat taaaagtgc catggtggga   1440
aacatgatct tctggttctt cttcagcata tatggacagc ctatgtgtgt tctgctttac   1500
taccatgatg tgatgaacag aaaagtggga acagagtaa                          1539
```

```
SEQ ID NO: 24              moltype = AA  length = 512
FEATURE                    Location/Qualifiers
source                     1..512
                           mol_type = protein
                           organism = Elaeis guineensis
SEQUENCE: 24
MAVSKNPETL APDQEPSKES DLRRRPASSP SSTAASPAVP DSSSRTSSSI TGSWTTALDG    60
DSGAGAVRIG DPKDRIGEAN DIGEKKKACS GEVPVGFVDR PSAPVHVRVV ESPLSSDTIF   120
QQSHAGLLNL CVVVLIAVNS RLIIENLMKY GLLIGSGFFF SSRLLRDWPL LICSLTLPVF   180
PLGSYMVEKL AYKKFISEPV VVSLHVILII ATIMYPVFVI LRCDSPILSG INLMLFVSSI   240
CLKLVSYAHA NYDLRSSSNS IDKGIHKSQG VSFKSLVYFI MAPTLCYQPS YPRTTCIRKG   300
WVICQLVKLV IFTGVMGFII EQYIDPIIKN SQHPLKGNVL NAMERVLKLS IPTLYVWLCV   360
FYCTFHLWLN ILAELLCFGD REFYKDWWNA KTIEEYWRMW NMPVHKWMLR HVYLPCIRNG   420
IPKGVAMVIS FFISAIFHEL CIGIPCHIFK FWAFIGIMFQ VPLVILTKYL QNKFKSAMVG   480
NMIFWFFFSI YGQPMCVLLY YHDVMNRKVG TE                                 512

SEQ ID NO: 25              moltype = DNA  length = 1449
FEATURE                    Location/Qualifiers
misc_feature               1..1449
                           note = soybean DGAT1A with 48 bp deletion
source                     1..1449
                           mol_type = other DNA
                           organism = synthetic construct
SEQUENCE: 25
atggcgattt ccgatgagcc tgaaactgta gccactgctc tcaaccactc ttccctgcgc     60
cgccgtccca ccgccgactt ggccaaggat tccggttccg acgactccat cagcagcgac   120
gccgccaatt cgcaaccgca acaaaaacaa gacactgatt tctccgtcct caaattcgcc   180
taccgtcctt ccgtccccgc tcatcgcaaa gtgaaggaaa gtccgctcag ctccgacacc   240
attttccgtc agagtcacgc gggcctcttc aacctctgta tagtagtcct tgttgctgtg   300
aatagccgac tcatcattga gaatttaatg aagtatgggt ggttgatcaa atctggcttt   360
tggtttagct caaagtcatt gagagactgg cccctcttca tgtgttgtct ttctcttgtg   420
gtatttcctt tgctgcatt tatagtggag aagttggcac agcagaagtg tacccgaa     480
ccagttgttg ttgtacttca tataatcatt acctcagctt cacttttcta tccagtttta   540
gtaattctca ggtgtgattc tgcttttcta tcaggtgtta cgttaatgct atttgcttgt   600
gttgtatggt taaaattggt gtcttatgca catacaaact atgatatgag agcacttacc   660
aaatcagttg aaaagggaga agctctgccc gatactctga acatggacta tccttacaat   720
gtaagcttca agagcttagc atatttcctg gttgcccta cattatgtta ccagccaagc   780
tatccctcgca caccttatat tcgaaagggt tggctgtttc gccaacttgt caagctgata   840
atatttacag gagttatggg atttataata gaacaaatat tttaatcccat tgtacaaaat   900
tcacagcatc ctctcaaggg aaaccttctt tacgccatcg agagagttct gaagctttct   960
gttccaaatt tatatgtgtg gctctgcatg ttctattgct ttttccacct ttggttaaat  1020
atattggcag agcttcttcg atttggtgat cgtgaattct accaggattg gtggaatgcc  1080
aaaactgttg aagattattg gaggatgtgg aatatgcctg ttcacaaatg gatgatccgc  1140
cacctatatt ttccatgttt aaggcacggt ataccaaagg ccgttgctct ttaattgcc   1200
ttcctggttt ctgctttatt ccatgagctg tgcatcgctg ttccttgcca catattcaag  1260
ttgtgggctt tcggtggaat tatgtttcag gttcctttgg tcttcatcac taattatctg  1320
caaaataaat tcagaaactc gatggttgga aatatgattt ttggttcat attcagtatt   1380
cttggtcaac ctatgtgcgt actgctatat taccatgact taatgaatag gaaaggcaaa  1440
cttgactga                                                         1449

SEQ ID NO: 26              moltype = DNA  length = 1455
FEATURE                    Location/Qualifiers
misc_feature               1..1455
                           note = soybean DGAT1B with 60 bp deletion
source                     1..1455
                           mol_type = other DNA
                           organism = synthetic construct
SEQUENCE: 26
atggcgattt ccgatgagcc tgaaagtgta gccactgctc tcaaccactc ttccctgcgc     60
cgccgtccct ccgacttggc caaggattct ggttccgacg actccatcaa cagcgacgac   120
gccgccgtca attccaaaca gcaaaacgaa aacaagaca ctgatttctc cgtcctcaaa    180
ttcgcctacc gtccttccgt cccccgctcac cgcaaagtga aggaaagtcc gctcagctcc   240
gacactattt tccgtcagag tcacgcgggc ctcttcaacc tttgtatagt agtccttgtt   300
gctgtgaata gccgactcat cattgagaat taatgaagt atggttggtt gatcaaatct   360
ggcttttggt ttagttcaaa gtcattgaga gactggcccc ttttcatgtg ttgtctttct   420
cttgtggtat ttccttttcgc tgcctttata gtggagaagt tggcacaacg gaagtgtata   480
cccgaaccag ttgttgttgt acttcatata atcattacct caacttcgct tttctatcca   540
gttttagtta tttcaggtg tgattctgct tttgtatcag gtgtcacgtt aatgctgttt   600
tcttgtgttg tatggttaaa attggtgtct tatgcacata caaactatga tagagcact   660
cttaccaaat tagttgaaaa gggagaagca ctgctcgata tctgaacat ggactatcct   720
tacaacgtaa gcttcaagag cttggcatat tccggttg ccctacatt atgttaccag    780
ccaagctatc ctcgcacacc ttatattcga aagggttggt gtttcgcca acttgtcaag   840
ctgataatat ttacaggagt tatgggattt ataatagaac aatatattaa tccatagta   900
caaaaatcac agcatctc caagggaaac cttcttacg ccaccgagag ttctgaag     960
ctttctgttc caaatttata tgtgtggctc tgcatgttct attgcttttt ccacctttgg  1020
ttaaatatcc tggcagagct tcttcgattt ggtgatcgtg aattctacaa ggattggtgg  1080
aatgccaaaa ctgtcgaaga ttattggagg atgtggaata tgcctgttca aaatggatg   1140
atccgccacc tatattttcc atgtttaagg cacggtctac aaaggctgc tgctctttta   1200
attgccttcc tggtttctgc tttattccat gagctgtgca ttgctgttcc ttgccacata  1260
```

```
ttcaagttgt gggctttcgg tggaattatg tttcaggttc ctttggtctt gatcactaat   1320
tatctgcaaa ataaattcag aaactcaatg gttggaaata tgattttttg gttcatattc   1380
agtatccttg gtcaacctat gtgtgtactg ctatactacc atgacttgat gaataggaaa   1440
ggcaaacttg actga                                                    1455

SEQ ID NO: 27           moltype = AA  length = 504
FEATURE                 Location/Qualifiers
REGION                  1..504
                        note = soybean DGAT1b with 60bp deletion
source                  1..504
                        mol_type = protein
                        organism = synthetic construct
SEQUENCE: 27
MAISDEPESV ATALNHSSLR RRPSATSTAG LFNSPETTTD SSGDDLAKDS GSDDSINNDD    60
AAVNSQQQNE KQDTDFSVLK FAYRPSVPAH RKVKESPLSS DTIFRQSHAG LFNLCIVVLV   120
AVNSRLIIEN LMKYGWLIKS GFWFSAKSLR DWPLFMCCLS LVVFPFAAFM VEKLAQRKCI   180
PEPVVVVLHI IITSTSLFYP VLVILKCDSA FVSGVTLMLF SCVVWLKLVS FAHTNYDMRA   240
LTKLVEKGEA LLDTLNMEYP YNVTFKSLAY FLLAPTLCYQ PSYPRTPYIR KGWLFRQLVK   300
LIVFTGVMGF IIEQYINPIV QNSQHPLKGN LLYATERVLK LSVPNLYVWL CMFYCFFHLW   360
LNIVAELLRF GDREFYKDWW NAKTVEDYWR MWNMPVHKWM IRHLYFPCLR HGLPKAAALL   420
ISFLVSALFH ELCIAVPCHM FKLWAFGGIM FQVPLVLITN YLQNKFKNSM VGNMIFWFIF   480
SIVGQPMCVL LYYHDLMNRK GKLD                                         504

SEQ ID NO: 28           moltype = AA  length = 498
FEATURE                 Location/Qualifiers
REGION                  1..498
                        note = soybean DGAT1A with 48 bp deletion
source                  1..498
                        mol_type = protein
                        organism = synthetic construct
SEQUENCE: 28
MAISDEPETV ATALNHSSLR RRPTAAGLFN SPETTTDSSG DDLAKDSGSD DSISNDAANS    60
QPQQKQDTDF SVLKFAYRPS VPAHRKVKES PLSSDTIFRQ SHAGLFNLCI VVLVAVNSRL   120
IIENLMKYGW LIKSGFWFSA KSLRDWPLFM CCLSLVVFPF AAFMVEKLAQ QKCIPEPVVV   180
VLHIIITSAS LFYPVLVILK CDSAFLSGVT LMLFACVVWL KLVSFAHTNY DMRALTKSVE   240
KGEALPDTLN MEYPYNVTFK SLAYFLLAPT LCYQPSYPRT PYIRKGWLFR QLVKLIVFTG   300
VMGFIIEQYI NPIVQNSQHP LKGNLLYAIE RVLKLSVPNL YVWLCMFYCF FHLWLNIVAE   360
LLRFGDREFY QDWWNAKTVE DYWRMWNMPV HKWMIRHLYF PCLRHGIPKA VALLISFLVS   420
ALFHELCIAV PCHMFKLWAF GGIMFQVPLV FITNYLQNKF KNSMVGNMIF WFIFSIVGQP   480
MCVLLYYHDL MNRKGKLD                                                498

SEQ ID NO: 29           moltype = DNA  length = 8217
FEATURE                 Location/Qualifiers
source                  1..8217
                        mol_type = genomic DNA
                        organism = Glycine max
SEQUENCE: 29
ggagaagaga agactgagtt agaaaacacg ctcggtcttc ttctccaatg gcgatttccg    60
atgagcctga aagtgtagcc actgctctca accactcttc cctgcgccgc cgtccctcgg   120
ccacctccac cgccggcctc ttcaattcgc ctgagcaaac caccgacagt tccggtgatg   180
acttggccaa ggattctggt tccgacgact ccatcaacag cgacgacgcc gccgtcaatt   240
cccaacagca aaacgaaaaa caagacactg atttctccgt cctcaaattc gcctaccgtc   300
cttccgtccc cgctcaccgc aaagtgaagg aagtccgct cagctccgac actatttttcc   360
gtcaggttct cgccgttaac ttctacttta cgattactac aactctttaa ctatttcaaa   420
ctcaaccaga acggtgccgt tttgttcccg ttctgcataa taaacttcc aatctcaatg   480
caagcgaatc gtagtctttg aggtgcttaa aatagtgtat gctactgcta gttagtctt   540
gtttatttaa tttatgtgta ctagaaacta gttatcaatt tatgatttga atttaataca   600
attgaattgg tggatcaggt tttgtagca attatcgtgg tttggtttat aaataggtgt   660
gatgagtctg atatgtaatt atatttcttt actaattatt gaatcggtta cagagtcacg   720
cgggcctctt caacctttgt atagtagtcc ttgttgctgt gaatagccga ctcatcattg   780
agaatttaat gaaggttttg cttcttccat gtttaaattg tacattcacc tgcaacaatt   840
tttctgttct tttatttatg gtcttgattt tgacggttca ggtttattg tctgctttaa   900
tgagtgtttt atttgttctg cagtatggtt ggttgatcaa atctggcttt ggttagtt   960
caaagtcatt gagagactgg cccctttttca tgtgttggta gtagtgatg aatcccttg  1020
tggattaact gtgtactgtg taattgtttt gacggttgct tcttgaaatg ttgtttaaca  1080
gtatgtggtt gtgcgcttgg tttgcagtct ttctcttgtg gtattccttt cgctgccttt  1140
tatagtggag aagttggcac aacggaagtg tatacccgaa ccagtaagtg accaggccat  1200
gtgagctttt attagatttc attcgttgta taatctaaaa tagtttttgg atatggttag  1260
ttgtatgtgc tattattaac tcgttaatct ttaatatttg catacattgg aatattatat  1320
tacttgaata ttgcaggttg ttgttgtact tcatataatc attacctcaa cttcgctttt  1380
ctatccagtt ttagttattc tcaggtcagt ttagttcttt gtatacattc ttcaaaattt  1440
attctagggc tgcagttgat gacccttcg ttttgacatg tgcggttaca ccatgtgtcc   1500
atttttgaaag aatttgctta tagaaatggg ttttaagttg ataatggtgt tatataacaa  1560
actttgtcac tatactgcac aggaattta aaaacttttta tcattttatta aaatatttg  1620
agaaaaaaatt taagccgtt gggtgaacct tagtttaatg tttggttctt atgattttgc  1680
aattgaattg ttgcaaaata ttattgcatt gctatatgaa cattgagcaa tgaagttgaa  1740
tgctgcggga taagtaatt atacagttgt gcgttcttag tcatttcata gataaggata  1800
tcccagaaag atgattacta acttgtagca ttcccttgca ggtgtgattc tgcttttgta  1860
tcaggtgtca cgttaatgct gttttcttgt gttgtatggt taaaattggt gtcttatgca  1920
```

-continued

```
catacaaact atgatatgag agcacttacc aaattagttg aaaaggtaat aaatactctc   1980
tgtttaaatg gagagaaaat gaggggggaga gaaaattttg aattttttt cttgaagtca   2040
acttttccct cttctcttta actaaacaaa agaaaatgta tgattatgtg ttttttcttt   2100
catctaattt tttccttaac caaacatatt cttaagttcc acttgacact tgtaagtggc   2160
tagataaata tcacaaaatg tcatcttcac ttatttgtat acttaaaga tgacagtttg    2220
ttgtacaatg attagttttt gaaccagaac atcctgcttg acttagcagt agcttatgga   2280
tcatgtacta ttaaaacttc ataatatgct aaagtacagt tttatttcat ctaaattcga   2340
attacttcca tcctatgttc cccttttattg cttccttata tctagatgat tagctcttca   2400
catgtgtgaa tgtgccatag ataaaccatc tgtttcccct ccttattcaa acatgtttgc   2460
tgtgttatag ggagaagcac tgctcgatac tctgaacatg gactatcctt acaacgtaag   2520
cttcaagagc ttggcatatt tcctggttgc ccctacatta tgttaccagg tagcagtact   2580
ttcaagtgat ttagttaatt tttggaagca atttcttttt atttgtaatt gttgtggtgt   2640
tgcctcattt agattggcct attttacatt tgcattcatt tttcttgtct tagattgctt   2700
ataggcacaa ccatgtgcag ttgcttaccc atatatcttt ggtgtggact atgtctgagg   2760
tttttagtca gtgtctaatt ggacatgctg ttgggaaccc agaaacagaa tacaagaaaa   2820
gaatgcttct tgtactgaaa aattgaatga caacaaagaa aagaggagaa ttttgctcaa   2880
agggtttctc cacagcagag attctcagtt tacaaatgct aacaaatttg aatgacttcc   2940
cccccccccc cccccccaaa aaaaaggta taattgctct aactaataat caaactaatt   3000
gctctaacca tcccaactaa tttccccttc cctctctcct aactccgtaa cagggtgaac   3060
ataattacac tgctaggaat taagttccca tctaaaaggt ataattgatc cagaatgttg   3120
agttggctgt gtgatcactt gattcttaca tagtaggatt tctccgaatg acttaaatta   3180
ttgtctattc tattcctttc agcaaatttc tccatttatc atcctgtctt tccttttccat  3240
cttctaattt tggccatttg accttgttca tctcacattc aatactcttt tctatttttt   3300
tggcatgcgc ttagacaaca caacatttg tagcataaaa tattgtgtaa tgaaatctat    3360
agcaggaatc tcccgaacct ttctcatgct cccccttttac ttccattcat acaaaattcc  3420
caatgtacaa ttcctattgc aatctgctag tttctagaca caacctgcta atcaatgcaa   3480
gggggaggggg aggggggggta gtagccactg ttagtcaatg tgttcttcaa tctgcttata  3540
attctgcttg cttcttgctt ttatatgatt agaagctaag aataagattt taagggaatg   3600
ggtattacat gactccctgg cataaaatgt agcatacatt tctaatgctt tgtgagaata   3660
ctggattggc tttggcatct tcagtgttta cctaagttgc agaaattttg cttgcggttc   3720
tttaagtagg tttctgcagt tcatttgtct ttgccttttc ctgcataaat tgtatatccat  3780
gtagattgca tttgttattt ttttcttctg tgagcaaggt ttttcacatt tttatttgca   3840
tctattttgt tttatgaact gctcttttag ccaagctatc ctcgcacacc ttatattcga   3900
aagggttggt tgtttcgcca acttgtcaag ctgataaatt ttacaggagt tatgggattt   3960
ataatagaac aagtaagcag ttcctgttaa taaattgtgt tcatttctac ttttttttcct 4020
ttcttttttt tttgtgcatt ttttttcttca ggtttatttc accaattcta ctggtattct  4080
gacattattt tgattgtaaa attctgcagt atattaatcc catagtacaa aattcacagc   4140
atcctctcaa gggaaaacctt ctttacgcca ccgagagagt tctgaagctt tctgttccaa   4200
atttatatgt gtggctctgc atgttctatt gcttttttcca cctttggtat tccatctctt  4260
gtttggttca acatgtgtgt gtgcattttt cttataagat attagtctga actatgaagt   4320
taatttcacc tgccataaat tgaatagctg tagttcttgt atcttttgtt taatgccttg   4380
acttttgtac cctggcaatt ttcagatgat gatgatgtta aagtttgta attgattaat    4440
ctttcaaatc atcgttgaaa tgatatccac cttcctaaac accttaaata gtaattacat   4500
catcaatggg aggatctagc taatttaaag gtgtgcatgt agagactatt gttgtctgga   4560
ctctggagta tatacttctt aagatataaa attaacttta tagcctgttt ggtgtgccac   4620
aattgattaa tttaagtgac actctgacag atatacgaag ggattttaga gccttatttt   4680
attgatggat ttgtatattt ttcctgtggc cagtgaggat atttttattca tgtatgcttg   4740
attttctcc tctttaatag aactactatt agaaaaaact agatctcttt gtgcatgcgt    4800
aaatgttgat ctgattgtct catttctaga tattagaaaa tgttcacctt tgttttttta   4860
agatttagtt catatttgag gcagcttatc attggagtga ctgttccaat gtaggttaaa   4920
tatcctggca gagcttcttc gatttggtga tcgtgaattc tacaaggatt ggtggaatgc   4980
caaaactgtc gaagatgcaa gttatttgtc ctgatatttt gttgtttact tacagtattt   5040
tcagtctttc ataaagagaa tttgtgactt attgttttct tgtattttg ctgttgttgc    5100
tgcttccatc agtattggag gatgtggaat atggtatgtc tctttttcag acttaatttt   5160
gatgaacaaa ttgatttttct tgttgtcagc aaaatgattt tctggttttct tgttgggatg  5220
aaattcaagt gaacacacac acacacacat atatttgata taactatccc ttaagtgtat   5280
aatgagggtt gactactctc cgagactatt ttaacaaagg aagaaagaga agttacaaca   5340
ttttgccatc ttactgaata aatggtttta aaactgtctt tcagaacata tcattgatta   5400
ttcatcactt aaagttccaa accattagta taatctgagt ggaatctttt acattgcagc   5460
ctgttcacaa atggatgatc cgccacctat atttttccatg tttaaggcac ggtctaccaa   5520
aggtaatcaa gcatcctcct gtgttgctga atggatcctg aatttatttg gtctaaactc   5580
taaaacattt ttaggatttg tcagtctctg tttaccatct caggttgcca ctaagatgat   5640
cacatttaac atagttaaat taaaaggaac atgtatgtta gttatatcct aataatcaca   5700
gttatgtaaa aacttatcaa taaacctatt acataagtt ttttttttta aaaagtagtt    5760
atatattttt tttgcactaa ttgtatggtt tgatatgttt gatgcactgg aggaatatgt   5820
agaaagttt caattggtag acaatagttg aactgcattt ctgttctgtc gtttcagata    5880
aatgactttg gaatgtataa acttgactaa cacaaacaag aactgcaaac gaactccatt   5940
atttttttt cttatgtaat catggttgat atctttgtga tttttttcct tggtcttgc     6000
tatcaacaat ttcctatcaa cagtagtttgtt tctcattggt taatatttgt attggctctt  6060
gttttttaaa gcattattgg tattttaatt tcagttcta gataatgttt tgattttca     6120
tcattgtaca ggctgctgct cttttaattg ccttcctggt ttctgcttta ttccatgagg   6180
tgtgttgttc atctctctgt acagccttct ctcttccttt tttggtatta tgtcattatg   6240
gttttctgct tgagtatttg tctgcattct acactgatca atgtcaggaa gcatcttgca   6300
atcaatatat ttttcttgg aatattctttcctt ttttcctg ggctgtttgg actgtgttag  6360
gagttagata gaagggaagg gaaaattatt tacagacggt tagagttgtt aattagtcag   6420
ttacaggatt tggttagata taaataggg gtattaagag gaaatgatcc attctatttg    6480
ttatcatttg agaattgagc tttgctattt tgaaaggaaa aatcctttgt gagggggaaa   6540
cccttggagg agagttatct ttcctatttt ctgttttaga tgataaaagt gttctttat    6600
ttcttttcttt gctttgggtt cgtaacagac tgtgggagag aactgaaaat tagatactaa   6660
```

```
gttgtggctg atttgttaaa aattggtata ggacctacgt tacttgtctt tgaactatct  6720
acaacctcat atggcctcag aaaccttagc cttaggcagc tagttaccaa aatctcaagt  6780
aacttgtagc ctgtctgtac cttggcatgt gtagatgtta cagcttccat atcttaaaat  6840
agattgacat aacaattatg agggactgtc acattttcta gtttccacct gagttcttgc  6900
aatattaact ttggcaccaa aatttcccta catgtactca aggatgcttt ctttagccat  6960
gaataatttt tttcacatgt tgtaattatg ttttcaatta atcctgtcat cttttcctcc  7020
tgaaaaggt acatacgcag ataagaataa tttgataact taattgtcac agacagttgt  7080
gcaattttt tcacgatatc tctatcatct gagtgcagct gtgcattgct gttccttgcc  7140
acatattcaa gttgtgggct ttcggtggaa ttatgtttca ggtaaaatca aattaccgta  7200
ttatacttct gttttcccat cttctattat taaactaaag tattttaatt tagagcaaga  7260
gtaacacaaa ttttccaaga aaccaaactt ctcccctctt ccctcacgaa gaaggtgaag  7320
gattgcccag attttgtctt ttcctgttct tttatggcca aatgaaagaa agtattctct  7380
gaagtaatga atctgtgcca tgtttgaagt agttgatgat tatgatatca tccatacttt  7440
tggttcaatt gacatgatca tgaatgcccg gttttttaggt tcctttggtc ttgatcacta  7500
attatctgca aaataaattc agaaactcaa tggtacgtct gctatttaag tatatcagtt  7560
cataaatcat aatgtatctt ataactccca tcatcttgaa tttgattcgt tggtttttta  7620
atgttatttt cttcatgcca ggttggaaat atgattttt ggttcatatt cagtatcctt  7680
ggtcaaccta tgtgtgtact gctatactac catgacttga tgaataggaa aggcaaactt  7740
gactgaagct acggccatta cattttaaag gtgcacatgg atgagctttt cagttttcag  7800
attgtaaaat tgatgtggat atgttggtca atatttgttt tctacgaatg ctttcatcta  7860
ccatggcatt ggctgctctg aaggaattcc acgggatatg ccagttcacg aggctaattc  7920
attatcttga tctatgtact taccaactct cctctggcaa ttgtatcaaa atatgcaatt  7980
ttgagagcca tacactggca ttgataactg ccaaggaaca ctctaactgt tttctgttaa  8040
ctgttaatta gtagagggct agatgtaaat ggtttatgct caatatattt atttcctcct  8100
agtcttcaag ttccacggat gaatgatgtc tttatagcag ttttttttctt ctacaaaact  8160
tgcatatcac tttaaaggta ttgtttgtgt tgttttttgct gatcataatt gaagttt     8217

SEQ ID NO: 30          moltype = DNA   length = 8243
FEATURE                Location/Qualifiers
source                 1..8243
                       mol_type = genomic DNA
                       organism = Glycine max
SEQUENCE: 30
tagaaatctg ttgtttattt tttggtgaag agaagactga gttagtaaac acgtcgctc    60
ggtcttcttt tccaatggcg atttccgatg agcctgaaac tgtagccact gctctcaacc   120
actcttccct gcgccgccgt cccaccgccg ctggcctctt caattcgccc gagacgacca   180
ccgacagttc cggtgatgac ttggccaagg attccggttc cgacgactcc atcagcagcg   240
acgccgccaa ttcgcaaccg caacaaaaac aagacactga tttctccgtc ctcaaattcg   300
cctaccgtcc ttccgtcccc gctcatcgca aagtgaagga aagtccgctc agctccgaca   360
ccattttccg tcaggttctc gccgttaact tctactttac aattattaca attccgtaac   420
tatttcaaac tcaaccagaa cggtaccgtt tcgttcccgt tctgcattaa taaactactc   480
aatctcaatg catgactcat gaatgcaagc gactcgtagt cttttaggtg cttaaaatag   540
tgtatgctac tgctagttag ttaattgtg tgtacggaga actagttatc aatttatgat   600
ttgaatttaa tacaattgaa ttggtggatc aggtttttgt acctgctatt gtgtttggtt   660
tataattagg tgtgatgagt ctgatatgta attatatttc tttactaatt attcaatcag   720
ttgcagagtc acgcgggcct cttcaacctc tgtatagtag tccttgttgc tgtgaatagc   780
cgactcatca ttgagaattt aatgaaggtt ttgcctcttc catgtttaat tgtgcattca   840
cctgcaacaa ttttctgttc tttttattta tgaccttgat tttgacggtt cgggttttgt   900
tgtctgcttt aatgagtgtt ttatttgttc tgcagtatgg ttggttgatc aaatctggct   960
tttggttag ctcaaagtca ttgagagact ggccctcttt catgtgttgg taatgagtgt  1020
aatgaattcc ctaaagaatt aactatgtac tatgtaatta ttctgaaatg ttgttcaaca  1080
gtatgtggtt gtgcacttgg tttgcagtct ttctcttgtg gtatttcctt ttgctgcatt  1140
tatagtggag aagttggcac agcagaagtg tatacccgaa ccagttaagt gatcaggcca  1200
tatgagcttt tattagattt cattcgtttt ataacctaaa atattttgg gatatggtta  1260
gttgtgatgt gctattctta actgttcaat ctttaattat tgcatacatg agaatattat  1320
attactttaa tattgcaggt tgttgttgta cttcatataa tcattacctc agcttcactt  1380
ttctatccag ttttagtaat tctcaggtca gttaagttct tttgtatata ttctggggct  1440
gcagttgagg caccttttgt tttgacatgg gtggttacac aatgtgtcca tttttgaaaga  1500
atttggtaat agaatatggt tttaagttga tagtggtgtt aagtaacaaa ctttgtcact  1560
atcctgcaca ggaattttaaa tttttttatt atattttaaa attacttgag aagaaattta  1620
aagcatttgg gtgaacctta gtttaatgtt tggttcttat catgtggaa ttgaattatg  1680
ttgcaaaata tgaagatgaa tgctgaggga tgaaataatt atacagttgt gcattcttag  1740
tcatttcata gataaggata tcccagaaag atgattactg acttgtaaca ttctttgcag  1800
gtgtgattct gcttttctat caggtgttac gttaatgcta tttgcttgtg ttgtatggtt  1860
aaaattggtg tcttatgcac atacaaacta tgatatgaga gcacttacca aatcagttga  1920
aaaggtaata aatactctct gttttaaacgg agagaaaatt tgaattttt ttttcttaaa  1980
agtcaacttt tctctcttgt ctttaactaa acaaagaaaa atctatcttt acgtgttttt  2040
tctttcatct aattttttcc ttaaccaaac atattcttaa attctacttg gcacttgtaa  2100
gtgggtagat aactatcaca aaatatcatc gtcacttatt tgtatacttt aaagatgacc  2160
atatgttgta caatgtttgt gatgattagt ttttgaacct gaacatcctg cttgacttag  2220
cagtagctta tggatcatgt actcttaaaa cttcattata tgctgaagta cagttttatt  2280
tcatcttcat ttgaattact tccatcctgt gttccgcttt attgcttcct tctatctaga  2340
tggttagctc ttcaaacgtg tgaatgtgtg atagataaac catctgcttt ccctccttat  2400
tcaaacatgt tcatgtcgtt ataggggaaga gctctgaaca atactctgaa catgactact  2460
ccttacaatg taagcttcaa gagcttagca tatttcctgg ttgccctac attatgttac  2520
caggtagcag tactttcaag tgatttagtt aatttttgga agcaatttt tttaattgtt  2580
gtggtgttgc ctcatttaga ttcgcctatt ttacatttgc attcacttt ctagtcttag  2640
attgcttata ggcacaacca tgtggagttg cttactcata tatctttggt gtggaatatg  2700
tctgaggttt ttagtcagtg tctaattgga catgctgttg ggaacccaga aacagagtat  2760
```

```
gagaaaagaa tgcttcttgt actaattaca gaatattgaa tgacaacaaa gaaaagggga    2820
aaattttgct caaagagttt ctcctttcac aacacagatg cttaattgaa tgactccccc    2880
ccccaaaaaa aaaaaaaaat cttcctatat gtttctcact aaccccctct aactaagaat    2940
caaactaatt gctctaacca tcccaactaa tttcactgct aggaattaag ttcccatcta    3000
acaagtataa ttgatccaga atgttgggtt ggctacatag taggatttgt ctgaatgact    3060
cttttaatcat tgtcttcaat acattctata cctttcagca aatttctcca tttattatcc    3120
tttctttcct ttccatcttc taattttggc catttgacct cgttcatctc acattcaata    3180
ctcctttcta ttttgtagca tagaatattg tgtaatgaaa tctatagcag gaatccccca    3240
aacccttctc atgccccccc tttacttcct tcgtacaaaa ttcccattgc aatctgctag    3300
tttctagaca caacctgcta gtcaatgcac ggtgtaggag ccacaatctg ttagtctatg    3360
tgttcctcaa tctgcatata atacttcttg cttcttgctt ttatatgaag ctaagaataa    3420
gattttaagg gaatgagtat tacatgactc cccggcataa aatgtagcat gcatttctaa    3480
tgctttgtga gaatactgga ttggctttgg catcttcagt gtttacctac gttgcagaaa    3540
ttttgcttgg ggttctttaa gtaggtttct gcagttcatt tgtctttgca ttttcctgca    3600
taaatgtatc tccatgtgaa ttgcatttgt tattttttttt attctgagag caaggtctttt    3660
cacatttttta tttgcatgta ttttgttttta tgaactgctc tttagccaa gctatcctcg    3720
cacacccttat attcgaaagg gttggctgtt tcgccaactt gtcaagctga taatatttac    3780
aggagttatg ggatttataa tagaacaagt aagcagttcc tgttaataaa ttgtgttcat    3840
ttctacccttt tttcatttc ttttttttatg tacattttttt tcttgaggtc tatttcacca    3900
attctactgg tattctgaca ttattttgac tgtaattttg cagtacatta atcccattgt    3960
acaaaattca cagcatcctc tcaagggaaa ccttctttac gccatcgaga gagttctgaa    4020
gctttctgtt ccaaatttat atgtgtggct ctgcatgttc tattgctttt tccacctttg    4080
gtattccatc tcttgtttgg ttcaacatgt gtgtatgtgt gtgcattttc cttacaagat    4140
attagtatga agttatcttc acctgccata aattgaataa ttatagttct agtttatttt    4200
gtttgatgcc ttgactttttg taccctgcca attttctgat gatgatgatg ttataagtta    4260
gtaattgatt aatcttttcaa atcatccttg aagtgatatc caccttccta aacaccttaa    4320
aatagtaatt acatcatcaa tgggaagatc tagctgatct aaaggtgtgc atgtagagac    4380
tattggtgtc ttgagtgtac acttctaaag atataaaata aactttatag cctgtttggt    4440
gtgccaccaa tgattaattt aagtgacact ctgacggata tgtgaaagga tttgagagcc    4500
ttatttttatt gatggatttg aatattttttc ctttggccag tgaggatata ttattcttca    4560
tttatgctct ttttttctcct ctttaagaac tactcttaga aaaaaaacta gatctttttt    4620
tgcaagcata aatgctgatc tgcttgtctc atttgtagat attagaaaag gttcacctttt    4680
gatttttttaa gatttagtta atatttgagg aagcttatca ttggagtgac tgtcgtaatg    4740
taggttaaat atattggcag agcttcttcg atttggtgat cgtgaattct accaggattg    4800
gtggaatgcc aaaactgttg aagatgtaag ttatttgtcc tgatattttg tcgtttactt    4860
acagtatttt cagtcttcat aaagagaaat tgtgacttttt tgttttttgtt tctgtatttg    4920
tgctgttgtt gctgcttcca tcagtattgg aggatgtgga atatggtatg tctctttttc    4980
agacttaatt ttgatgaaca aattgatttt cttgtgttca gcaaaatgat tttcaggtct    5040
cctgttgtga tgaaattcat gtgaacacac gtacatatat ttgatataac tatccctttta    5100
aatgtataat gagggttgac aactctccaa gactattttta acaacggaag aaagagaagt    5160
tacaactttt ttccatcctta ctgactaaat ggttttaaaa ctgtcttttca gaacatatca    5220
ttaattattt atcacgtaaa gttccaaacc attagtataa tctgagcgga atcttttaca    5280
tgcagcctg ttcacaaatg gatgatccgc cacctatatt ttccatgttt aaggcacggt    5340
ataccaaagg taatcaagca tccttctgcg ttgctgaatg gatcctgaac ttatttggta    5400
ctgtaaaaca tttttaggat ttgtcagcct ctgtttacca tctcgggttg ctactaagat    5460
catcacatttt aacatagttg aattaaaatg aacatgttac ttttatcctta ataatcacac    5520
ttatgtaaaa acttatcaat aaacctatta cataagtttt ttttcaaaaaa ataagtatttt    5580
gcactaattg tatggtttga tatgtttggt gcactggggg agctatatgt agaaagtttg    5640
caattggtag acagtaatttt agcttcatct tctgttctgt catttcagat aaattactttt    5700
ggagtgcata aacatgacta aaacaagaat tgcaaggaa ctccattaaa aaaaaaaaaa    5760
atcttatgta atcatgttca atagcttttgt gatttttttttc cttggtctttt gccatcaaca    5820
atttcctattt aacatatagt tgtttctcat tggttaatat ttggattggc tcttttttttg    5880
tcaagcatta ttggtatttc aattttttagt tctagataaa attttttattt ttcatcattg    5940
tacaggccgt tgctctttta attgccttcc tggtttctgc tttattccat gaggtgtgtt    6000
gctcatctct ctgtacagcc ttctctcttc tttttttttgt attatgtcat tatggttgtt    6060
ctgcttgagt gtttgtctgc atcctacact gattgaagtc aaactgtatc ttgcaattaa    6120
tatatttttg gagtatcctt tcctccttttt ccttgggctg tttggactttt gctaagagtt    6180
agatagaagg gaagggaaaa ttagttacag atggttagag tagttgatta gtcagttata    6240
ggatttggtt agatattaat tacggggatt aagaggaaag gatccattct atctagttga    6300
ttagtcagtt ataggatcca ttctatctag tatcatttga gaattgagct tggctctttt    6360
gaaaggagaa atcctttgtg aggggaaac ccttggagga gaattatctc ttctttttttc    6420
tgttctagat gataaaactg cccttttatt tcttctttttg ctttgggttc gtaacagact    6480
gtgggagagg actgaaaatt agatactaag ttgtggctga tttgttaaaa attggtatag    6540
gacccatgct acttgtcttt gaactatcta caacccacta tgccccaga aacctctaggc    6600
agctagctac caaatctgt agtaacttgc agcctgtctg tctgtacctt ggcaggtgta    6660
gatgttacag cttccatatc ttatatctta aatatagact gacataacaa ttatgacaaa    6720
ctgttatatt ttcctagttgc tagttcttgc aatattaatt ttggcaccaa aatttcccta    6780
catgtactca aggatgctta cttttagccat gaataatttt ttttttcacg tgttgtaatt    6840
atattttcaa tttatcctgt catttttttcc tgaaaaggt acatacacag aataatttga    6900
taacttaagg tggcgcttgg tttgagtgtt ttgtgttttc attttcaaag aaaatagaaa    6960
ataagagtga aaatatgttt gcctaaaatt tagaaaacat tttctatgaa aatatttcaa    7020
aaacaagccc aaaactgaaa acaaccaata aactttttca gccttttttct gaagaagtga    7080
aaacacgatg tcactttaga gtactttctt ccaaaacac gttttctaaa tctgaaaat    7140
ctgaaaatga aataaaaat tattttgaga aaatgaaaaa gaaaatttaaa cattcaaatc    7200
aaacgccacc ttaattgtca tagacagttg tgcaattttttt ctcacgatat ctctttcgtc    7260
tgagtgcagc tgtgcatcgc tgttccttgc cacatattca agttgtgggc tttcggtgga    7320
attatgtttc aggtaaaatc aaattaccgc actaaacttt tgttttccca tcttctatta    7380
ttaaactaaa gcatttttaat tcagagtaag agtaacacga attttccaag aaaccaaact    7440
tctcccctct tccctcacga agaaggtgaa ggattgccga gatttttttt tcctgttctt    7500
```

```
ttatggccaa acgatagaaa gtattctctg gaataatgaa tttgtgccat gtttgaaagt   7560
tgatgattat gatatcatcc atcttttggg ttcaattaac atgataagga atgacttttt   7620
tctaggttcc tttggtcttc atcactaatt atctgcaaaa taaattcaga aactcgatgg   7680
tacgtctgct atttaagcat attgattcat aatatatctt attactccat catcttgaat   7740
ttgattcatt ggttttttaa tttgttttttg tcttcatgcc aggttggaaa tatgattttt   7800
tggttcatat tcagtattct tggtcaacct atgtgcgtac tgctatatta ccatgactta   7860
atgaatagga aaggcaaact tgactgaagg tgcacgtgga taagcttttc tgttttttgga  7920
gtgtataatt gatgtcgata tgttgatcaa tattgttttc cacgagtact ttcatctacc   7980
atggcagtgg ctgctctgaa ggatttccac ctgatatacc aggtcgcgag gctaattcat   8040
cttgatctat gtacttatca actctcctct ggcaattgta tcgatatatg caattttgag   8100
agccatacac tggcattgat aactgccaag gaacagtgta gctgtttttct gttaaatgtt   8160
aattagtaga gagctagatg taaataattt atgctcaata tatttatttc ttcctattct   8220
tcaagttcca cggatgaatg atg                                            8243
```

```
SEQ ID NO: 31              moltype = DNA   length = 20
FEATURE                    Location/Qualifiers
misc_feature               1..20
                           note = GM-DGAT-CR1 (synthesized almost complement of native
                            sequence)
source                     1..20
                           mol_type = other DNA
                           organism = synthetic construct
SEQUENCE: 31
ggaattgaag aggccagcgg                                                20

SEQ ID NO: 32              moltype = DNA   length = 20
FEATURE                    Location/Qualifiers
misc_feature               1..20
                           note = GM-DGAT-CR3 (synthesized almost complement of native
                            sequence)
source                     1..20
                           mol_type = other DNA
                           organism = synthetic construct
SEQUENCE: 32
gcggcggtgg aggtggcgga                                                20

SEQ ID NO: 33              moltype = DNA   length = 20
FEATURE                    Location/Qualifiers
misc_feature               1..20
                           note = GM-DGAT-CR4 (synthesized almost complement of native
                            sequence)
source                     1..20
                           mol_type = other DNA
                           organism = synthetic construct
SEQUENCE: 33
ggacagttcc ggtgatgact                                                20

SEQ ID NO: 34              moltype = DNA   length = 25
FEATURE                    Location/Qualifiers
misc_feature               1..25
                           note = DGAT1a primer
source                     1..25
                           mol_type = other DNA
                           organism = synthetic construct
SEQUENCE: 34
agactgagtt agtaaacacg ctcgc                                          25

SEQ ID NO: 35              moltype = DNA   length = 25
FEATURE                    Location/Qualifiers
misc_feature               1..25
                           note = DGAT1a primer
source                     1..25
                           mol_type = other DNA
                           organism = synthetic construct
SEQUENCE: 35
tacgagtcgc ttgcattcat gagtc                                          25

SEQ ID NO: 36              moltype = DNA   length = 25
FEATURE                    Location/Qualifiers
misc_feature               1..25
                           note = DGAT1b primer
source                     1..25
                           mol_type = other DNA
                           organism = synthetic construct
SEQUENCE: 36
agactgagtt agaaaacacg ctcgg                                          25

SEQ ID NO: 37              moltype = DNA   length = 30
FEATURE                    Location/Qualifiers
```

```
misc_feature            1..30
                        note = DGAT1b primer
source                  1..30
                        mol_type = other DNA
                        organism = synthetic construct
SEQUENCE: 37
tttctagtac acataaatta aataaacaag                                              30

SEQ ID NO: 38           moltype = AA  length = 7
FEATURE                 Location/Qualifiers
REGION                  1..7
                        note = Glycine max derived peptide
source                  1..7
                        mol_type = protein
                        organism = synthetic construct
SEQUENCE: 38
APTLCYQ                                                                        7

SEQ ID NO: 39           moltype = AA  length = 13
FEATURE                 Location/Qualifiers
REGION                  1..13
                        note = Glycine max derived peptide
source                  1..13
                        mol_type = protein
                        organism = synthetic construct
SEQUENCE: 39
FGDREFYXDW WNA                                                                13

SEQ ID NO: 40           moltype = AA  length = 6
FEATURE                 Location/Qualifiers
REGION                  1..6
                        note = Glycine max derived peptide
source                  1..6
                        mol_type = protein
                        organism = synthetic construct
SEQUENCE: 40
LLYYHD                                                                         6

SEQ ID NO: 41           moltype = AA  length = 44
FEATURE                 Location/Qualifiers
REGION                  1..44
                        note = Glycine max derived peptide
source                  1..44
                        mol_type = protein
                        organism = synthetic construct
SEQUENCE: 41
ESPLSSDXIF XQSHAGLXNL CXVVLXAVNX RLIIENLMKY GXLI                               44

SEQ ID NO: 42           moltype = AA  length = 19
FEATURE                 Location/Qualifiers
REGION                  1..19
                        note = Glycine max derived peptide
source                  1..19
                        mol_type = protein
                        organism = synthetic construct
SEQUENCE: 42
GFIIEQYINP IVXNSXHPL                                                          19
```

MODIFIED SEED OIL CONTENT BY GENE EDITING

CROSS-REFERENCE TO RELATED APPLICATIONS

This application is a continuation of U.S. patent application Ser. No. 17/057,056, which is a national stage application of PCT/US19/34606 filed May 30, 2019, which claims the benefit of priority to U.S. Provisional Application Nos. 62/679,116 filed on Jun. 1, 2018 and 62/796,847 filed on Jan. 25, 2019, each of which is incorporated herein by reference in its entirety.

REFERENCE TO SEQUENCE LISTING SUBMITTED ELECTRONICALLY

The official copy of the sequence listing is submitted electronically via Patent Center as an XML formatted sequence listing with a file named 7776-US-PCN Sequence-Listing created on Feb. 3, 2023 and having a size of 88,077 bytes and is filed concurrently with the specification. The sequence listing contained in this XML formatted document is part of the specification and is herein incorporated by reference in its entirety.

BACKGROUND

Plant oils are a major product of oil seed crops such as soybean, sunflower and canola. Oils, such as soybean oil, produced in the US are extracted from seeds and have a major use in food products such as cooking oils, shortenings and margarines. The oils can be refined, bleached and deodorized (RBD) and may be hydrogenated to facilitate use in shortenings. Plant genetic engineering has facilitated the engineering of plants to have improved seed composition, such as improved oils and fatty acid content.

SUMMARY

Provided are modified polynucleotides encoding a diacylglycerol acyltransferase-1 (DGAT1) polypeptide having a deletion of at least 1 and less than 107 amino acids in the N-terminal region corresponding to the region at positions 1 to 107 of SEQ ID NO: 2. The DGAT1 polypeptide can have increased stability, increased activity or effect an increase in fatty acid or fatty acid and protein content when expressed in a plant cell. Also provided are modified polynucleotides comprising, either in combination with an N-terminal deletion or without a N-terminal deletion, at least one amino acid substitution selected from a substitution at the position corresponding to position 24, 34, 58, 181, 210, 216, 244, 258, 264, 328, 355, 364, 387, 440, 467, 473 or 479, or any combination thereof of SEQ ID NO:2. The modified polynucleotides may share at least about 40%, 45%, 50%, 55%, 60%, 65%, 70%, 75%, 80%, 85%, 90%, 95%, 96%, 97%, 98% or 99% identity to the corresponding genomic sequences, such as SEQ ID NO: 29 or 30. The deletion can represent a sequence encoding a polypeptide of at least or at least about 1, 2, 3, 4, 5, 6, 7, 8 ,9, 10, 11, 12, 13, 14, 15, 16, 17, 18, 19, 20, 25, 30, 35, 40, 45, 50, 55, 60, 65, 70, 75, 80, 85, 90, 95, or 100 amino acids, and less than or less than about 107, 106, 105, 100, 95, 90, 85, 80, 75, 70, 65, 60, 55, 50, 45, 40, 35, 30, 25, 20, 15, 10, 9, 8, 7, 6, 5, 4, 3 or 2 amino acids. The deletion can occur in a sequence encoding a polypeptide corresponding to SEQ ID NO: 2 at positions corresponding to position 1 to position 108 of SEQ ID NO: 2. The modified polynucleotide may encode a polypeptide having at least 70%, 75%, 80%, 85%, 90%, or 95% identity to positions 108 to 504 of SEQ ID NO: 2. The deletion can include a deletion corresponding to the N-terminal region of the coding sequence or encoded polypeptide of at least or at least about 1, 2, 3, 4, 5, 6, 7, 8 ,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 49, 50, 51, 52, 53, 55, 55, 56, 57, 58, 59, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, 265, 270, 280, 290, or 300 nucleotides and less than or less than about 321, 320, 310, 300, 290, 280, 270, 260, 250, 240, 230, 220, 210, 200, 190, 180, 170, 160, 150, 145, 140, 135, 130, 125, 120, 115, 110, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 nucleotides, for example the deletion can occur in a location corresponding to from position 1 to position 321 of SEQ ID NO: 1.

The modified polynucleotides can encode polypeptides which comprise one or more or all three signature motifs such as APTLCYQ (SEQ ID NO: 38, corresponding to position 274-280 of SEQ ID NO: 2), FGDREFYXDWWNA (SEQ ID NO: 39; corresponding to position 370-382 of SEQ ID NO: 2) and LLYYHD (SEQ ID NO: 40; position 390-395 of SEQ ID NO: 2), where X is any amino acid, such as K or Q. Other amino acid motifs in the polypeptides disclosed herein and polynucleotides encoding them include, for example, GFIIEQYINPIVXNSXHPL (SEQ ID NO: 41; corresponding to position 309-327 of SEQ ID NO: 2) and ESPLSSDXIFXQSHAGLXNLCXVVLXAVNXR-LIIENLMKYGXLI (SEQ ID NO: 42; corresponding to position 95-138 of SEQ ID NO: 2), wherein X is any amino acid. The polypeptides may include at least 1, 2, 3, 4 or 5 amino acid motifs disclosed herein, and any combination thereof. Such polynucleotides may encode polypeptides having at least about 50%, 55%, 60%, 70%, 75%, 80%, 85%, 90%, or 95% identity to SEQ ID NO:2 and comprise one or more of the motifs disclosed herein.

Plant cells, seed cells, soybean cells and soybean plants and seeds containing the modified polynucleotides and polypeptides disclosed herein are provided. The cells, seeds and plants can show increased fatty acid content when compared to a cell, seed or plant comprising a comparable polynucleotide which lacks the modification. Modified polypeptides encoded by the polynucleotides are also provided.

The increase in fatty acid content in the cell or seed containing or expressing the modified polynucleotides or polypeptides disclosed herein can be an increase of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45% or 50% relative to the fatty acid content of a cell or seed expressing the polypeptide without the modifications. The increase in fatty acid content in the cell or seed can be an increase of at least at least 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, or 8.0 percentage points and less than about 10.0, 9.5, 9.0, 8.5, 8.0, 7.5, 7.0, 6.5, 6.0, 5.5, 5.0 or 4.5 percentage points by weight of the cell relative to control.

The increase in protein content in the cell or seed containing or expressing the modified polynucleotides or polypeptides disclosed herein can be an increase of at least 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.5%, 4.0%, 4.5% or 5.0% relative to the protein content of a cell or seed expressing the polypeptide without the modifications. The increase in protein content in the cell or seed can be an increase of at least at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2.0 percentage points and less than about 5.0, 4.5, 4.0, 3.5, 3.0, 2.5, 2.0, or 1.5 percentage points by weight of the cell relative to control.

In some embodiments, a modified polynucleotide encoding a polypeptide having at least 90% identity to SEQ ID NO:2 and at least 70% identity to SEQ ID NO:29 is provided which comprises one or more modifications selected from a non-serine at the position corresponding to position 24 of SEQ ID NO:2, a non-serine at the position corresponding to position 34 of SEQ ID NO:2, a non-serine at the position corresponding to position 58 of SEQ ID NO:2; a non-proline at the position corresponding to position 181 of SEQ ID NO:2, a non-alanine at the position corresponding to position 210 of SEQ ID NO:2, a non-threonine at the position corresponding to position 216 of SEQ ID NO:2, a non-aspartic acid at the position corresponding to position 258 of SEQ ID NO:2, a non-serine at the position corresponding to position 264 of SEQ ID NO:2, a non-lysine at the position corresponding to position 328 of SEQ ID NO:2, a non-aspartic acid at the position corresponding to position 364 of SEQ ID NO:2, a non-aspartic acid at the position corresponding to position 387 of SEQ ID NO:2, a non-isoleucine at the position corresponding to position 440 of SEQ ID NO:2, a non-arginine at the position corresponding to position 467 of SEQ ID NO:2, and a non-isoleucine at the position corresponding to position 479 of SEQ ID NO:2. When expressed in a plant cell, the polynucleotide can increase the fatty acid content of the plant cell compared to a plant cell comprising a comparable polynucleotide without the modification.

Methods of producing a plant cell having increased oil content, by transforming a plant cell with the modified polynucleotides disclosed herein are provided. The plant cell can have increased oil content, protein content or a combination thereof, compared with a cell not comprising the modified polynucleotide. The polypeptides produced by the polynucleotides can show increased activity and/or stability when expressed in the cell. The cell can be a soybean cell, such as a soybean seed cell. Plants regenerated from the cell may produce seeds having an increase fatty acid and/or protein content.

Modified DGAT1 polynucleotides encoding a polypeptide having at least 60%, 65%, 70%, 75%, 80%, 85%, 90%, 95%, 96%, 97%, 98%, or 99% identity from position 108 to 504 of SEQ ID NO: 2 are provided which contain a deletion of 1 to 105 amino acids from position 1 to position 107 of SEQ ID NO: 2 and have at least one amino acid substitution selected from a non-serine at the position corresponding to position 24 of SEQ ID NO:2, a non-serine at the position corresponding to position 34 of SEQ ID NO:2, a non-serine at the position corresponding to position 58 of SEQ ID NO:2; a non-proline at the position corresponding to position 181 of SEQ ID NO:2, a non-alanine at the position corresponding to position 210 of SEQ ID NO:2, a non-threonine at the position corresponding to position 216 of SEQ ID NO:2, a non-lysine acid at the position corresponding to position 244 of SEQ ID NO:2, a non-aspartic acid at the position corresponding to position 258 of SEQ ID NO:2, a non-serine at the position corresponding to position 264 of SEQ ID NO:2, a non-lysine at the position corresponding to position 328 of SEQ ID NO:2, a non-cysteine at the position corresponding to position 355 of SEQ ID NO:2, a non-aspartic acid at the position corresponding to position 364 of SEQ ID NO:2, a non-aspartic acid at the position corresponding to position 387 of SEQ ID NO:2, a non-isoleucine at the position corresponding to position 440 of SEQ ID NO:2, a non-arginine at the position corresponding to position 467 of SEQ ID NO:2, a non-isoleucine at the position corresponding to position 473 of SEQ ID NO:2, and a non-isoleucine at the position corresponding to position 479 of SEQ ID NO:2. When expressed in a soybean plant cell the modified polynucleotides can increase oil content of the soybean plant cell. The polypeptide encoded by the polynucleotide can include one or more or all three substitutions selected from a non-cysteine at position 355 of SEQ ID NO: 2, a non-arginine at position 473 of SEQ ID NO: 2, and a non-isoleucine at position 479 of SEQ ID NO: 2. The polypeptide substitutions can be a serine at position 355 of SEQ ID NO: 2, a serine at position 473 of SEQ ID NO: 2, and/or a serine at position 479 of SEQ ID NO: 2. The polypeptide encoded by the polynucleotide can include one or both of an amino acid substitution, such as a serine, at the position corresponding to position 258 of SEQ ID NO:2 and an amino acid substitution, such as an aspartate at the position corresponding to position 479 of SEQ ID NO:2.

The polypeptide encoded by the polynucleotide can include an amino acid substitution selected from one or more or all four of the following: an amino acid substitution, such as threonine, at the position corresponding to position 216 of SEQ ID NO:2, an amino acid substitution, such as aspartate, at the position corresponding to position 258 of SEQ ID NO:2, an amino acid substitution, such as serine, at the position corresponding to position 264 of SEQ ID NO:2 and an amino acid substitution, such as an aspartate, at the position corresponding to position 479 of SEQ ID NO:2.

In plant cells, seeds, soybean cells and soybean seeds expressing the modified polynucleotides, the oil content can be increased by at least 5%, 10%, 15% or 20% compared to a comparable cell or seed expressing the polynucleotide without the modification.

Methods of producing a soybean seed are provided which include the steps of sexually crossing a first soybean line comprising a polynucleotide disclosed herein, with a second soybean line not comprising the polynucleotide and harvesting the seed produced from the cross. The method can include a further step of backcrossing a second generation progeny plant produced from the seed that comprises the polynucleotide to the parent plant that lacks the polynucleotide, to produce a backcross progeny plant that produces seed with increased fatty acid content.

Methods of screening for the presence or absence of the modified polynucleotides disclosed herein in a plurality of genomic soybean DNA samples are provided, which include the steps of contacting a plurality of genomic soybean DNA samples, at least some of which comprise the polynucleotides, with a first DNA primer molecule and a second DNA primer molecule; providing nucleic acid amplification reaction conditions and performing the nucleic acid amplification reactions, to produce a DNA amplicon molecule indicating the presence of the polynucleotide or a wild-type DGAT1 nucleotide sequence and detecting the DNA amplicon molecules, wherein the presence, absence or size of the DNA amplicon molecule indicates the presence or absence of the polynucleotide in the at least one of the plurality of genomic soybean DNA samples.

BRIEF DESCRIPTION OF THE DRAWINGS AND SEQUENCE LISTING

The disclosure can be more fully understood from the following detailed description and the accompanying drawings and Sequence Listing that form a part of this application, which are incorporated herein by reference.

FIG. 1 is a graph showing DGAT protein level in tobacco leaf with expression of DGAT variants. DGAT1b mod is soybean DGAT1b with 14 amino acid substitutions (SEQ ID NO:26). A significant difference between DGAT variant and wild type DGAT at P<0.05 was found in the four DGAT variants. A significant difference between DGAT variant and wild type DGAT at P<0.05 is marked with asterisks.

Figure 2:
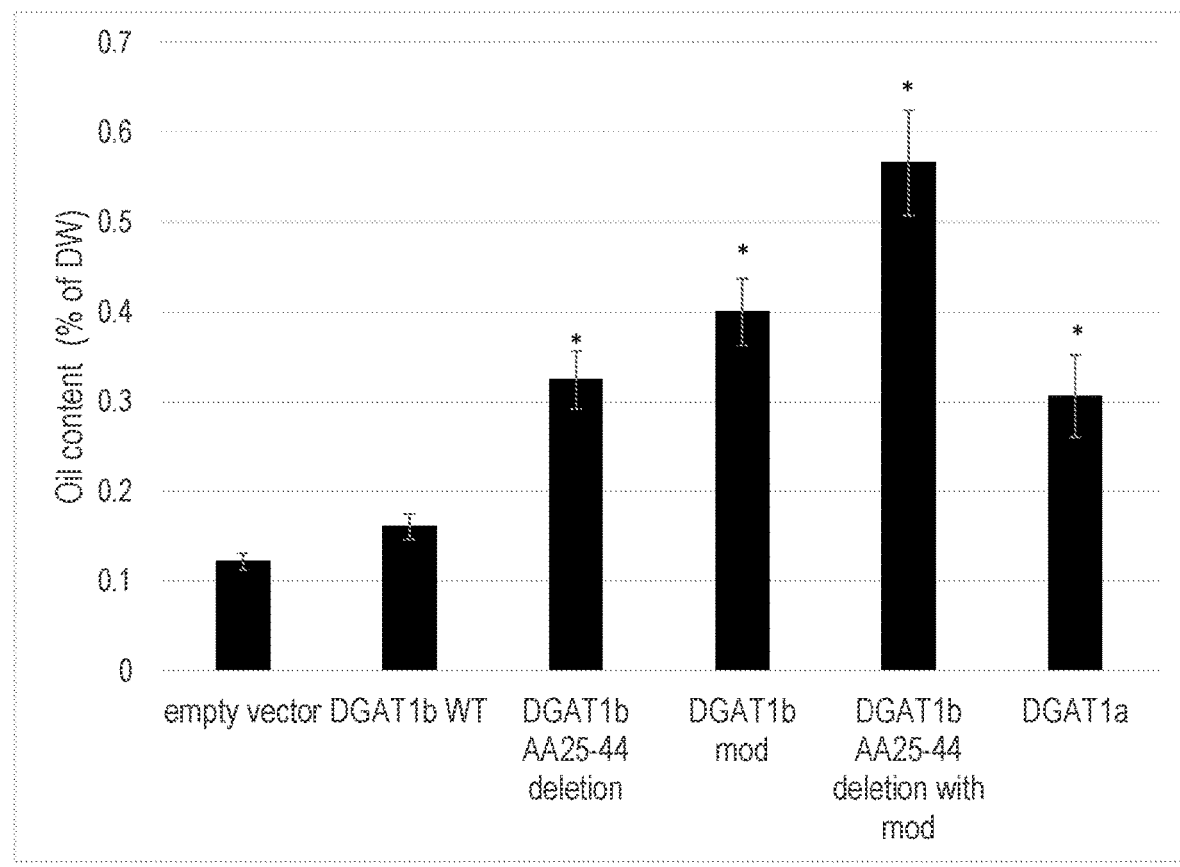

FIG. 2 is a graph showing the oil content in tobacco leaf expressing different DGAT variants. DGAT1b mod is soybean DGAT1b with 14 amino acid substitutions (SEQ ID NO:26). A significant difference between DGAT variant and wild type DGAT at P<0.05 was found in the four DGAT variants. A significant difference between DGAT variant and wild type DGAT at P<0.05 is marked with asterisks.

Figure 3:
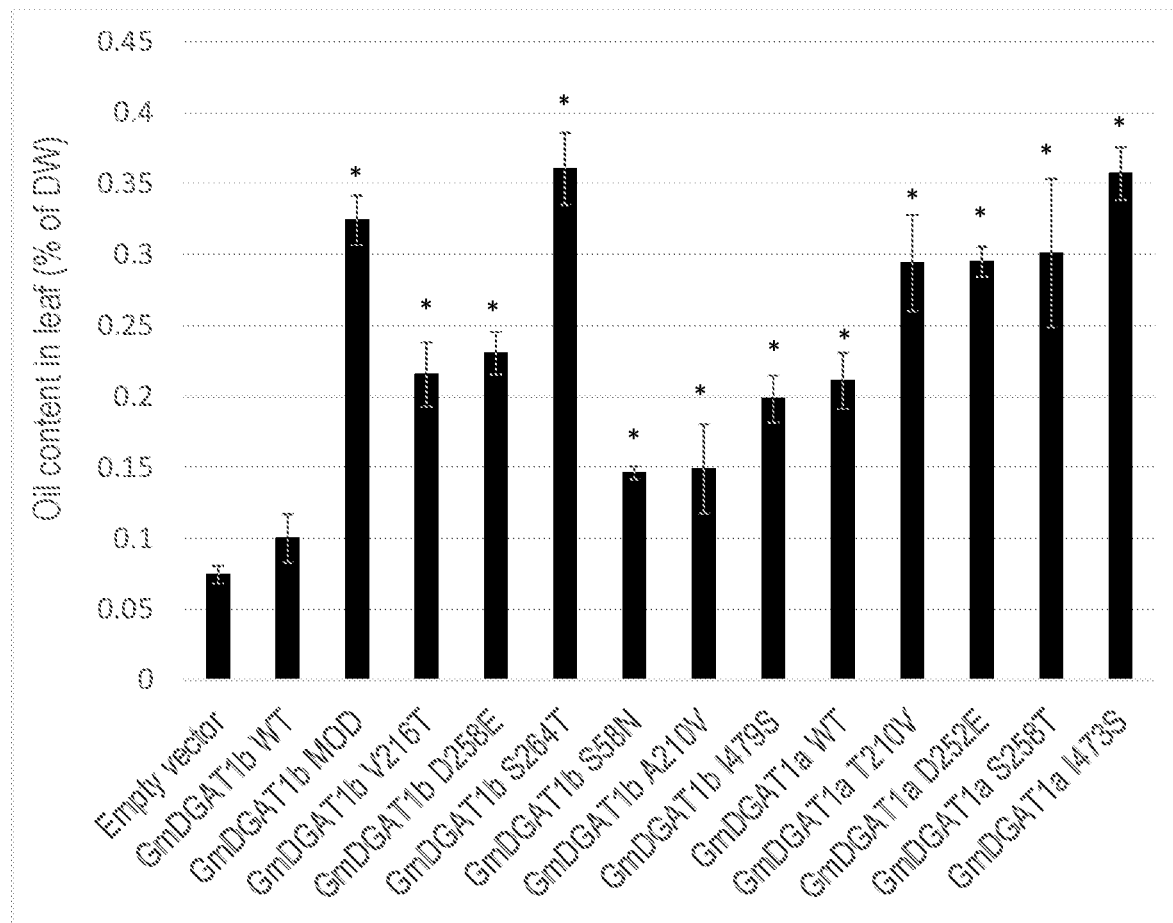

FIG. 3. is a graph showing the oil content in tobacco leaf tobacco leaf expressing different DGAT variants. A single amino acid substitution in GmDGAT1a and GmDGAT1b increases oil content in tobacco leaf transient expression. GmDGAT1b mod is soybean DGAT1b with 14 amino acid substitutions (SEQ ID NO:26). A significant difference between DGAT variant and wild type DGAT at P<0.05 was found in the twelve DGAT variants.

FIG. 4A-D is a sequence alignment of plant DGAT amino acid sequences with the amino acid substitutions which correspond to the positions described herein marked with stars.

Figure 5:
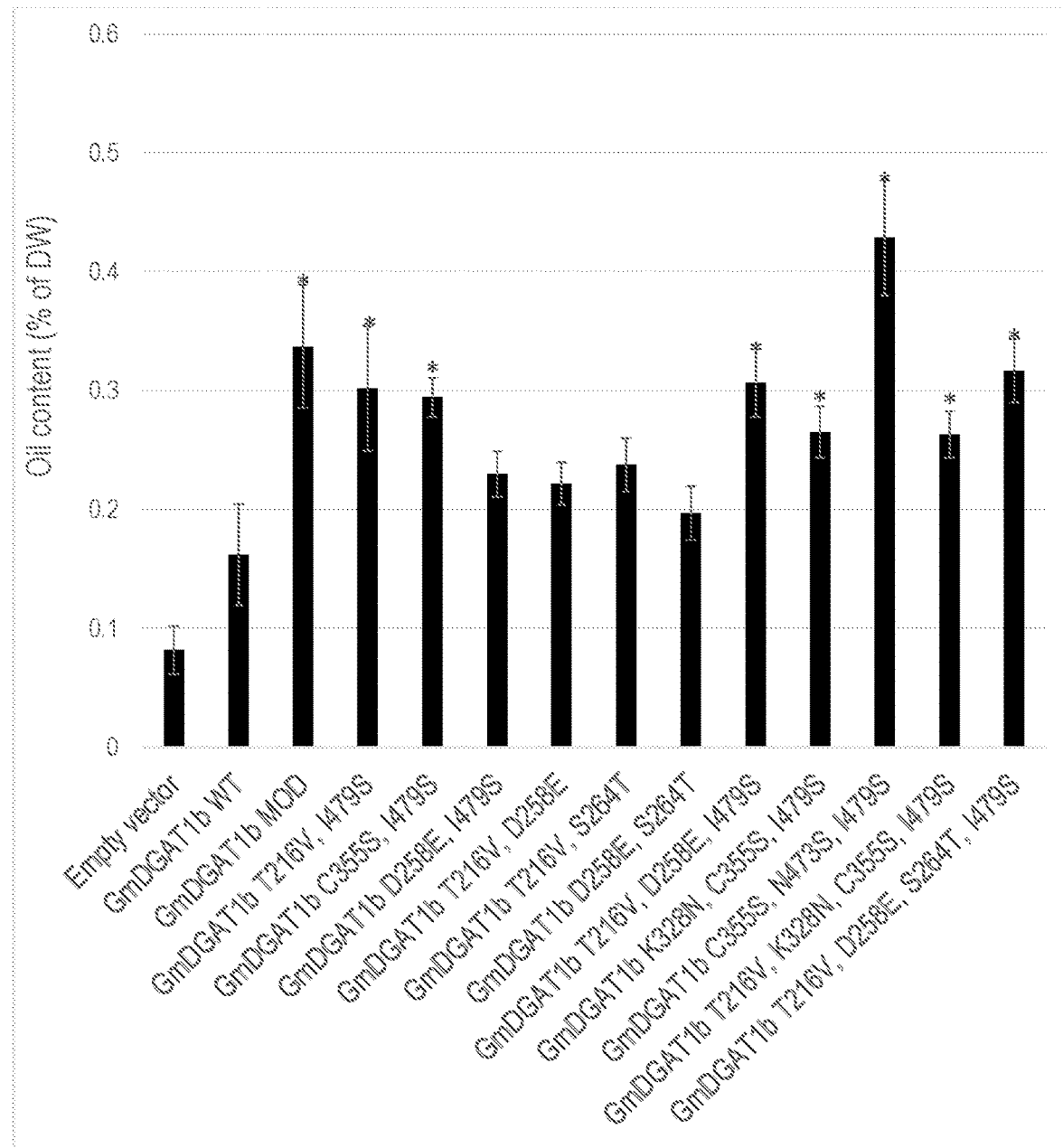

FIG. 5 is a graph showing the oil content in tobacco leaf expressing different DGAT variants. Changes of two to four amino acids in DGAT increases oil content in tobacco leaf transient expression. GmDGAT1b mod is soybean DGAT1b with 14 amino acid substitutions (SEQ ID NO:26). A significant difference between DGAT variant and wild type DGAT at P<0.05 was found in the 8 (marked with asterisks) of the 12 DGAT variants.

Figure 6:
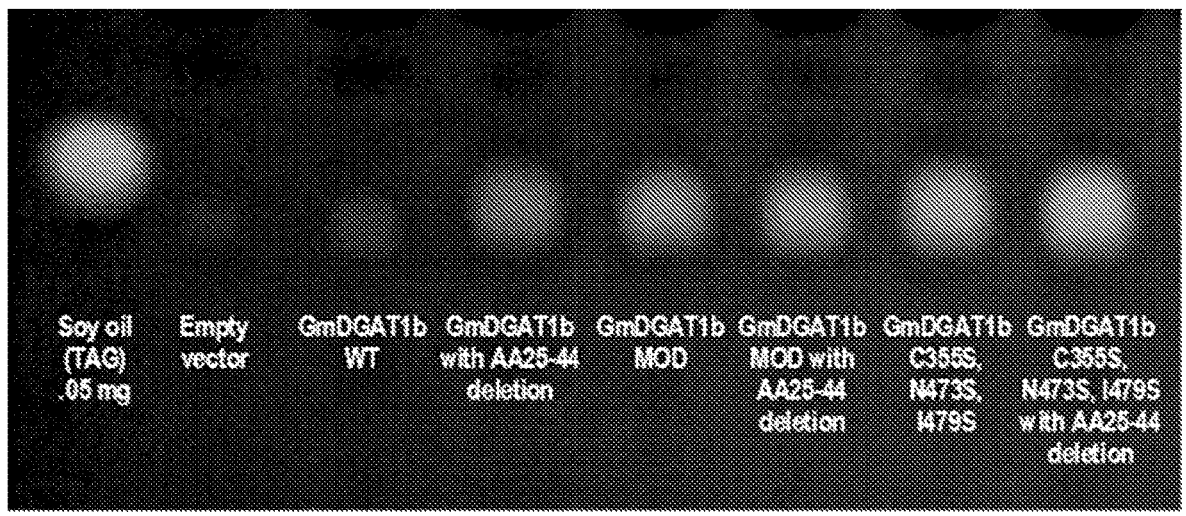

FIG. 6 is a photograph showing the oil content in tobacco leaf expressing different DGAT variants. The combination of 3 amino acid substitutions with N-terminal deletion at AA25-44 increases oil more than either 3 amino acid substitution or the N-terminal deletion at AA25-44 alone and is higher than GmDGAT1b mod with 14 amino acid substitutions (SEQ ID NO:26).

The sequence descriptions summarize the Sequence Listing attached hereto. The Sequence Listing contains one letter codes for nucleotide sequence characters and the single and three letter codes for amino acids as defined in the IUPAC IUB standards described in Nucleic Acids Research 13:3021 3030 (1985) and in Biochem. J. 219(2):345 373 (1984).

Figure 7:
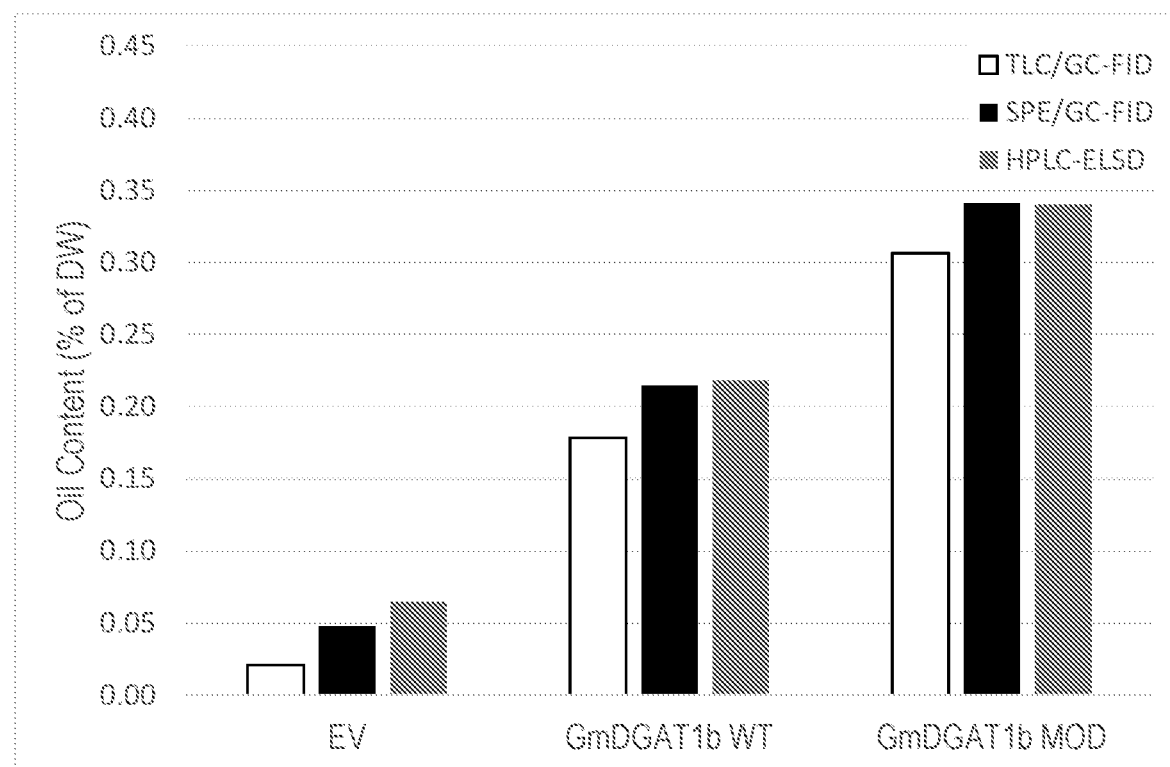

FIG. 7 is a graph showing the oil content from GmDGAT1b wild type (SEQ ID NO:2), GmDGAT1b mod (SEQ ID NO:2), and empty vector expressed in tobacco leaf and compare three different TAG isolation and quantification procedures, including TLC/GC-FID, SPE/GC-FID, and HPLC-ELSD. Samples were analyzed with each of the three analysis methods. GmDGAT1b mod is soybean DGAT1b with 14 amino acid substitutions (SEQ ID NO:26).

Figure 8:
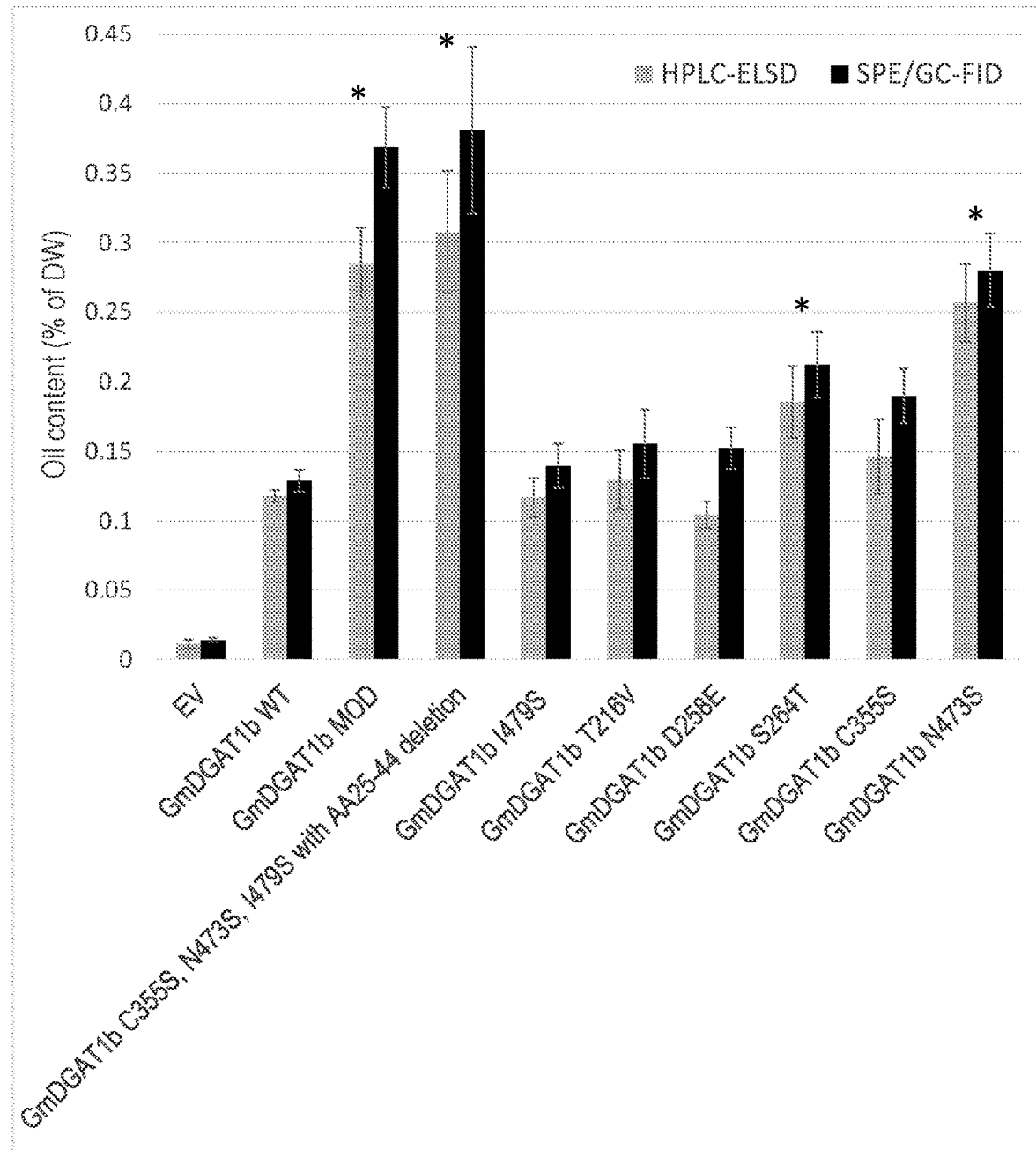

FIG. 8 is a graph showing the oil content in tobacco leaf expressing additional DGAT1 variants analyzed with the HPLC-ELSD and SPE/GC-FID procedures. Single amino acid substitutions in GmDGAT1b increases oil content in tobacco leaf transient expression system. GmDGAT1b mod is soybean DGAT1b with 14 amino acid substitutions (SEQ ID NO:26). A significant difference between DGAT variants and wild type DGAT at p<0.05 was found in the 4 (marked with an asterisks) of the 8 DGAT variants.

Figure 9:
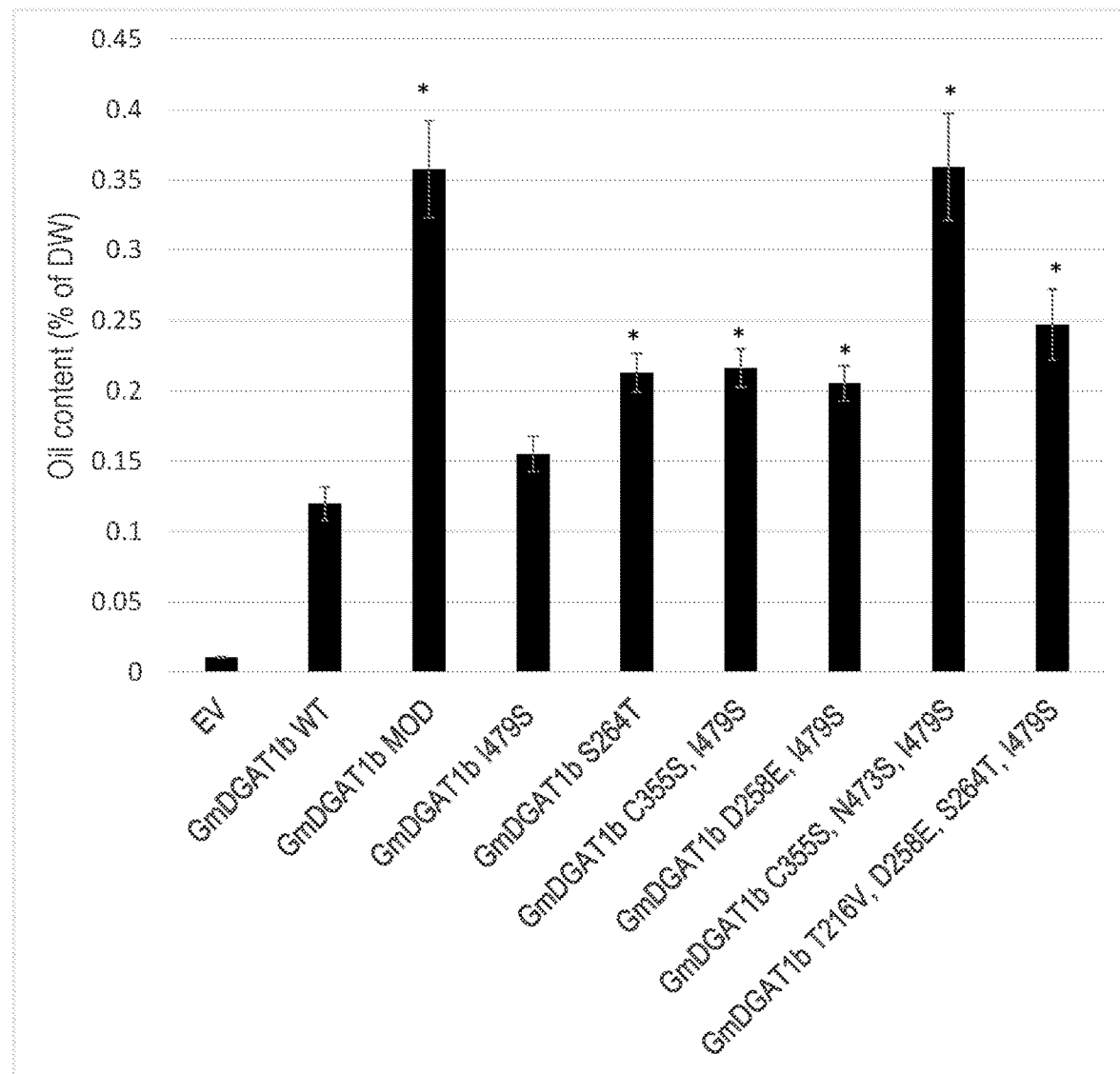

FIG. 9 is a graph showing the oil content in tobacco leaf expressing different DGAT variants analyzed with the SPE/GC-FID procedure. Changes of one to four amino acids in DGAT increases oil content in tobacco leaf transient expression. GmDGAT1b mod is soybean DGAT1b with 14 amino acid substitutions (SEQ ID NO:26). A significant difference between DGAT variants and wild type DGAT at p<0.05 was found in the 6 (marked with asterisks) of the 7 DGAT variants.

Figure 10:
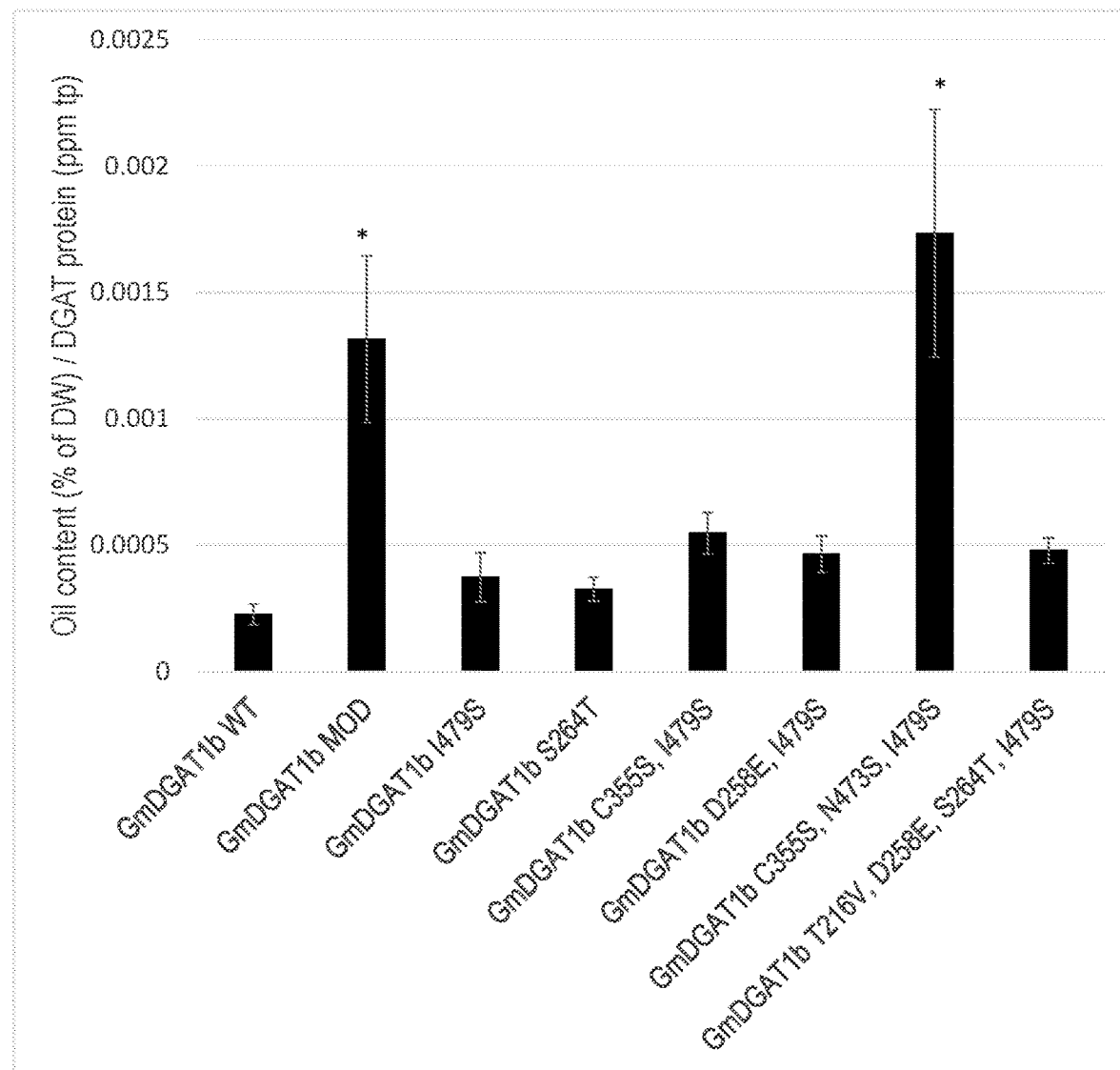

FIG. 10 is a graph showing the oil/protein ratio in tobacco leaf expressing different DGAT variants from FIG. 9. GmDGAT1b mod is soybean DGAT1b with 14 amino acid substitutions (SEQ ID NO:26). A significant difference between DGAT variants and wild type DGAT at p<0.05 was found in the 2 (marked with asterisks) of the 7 DGAT variants.

TABLE 1

List of sequences used in this application

| Sequence | Nucleotide SEQ ID NO: | Polypeptide SEQ ID NO: |
|---|---|---|
| Glycine max GmDGAT1b | 1 | 2 |
| Glycine max GmDGAT1a | 3 | 4 |
| Glycine max GmDGAT1C | 5 | 6 |
| Brassica napus BnDGAT1a | 7 | 8 |
| Gossypium hirsutum GhDGAT1 | 9 | 10 |
| Helianthus annuus HaDGAT1 | 11 | 12 |
| Hordeum vulgare DGAT1 | 13 | 14 |
| Oryza sativa DGAT1 | 15 | 16 |
| Sorghum bicolor DGAT1b | 17 | 18 |
| Triticum aestivum DGAT1 | 19 | 20 |
| Zea mays DGAT1-2 | 21 | 22 |
| Elaeis guineensis DGAT1-1 | 23 | 24 |
| Glycine max GmDGAT1a with 48 bp deletion | 25 | |
| Glycine max GmDGAT1B with 60 bp deletion | 26 | |
| Glycine max GmDGAT1b mod | | 27 |
| Glycine max GmDGAT1a mod | | 28 |
| Glycine max GmDGAT1b genomic | 29 | |
| Glycine max GmDGAT1a genomic | 30 | |
| GM-DGAT-CR1 | 31 | |
| GM-DGAT-CR3 | 32 | |
| GM-DGAT-CR4 | 33 | |
| DGAT1a WOL1469 | 34 | |
| DGAT1a WOL1470 primer | 35 | |
| DGAT1b WOL1471 primer | 36 | |
| DGAT1b WOL1472 primer | 37 | |
| DGAT polypeptide motif | | 38 |
| DGAT polypeptide motif | | 39 |
| DGAT polypeptide motif | | 40 |
| DGAT polypeptide motif | | 41 |
| DGAT polypeptide motif | | 42 |

DETAILED DESCRIPTION

Compositions and methods related to modified plants, such as soybean plants, producing seeds high in oil are provided. The seeds may also have increased amounts of protein. Suitable plants include oil-seed plants, such as palm, canola, sunflower and soybean as well as, without limitation, rice, cotton, sorghum, wheat, maize, alfalfa and barley. Plants, such as soybean plants, that have been modified using genomic editing techniques to produce seeds having a desirable fatty acid content are provided. The inventors found that providing particular amino acid substitutions, or combinations of amino acid substitutions, as well as particular deletions in diacylglycerol acyltransferase (DGAT) alleles using genomic editing technology as described herein provided a DGAT protein with higher activity and increased stability. Plant cells containing the modified DGAT sequences show increased fatty acid or oil content.

The modified sequences, plants, seeds and cells disclosed herein are produced by genomic editing techniques which facilitate the editing of the DGAT alleles, such as provided in SEQ ID NOs: 1-30. The sense strand or the complement thereof may be edited.

A "DGAT", "DGAT1", "DGAT1a" or "DGAT1b" or a "DGAT-modified plant", "DGAT1-modified plant", "DGAT1a-modified plant" or "DGAT1b-modified plant" generally refers to a modified or mutant plant or plant cell that has one or more nucleotide changes or deletions in a genomic region that encodes a polypeptide that is at least 70%, 75%, 80%, 85%, 90%, 95%, 96%, 97%, 98% or 99% identical to one of SEQ ID NOS: 1-24 or an allelic variant thereof. DGAT1a and DGAT1b may also be written as DGAT1A and DGAT1B, respectively. The nucleotide changes in the sequences encoding a DGAT polypeptide disclosed herein can include modifications that result in one or more amino acid substitutions at an amino acid corresponding to those listed in Table 2, either alone or in any combination. Amino acids corresponding to those listed in Table 2, for example, are shown with an asterisk in FIG. 4. The modified DGAT sequences when expressed in cells, plants and seeds may show an increase in oil and may be more stable, show an increase in specific activity or any combination thereof. An increase in protein and fatty acid content in the plant cell or in a seed comprising the plant cell may also result from expression of the modified polynucleotides disclosed herein. The polynucleotides may also have at least about 40%, 45%, 50%, 55%, 60%, 65%, 70%, 75%, 80%, 85%, 90%, 95%, 96%, 97%, 98% or 99% identity, such as according to parameters disclosed herein, to their corresponding genomic nucleotide sequence, such as SEQ ID NO: 29 or 30.

TABLE 2

Positions for amino acid substitutions in DGAT sequences

| GmDGAT1B (SEQ ID NO: 2) Soy | GmDGAT1a (SEQ ID NO: 4) Soy | GmDGAT1C (SEQ ID NO: 6) Soy | BnDGAT1a (SEQ ID NO: 8) Canola | GhDGAT1 (SEQ ID NO: 10) Cotton | HaDGAT1 (SEQ ID NO: 12) Sunflower | HvDGAT1 (SEQ ID NO: 14) Barley |
|---|---|---|---|---|---|---|
| S58 | S55 | D71 | E64 | D63 | A68 | — |
| P181 | P175 | S194 | S188 | S186 | S194 | R147 |
| A210 | A204 | A233 | A217 | A215 | V223 | A176 |
| T216 | T210 | T229 | T223 | A221 | S229 | V182 |
| D258 | D252 | E271 | E258 | — | E271 | E224 |
| S264 | S258 | T277 | S264 | S262 | D277 | T230 |
| K328 | K322 | K341 | K328 | K326 | N341 | K294 |
| L364 | L358 | L377 | L364 | L362 | L377 | L330 |
| D387 | D381 | E400 | D387 | E385 | E400 | E353 |
| I440 | I434 | M453 | L438 | L438 | I453 | I406 |
| R467 | R461 | R480 | — | Q465 | Q480 | K433 |
| I479 | I473 | I492 | A478 | I477 | F492 | F445 |
| S24 | T24 | S32 | S30 | D26 | S24 | A23 |
| S34 | S31 | D42 | D40 | A36 | S44 | — |
| L244 | S238 | S257 | S251 | S249 | S257 | S210 |
| C355 | C349 | C368 | C355 | S353 | C368 | C321 |
| N473 | N467 | N486 | N472 | N471 | N486 | N439 |

| | OsDGAT1 (SEQ ID NO: 16) Rice | SbDGAT1b (SEQ ID NO: 18) Sorghum | TaDGAT1 (SEQ ID NO: 20) Wheat | ZmDGAT1-2 (SEQ ID NO: 22) Maize | EgDGAT1-1 (SEQ ID NO: 24) Palm |
|---|---|---|---|---|---|
| | S78 | E57 | L61 | G51 | G60 |
| | T215 | T192 | R187 | G170 | S197 |
| | A244 | A221 | A216 | A199 | P226 |
| | L250 | V227 | V222 | V205 | N232 |
| | D292 | D269 | E264 | E247 | H266 |
| | T298 | T275 | T270 | T253 | S272 |
| | K362 | K339 | K334 | K317 | K336 |
| | L398 | L375 | L370 | V353 | L372 |
| | E421 | E398 | E393 | E376 | E395 |
| | I474 | I451 | I446 | I429 | I448 |
| | R501 | N478 | K473 | K456 | K475 |
| | F513 | F490 | F485 | F468 | F487 |
| | A44 | G23 | K27 | G21 | P26 |
| | A54 | K33 | P37 | A31 | S36 |
| | G278 | S255 | S250 | S233 | S260 |
| | A389 | C366 | S361 | C344 | C363 |
| | N507 | N484 | N479 | N462 | N481 |

The substitutions may include one or more of the following with respect to the corresponding position in SEQ ID NO:2: S24A, S34A, S58N, P181A, A210V, T216V, L244A, D258E, S264T, K328N, C355S, L364V, D387E, I440M, R467Q, N473S, and I479S.

In some embodiments the polynucleotides disclosed herein may be isolated polynucleotides. An "isolated polynucleotide" generally refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A regulatory element generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

An enhancer element is any nucleic acid molecule that increases transcription of a nucleic acid molecule when functionally linked to a promoter regardless of its relative position. An enhancer may be an innate element of the promoter or a heterologous element inserted to enhance the level or tissue-specificity of a promoter.

A repressor (also sometimes called herein silencer) is defined as any nucleic acid molecule which inhibits the transcription when functionally linked to a promoter regardless of relative position.

Promotors which may be useful in the methods and compositions provided include those containing cis elements, promoters functional in a plant cell, tissue specific and tissue-preferred promotors, developmentally regulated promoters and constitutive promoters. "Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements. Endogenous promotors are those sequences that are operably connected to a polypeptide coding sequence in the native gene and which regulate transcription of the polypeptide coding sequence in the plant. An endogenous promotor of a modified polynucleotide is one which is operably connected to and regulates or controls transcription of the unmodified version of the polynucleotide in the native, unmodified or wild-type plant.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

"Promoter functional in a plant" is a promoter capable of initiating transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" generally refers to a promoter whose activity is determined by developmental events.

"Constitutive promoter" generally refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

Variant promotors can be used in the methods and compositions disclosed herein. A "variant promoter" as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Provided are sequences which are heterologous nucleotide sequences which can be used in the methods and compositions disclosed herein. A "heterologous nucleotide sequence" generally refers to a sequence that is not naturally occurring with the sequence of the disclosure. While this nucleotide sequence is heterologous to the sequence, it may be homologous, or native, or heterologous, or foreign, to the plant host. However, it is recognized that the instant sequences may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Provided are functional fragments of the sequences disclosed herein. A "functional fragment" refers to a portion or subsequence of the sequence described in the present disclosure in which the active properties of the full-length sequence is retained. Fragments can be obtained via methods such as site-directed mutagenesis and synthetic construction. For example, for promoter sequences described or used herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the sequences of the present disclosure is any nucleic acid fragment that is capable of being expressed in a similar manner to the Target sequences of the present disclosure.

In some aspects of the present disclosure, the fragments of polynucleotide sequences disclosed herein (such as SEQ ID NOS: 1, 3, 5, 7, 9, 11, 13, 15, 17, 19, 21, 23, 25, 26, 29 or 30) can comprise at least about 20, 30, 40, 50, 60, 70, 80, 90, 100, 125, 150, 175, 200, 225, 250, 275, 300, 350, 375, 400, 425, 450, 475, 500, 525, 550, 575, 600, 625, 650, 675, 700, 725, 750, 7775, 800, 825, 850, 875, 900, 925, 950, 1000, 1025, 1050, 1075, 1100, 1125, 1150, 1175, 1200, 1225, 1250, 1275, 1300, 1325, 1350, 1375, 1400, 1420, 1450, 1475 or 1500 contiguous nucleotides, or at least about 20, 30, 40, 50, 60, 70, 80, 90, 100, 125, 150, 175, 200, 225, 250, 275, 300, 350, 375, 400, 425, 450, 475, 500, 525, 550, 575, 600, 625, 650, 675, 700, 725, 750, 7775, 800, 825, 850, 875, 900, 925, 950, 1000, 1025, 1050, 1075, 1100, 1125, 1150, 1175, 1200, 1225, 1250, 1275, 1300, 1325, 1350, 1375, 1400, 1420, 1450, 1475 or 1500 contiguous nucleotides of nucleic acid sequences encoding polypeptides of SEQ ID NOS: 1, 3, 5, 7, 9, 11, 13, 15, 17, 19, 21 or 23. In another aspect of the present disclosure, the fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1110 contiguous nucleotides, or at least about 1150 contiguous nucleotides, or at least about 1200, or at least about 1250 contiguous nucleotides, or at least about 1300 contiguous nucleotides or at least about 1350 contiguous nucleotides and further may include a sequence encoding an amino acid modification corresponding to the substitutions described herein.

Provided are sequences that are a full complement or a full-length complement of those disclosed herein, such as the nucleotide coding sequences in Table 1 containing the modifications disclosed herein. The terms "full complement" and "full-length complement" are used interchangeably herein, and refer to a complement of a given nucleotide sequence, wherein the complement and the nucleotide sequence consist of the same number of nucleotides and are 100% complementary.

Provided are sequences that are "substantially similar" or "corresponding substantially" to those disclosed herein which can be used in the methods and compositions described herein. The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

Provided are compositions and methods that includes materials, steps, features, components, or elements that consist essentially of a particular component. The transitional phrase "consisting essentially of" generally refers to a composition, method that includes materials, steps, features, components, or elements, in addition to those literally disclosed, provided that these additional materials, steps, features, components, or elements do not materially affect the basic and novel characteristic(s) of the claimed subject matter, e.g., one or more of the claimed sequences.

Isolated promoter sequences can be comprised in the methods and compositions, such as a recombinant DNA construct, of the present disclosure and can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present disclosure can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended levels about $1/10,000$ transcripts to about $1/100,000$ transcripts to about $1/500,000$ transcripts. Conversely, a strong promoter drives expression of a coding sequence at high level, or at about $1/10$ transcripts to about $1/100$ transcripts to about $1/1,000$ transcripts. Similarly, a "moderate constitutive" promoter is somewhat weaker than a strong constitutive promoter like the maize ubiquitin promoter.

In addition to modulating gene expression, the expression modulating elements disclosed herein are also useful as probes or primers in nucleic acid hybridization experiments. The nucleic acid probes and primers hybridize under stringent conditions to a target DNA sequence. A "probe" is generally referred to an isolated/synthesized nucleic acid to which, is attached a conventional detectable label or reporter molecule, such as for example, a radioactive isotope, ligand, chemiluminescent agent, bioluminescent molecule, fluorescent label or dye, or enzyme. Such detectable labels may be covalently linked or otherwise physically associated with the probe. "Primers" generally referred to isolated/synthesized nucleic acids that hybridize to a complementary target DNA strand which is then extended along the target DNA strand by a polymerase, e.g., a DNA polymerase. Primer pairs often used for amplification of a target nucleic acid sequence, e.g., by the polymerase chain reaction (PCR) or other conventional nucleic-acid amplification methods. Primers are also used for a variety of sequencing reactions, sequence captures, and other sequence-based amplification methodologies. Primers are generally about 15, 20, 25 nucleotides or more, and probes can also be longer about 30, 40, 50 and up to a few hundred base pairs. Such probes and primers are used in hybridization reactions to target DNA or RNA sequences under high stringency hybridization conditions or under lower stringency conditions, depending on the need.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

In some embodiments, substantially similar nucleic acid sequences encompassed by this disclosure are those sequences that are at least about or about 80% identical to the nucleic acid fragments reported herein or which are at least about or about 80% identical to any portion of the nucleotide sequences reported herein. Nucleic acid fragments which are at least 90% or at least 95% identical to the nucleic acid sequences reported herein, or which are at least 90% or at least 95% identical to any portion of the nucleotide sequences reported herein are also provided. It is well understood by one skilled in the art that many levels of sequence identity are useful in identifying related polynucleotide sequences. Useful examples of percent identities are those listed above, or also preferred is any integer percentage from 70% to 100%, such as at least, at least about or about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%. In some embodiments, the sequences may have at least about or about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% percent identity to positions 247 to 1512 of SEQ ID NO: 1, or to a sequence encoding positions 108-504 of SEQ ID NO: 2, or corresponding thereto.

In one embodiment, the nucleotide sequences or isolated or modified sequences of the present disclosure comprise at least one modification disclosed herein and comprise a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOS: 1, 3, 5, 7, 9, 11, 13, 15, 17, 19, 21, 23, 25, 26, 29 or 30 or encode polypeptides having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of SEQ ID NOS: 2, 4, 6, 10, 12, 1,4 16, 18, 20, 22, 24, 27 or 28. It is known to one of skilled in the art that a 5' UTR region can be altered (deletion or substitutions of bases) or replaced by an alternative 5'UTR while maintaining promoter activity.

In one embodiment, the polypeptide sequences or isolated or modified sequences of the present disclosure comprise a polypeptide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of SEQ ID NOS: 2, 4, 6, 8 10, 12, 1,4 16, 18, 20, 22, 24, 27 or 28.

Provided are substantially similar sequences useful in compositions and methods provided herein. A "substantially similar sequence" generally refers to variants of the disclosed sequences such as those that result from site-directed mutagenesis, as well as synthetically derived sequences. A substantially similar promoter sequence of the present disclosure also generally refers to those fragments of a particular promoter nucleotide sequence disclosed herein that operate to promote the constitutive expression of an operably linked heterologous nucleic acid fragment. These promoter fragments comprise at least about 20 contiguous nucleotides, at least about 50 contiguous nucleotides, at least about 75 contiguous nucleotides, at least about 100 contiguous nucleotides of the particular promoter nucleotide sequence disclosed herein or a sequence that is at least 95 to about 99% identical to such contiguous sequences. The nucleotides of such fragments will usually include the TATA recognition sequence (or CAAT box or a CCAAT) of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. Variants of these promoter fragments, such as those resulting from site-directed mutagenesis, are encompassed by the compositions of the present disclosure.

Provided are sequences which contain one or more degenerate codons to those provided in the sequence listing. "Codon degeneracy" generally refers to divergence in the genetic code permitting variation of the nucleotide sequence without affecting the amino acid sequence of an encoded polypeptide. Accordingly, the instant disclosure relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect similar or identical sequences including, but not limited to, the MEGALIGN® program of the LASERGENE® bioinformatics computing suite (DNASTAR® Inc., Madison, WI). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v 6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid). A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN generally refers to a BLAST program that compares a nucleotide query sequence against a nucleotide sequence database.

The present disclosure provides genes, mutated genes, modified genes, chimeric genes and recombinant expression constructs. "Gene" includes a nucleic acid fragment that expresses a functional molecule such as, but not limited to, a specific protein, including regulatory sequences preceding (5' non-coding sequences) and following (3' non-coding sequences) the coding sequence. "Native gene" generally refers to a gene as found in nature with its own regulatory sequences.

A "mutated gene" or "modified gene" is a gene that has been altered through human intervention. Such a "mutated gene" or "modified gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated or modified plant is a plant comprising a mutated or modified gene.

"Chimeric gene" or "recombinant expression construct", which are used interchangeably, includes any gene that is not a native gene, comprising regulatory and coding sequences that are not found together in nature. Accordingly, a chimeric gene may comprise regulatory sequences and coding sequences that are derived from different sources.

A "mutated polynucleotide" or "modified polynucleotide" is a polynucleotide that has been altered through human intervention. Such a "mutated polynucleotide" or "modified polynucleotide" has a sequence that differs from the sequence of the corresponding non-mutated or modified polypeptide by at least one nucleotide addition, deletion, or substitution. In certain embodiments of the disclosure, the mutated polynucleotide comprises an alteration that results from a guide polynucleotide/Cas endonuclease system as disclosed herein. A mutated or modified plant is a plant comprising a mutated or modified polynucleotide.

"Coding sequence" generally refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" generally refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") generally refers to RNA that is without introns and that can be translated into protein by the cell. "cDNA" generally refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA generally refers to RNA transcript that includes mRNA and so can be translated into protein within a cell or in vitro. "Antisense RNA" generally refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" generally refers to antisense RNA, ribozyme RNA, or other RNA that may not be translated but yet has an effect on cellular processes.

The term "operably linked" or "functionally linked" generally refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, generally refers to the production of a functional end-product e.g., an mRNA or a protein (precursor or mature).

The term "expression cassette" as used herein, generally refers to a discrete nucleic acid fragment into which a nucleic acid sequence or fragment can be cloned or synthesized through molecular biology techniques.

Expression or overexpression of a gene involves transcription of the gene and translation of the mRNA into a precursor or mature protein. "Antisense inhibition" generally refers to the production of antisense RNA transcripts capable of suppressing the expression of the target protein. "Overexpression" generally refers to the production of a gene product in transgenic organisms that exceeds levels of production in normal or non-transformed organisms. "Co-suppression" generally refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

As stated herein, "suppression" includes a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" generally refers to an enzyme that is produced naturally in a non-transgenic or wild type cell. The terms "non-transgenic" and "wild type" are used interchangeably herein.

"Altering expression" or "modulating expression" generally refers to the production of gene product(s) in plants in amounts or proportions that differ significantly from the amount of the gene product(s) produced by the corresponding wild-type plants (i.e., expression is increased or decreased).

"Transformation" as used herein generally refers to both stable transformation and transient transformation.

"Stable transformation" generally refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" generally refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Genome" as it applies to plant cells encompasses not only chromosomal DNA found within the nucleus, but organelle DNA found within subcellular components (e.g., mitochondrial, plastid) of the cell.

"Genetic modification" generally refers to modification of any nucleic acid sequence or genetic element by insertion, deletion, or substitution of one or more nucleotides in an endogenous nucleotide sequence by genome editing or by insertion of a recombinant nucleic acid, e.g., as part of a vector or construct in any region of the plant genomic DNA by routine transformation techniques. Examples of modification of genetic components include, but are not limited to, polypeptide coding sequences, promoter regions, 5' untranslated leaders, introns, genes, 3' untranslated regions, and other regulatory sequences or sequences that affect transcription or translation of one or more nucleic acid sequences.

In an embodiment the seeds, such as soybean seeds, have an increased oil or fatty acid content as described herein, and optionally modified amounts of fatty acids, such as at least a 5%, 10%, 15%, 20%, 25%, 30%, 40%, or 50% increase in oleic acid content expressed by weight as a proportion of the total fatty acid content as described herein. The seeds, such a soybean seeds may have an increased protein content of at least 1%, 2%, 3%, 4%, 5%, 6%, 7%, 8%, 9%, 10%, 15%, 20% or 25% by weight.

In an embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

I. Gene Editing

In some embodiments, gene editing may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein the guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, Science 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein the guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein the guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein the guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, Agrobacterium transformation or topical applications. The guide polynucleotide can also be introduced indirectly into a cell by introducing a recombinant DNA molecule (via methods such as, but not limited to, particle bombardment or Agrobacterium transformation) comprising a heterologous nucleic acid fragment encoding a guide polynucleotide, operably linked to a specific promoter that is capable of transcribing the guide RNA in the cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

Provided are plants and seeds which contain an altered or modified target site or sequence. An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

Methods to modify or alter endogenous genomic DNA are known in the art. In some aspects, methods and compositions are provided for modifying naturally-occurring polynucleotides or integrated transgenic sequences, including regulatory elements, coding sequences, and non-coding sequences. These methods and compositions are also useful in targeting nucleic acids to pre-engineered target recognition sequences in the genome. Modification of polynucleotides may be accomplished, for example, by introducing single- or double-strand breaks into the DNA molecule.

Double-strand breaks induced by double-strand-break-inducing agents, such as endonucleases that cleave the phosphodiester bond within a polynucleotide chain, can result in the induction of DNA repair mechanisms, including the non-homologous end-joining pathway, and homologous recombination. Endonucleases include a range of different enzymes, including restriction endonucleases (see e.g. Roberts et al., (2003) Nucleic Acids Res 1:418-20), Roberts et al., (2003) Nucleic Acids Res 31:1805-12, and Belfort et al., (2002) in Mobile DNA II, pp. 761-783, Eds. Craigie et al., (ASM Press, Washington, DC)), meganucleases (see e.g., WO 2009/114321; Gao et al. (2010) Plant Journal 1:176-187), TAL effector nucleases or TALENs (see e.g., US20110145940, Christian, M., T. Cermak, et al. 2010. Targeting DNA double-strand breaks with TAL effector nucleases. Genetics 186(2): 757-61 and Boch et al., (2009), Science 326(5959): 1509-12), zinc finger nucleases (see e.g. Kim, Y. G., J. Cha, et al. (1996). "Hybrid restriction enzymes: zinc finger fusions to Fokl cleavage"), and CRISPR-Cas endonucleases (see e.g. WO2007/025097 application published Mar. 1, 2007).

Once a double-strand break is induced in the genome, cellular DNA repair mechanisms are activated to repair the break. There are two DNA repair pathways. One is termed nonhomologous end-joining (NHEJ) pathway (Bleuyard et al., (2006) DNA Repair 5:1-12) and the other is homology-directed repair (HDR). The structural integrity of chromosomes is typically preserved by NHEJ, but deletions, insertions, or other rearrangements (such as chromosomal translocations) are possible (Siebert and Puchta, 2002, Plant Cell 14:1121-31; Pacher et al., 2007, Genetics 175:21-9. The HDR pathway is another cellular mechanism to repair double-stranded DNA breaks, and includes homologous recombination (HR) and single-strand annealing (SSA) (Lieber. 2010 Annu. Rev. Biochem. 79:181-211).

In addition to the double-strand break inducing agents, site-specific base conversions can also be achieved to engineer one or more nucleotide changes to create one or more EMEs described herein into the genome. These include for example, a site-specific base edit mediated by an C•G to T•A or an A•T to G•C base editing deaminase enzymes (Gaudelli et al., Programmable base editing of A•T to G•C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide a guide polynucleotide/Cas endonuclease complex to a unique DNA target site.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

Provided are plants which are dicots. The terms "dicot" and "dicotyledonous plant" are used interchangeably herein. A dicot of the current disclosure includes the following families: Brassicaceae, Leguminosae, and Solanaceae.

Progeny plants are provided. "Progeny" comprises any subsequent generation of a plant, and can include F1 progeny, F2 progeny F3 progeny and so on.

The heterologous polynucleotide can be stably integrated within the genome such that the polynucleotide is passed on to successive generations. The heterologous polynucleotide may be integrated into the genome alone or as part of a recombinant DNA construct. The alterations of the genome (chromosomal or extra-chromosomal) by conventional plant breeding methods, by genome editing procedures that do not result in an insertion of a foreign polynucleotide, or by naturally occurring events such as random cross-fertilization, non-recombinant viral infection, non-recombinant bacterial transformation, non-recombinant transposition, or spontaneous mutation are also methods of modifying a host genome.

"Transient expression" generally refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; 2nd ed.; Cold Spring Harbor Laboratory Press: Cold Spring Harbor, New York, 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, CT). Typically, the double stranded DNA is heat denatured, the two primers complementary to the 3' boundaries of the target segment are annealed at low temperature and then extended at an intermediate temperature. One set of these three consecutive steps comprises a cycle.

Provided are plasmids, vectors and cassettes which contain one or more of the sequences provided, including any combination of sequence components disclosed in the Examples. The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Provided are recombinant DNA constructs or recombinant expression constructs which contain the sequences disclosed herein, including any combination of sequence components disclosed in the Examples. The term "recombinant DNA construct" or "recombinant expression construct" is used interchangeably and generally refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, US application publication 2017-0306349, filed on Jul. 7, 2014, and US application publication 2017-0226533, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Methods for transforming dicots, primarily by use of Agrobacterium tumefaciens, and obtaining transgenic plants have been published, among others, for cotton (U.S. Pat. Nos. 5,004,863, 5,159,135); soybean (U.S. Pat. Nos. 5,569,834, 5,416,011); Brassica (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses Agrobacterium rhizogenes (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, CA, 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

This disclosure also concerns a method of decreasing the expression of at least one nucleic acid such as a heterologous nucleic acid fragment in a plant cell which comprises:
(a) transforming a plant cell with the recombinant expression construct described herein;
(b) growing fertile mature plants from the transformed plant cell of step (a);
(c) selecting plants containing a transformed plant cell wherein the expression of the nucleic acid such as a heterologous nucleic acid fragment is increased or decreased.
Transformation and selection can be accomplished using methods well-known to those skilled in the art including, but not limited to, the methods described herein.

The soybean seeds can be processed to produce oil and protein. Methods of processing the soybean seeds to produce oil and protein are provided which include one or more steps of dehulling the seeds, crushing the seeds, heating the seeds, such as with steam, extracting the oil, roasting, and extrusion. Processing and oil extraction can be done using solvents or mechanical extraction.

Products formed following processing include, without limitation, soy nuts, soy milk, tofu, texturized soy protein, soybean oil, soy protein flakes, isolated soy protein. Crude or partially degummed oil can be further processed by one or more of degumming, alkali treatment, silica absorption, vacuum bleaching, hydrogenation, interesterification, filtration, deodorization, physical refining, refractionation, and optional blending to produce refined bleached deodorized (RBD) oil.

The oil and protein can be used in animal feed and in food products for human consumption. Provided are food products and animal feed comprising oils, protein and compositions and described herein which contain or are derived from the modified polynucleotides and modified polypeptides. The food products and animal feed may comprise nucleotides comprising one or more of the modified alleles disclosed herein and the modified polynucleotides, polypeptides and plant cell disclosed herein.

Methods of detecting the modified polynucleotides are provided. Methods of extracting modified DNA from a sample or detecting the presence of DNA corresponding to the modified genomic sequences comprising deletions or substitutions disclosed herein in DGAT1 sequences are provided. Such methods comprise contacting a sample comprising soybean genomic DNA with a DNA primer set, that when used in a nucleic acid amplification reaction, such as the polymerase chain reaction (PCR), with genomic DNA extracted from soybeans produces an amplicon that is diagnostic for either the presence or absence of the modified polynucleotide or modified DGAT1 alleles. The methods include the steps of performing a nucleic acid amplification reaction, thereby producing the amplicon and detecting the amplicon. In some embodiments one of the pair of DNA molecules comprises the wild type sequence where the modification such as a deletion occurs with the second of the pair being upstream or downstream as appropriate and suitably in proximity to the wild type sequence where the modification such as deletion occurs, such that an amplicon is produced when the wild type allele is present, but no amplicon is produced when the modified allele is present.

Probes and primers are provided which are of sufficient nucleotide length to bind specifically to the target DNA sequence under the reaction or hybridization conditions. Suitable probes and primers are at least 10, 11, 12, 13, 14, 15, 16, 17, 18, 19, 20, 21, 22, 23, 24, 25, 26, 27, 28, 29 or 30 nucleotides in length, and less than 35, 34, 33, 32, 31, 30, 29, 28, 27, 26, 2,5 2,4 23, 22, 21, 20, 19, 18, 17, 16, 15, 14, 13, or 12 nucleotides in length. Such probes and primers can hybridize specifically to a target sequence under high stringency hybridization conditions. Preferably, probes and primers have complete or 100% DNA sequence similarity of contiguous nucleotides with the target sequence, although probes which differ from the target DNA sequence but retain the ability to hybridize to target DNA sequence may be also be used. Reverse complements of the primers and probes disclosed herein are also provided and can be used in the methods and compositions described herein.

In some embodiments, one of the pair of DNA molecules comprises the modification or traverses the modification junction, such as, for example, the deletion junctions occurring at position 77 to 78 of SEQ ID NO: 25, or the deletion junctions occurring at position 73 to 74 of SEQ ID NO: 26 with the second DNA molecule of the pair being upstream or downstream of the genomic sequence as appropriate, such that an amplicon is produced when the modified allele is present, but no amplicon is produced when the wild type allele is present. Suitable primers for use in reactions to detect the presence of the modified alleles can be designed based on the junction sequences depicted in FIGS. 1-3 for the modified alleles. The deletion junction sequence can include at least 1, 2, 3, 4, 5, 6, 7, 8, 9, 10, 11, 12, 13, 14, 15, 20, 25 or 30 nucleotides upstream and downstream of the junction, such as provided in SEQ ID NOs: 25 and 26. The modified polynucleotides disclosed herein can include the deletion junction and deletion junction sequences described herein.

Various changes in phenotype are of interest including, but not limited to, one or more of increased stability of the DGAT polypeptide or protein or RNA in the cell, increased expression levels of the DGAT protein or RNA in the cell, increased activity, such as specific activity of the DGAT protein in the cell, increased oil or fatty acid production or oil of fatty acid content of the cell or increased protein content or protein production in the cell.

Methods for extracting and detecting triacylglycerol (TAG), fats or oils from tissues such as leaves, roots and seeds are provided herein. The methods can be used to extract TAG and quantify, measure or detect TAG from the modified leaves or seeds described herein. In some embodiments, the methods include the steps of conducting Solid Phase Extraction (SPE) followed by quantitative gas chromatography. In some embodiments, the methods include the steps of conducting high performance liquid chromatography such as equipped with an evaporative light scattering detector (HPLC-ELSD). TAG is extracted from the tissue, such as leaf or seed tissue, for example using a solvent such as hexane. The methods facilitate an improvement in accuracy of measuring TAG in tissues of at least 1%, 2%, 3%, 4%, 5%, 6%, 7% 8%, 9% or 10% and less than 25%, 20%, 15% or 10%.

For the SPE method, a plate containing a plurality of wells can be used, such as at least 12, 24, 36, 48, 60, 72, 84, or 96 and less than 1026, 512, 256, 128, or 100 wells. Hexane or other solvent can be used to precondition the columns and to load the fractions. Columns can be washed with hexane: dichloromethane:chloroform, such as at an 88:10:4 v/v ratio. Elution of TAG from the columns can be done using a hexane:ethyl acetate blend, at a ratio of at least 95:5, 96:4, and 97:3 hexane:ethyl acetate (v/v) and less than 98:2 and 97:3 hexane:ethyl acetate (v/v). For example, a ratio of 96:4 hexane:ethyl acetate (v/v) can be used. The TAG fraction can be concentrated and resuspended in a solvent such as heptane, derivatization of fatty acids may be carried out for example using trimethylsulfonium hydroxide in methanol, followed by Gas Chromatography—Flame Ionization Detector (GC-FID) for quantification.

For the HPLC-ELSD procedure, the hexane-extracted lipids can be filtered such as through a PTFE filter plate, dried down and resuspended in a solvent such as heptane. A column such as a cyanopropyl column can used to separate lipid species on an HPLC-ELSD. A first phase may include up to 100% hexane (mobile phase A) and a second phase (mobile phase B) may include up to 100% methyl tertiary-butyl ether or a methyl tertiary-butyl ether: isopropanol blend with at least 0%, 0.01%, 0.1%, 0.5%, 1%, 1.5% or 2% and less than 10%, 9%, 8%, 7%, 6%, 5%, 4%, 3%, 2%, 1% or 0.5% isopropanol (v/v) and at least 0%, 0.01%, 0.1%, 0.2%, 0.3%, 0.4% or 0.5% and less than 0.6%, 0.5%, 0.4%, 0.3%, 0.2% or 0.1% (v/v) acetic acid. The gradient can be run for example at 0% to 100% of mobile phase B, with re-equilibration of the column to 0% mobile phase B.

The foregoing invention has been described in detail by way of illustration and example for purposes of clarity and understanding. As is readily apparent to one skilled in the art, the foregoing disclosures are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

All publications, patents, and patent applications mentioned in the specification are incorporated by reference herein for the purpose cited to the same extent as if each was specifically and individually indicated to be incorporated by reference herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present).

Example 1

Evaluation of DGAT Variants in Yeast by Measuring Oil Accumulation

Yeast (*Saccharomyces cerevisiae*) double mutant (dga1/lro1) was generated for evaluating soybean DGAT variants. The yeast mutant is DGAT/PDAT double null which accumulates a trace amount of oil and can be complemented by soybean DGAT variants. DGAT variants were cloned into a yeast expression vector between PGK1 promoter and PGK1 terminator. The vector was transformed into yeast using a modified version of Clontech Yeastmaker Yeast Transformation Kit. Total 18 independent colonies were picked for each DGAT variant to start liquid culture. Oil content in yeast was determined by staining yeast cell with a fluorescence lipolytic dye, Nile Red. Nile Red staining was performed in 96-well microtiter plates by adding 5 µL of a 0.02 mg per mL stock of Nile Red dissolved in 95% ethanol to 200 mL of a 1:10 dilution of the yeast culture in phosphate-buffered saline (137 mM NaCl, 2.7 mM KCl, 10 mM Na2HPO4, and 1.8 mM KH2PO4, pH 7.4). Staining was done for 5 min, followed by the determination of fluorescence intensity using an excitation wavelength of 489 nm and an emission wavelength of 581 nm. Fluorescence intensity was divided by A600 to correct for differences in cell density, and buffer blanks with no yeast were used to correct for background (Roesler et al 2016 Plant Physiol. 171:878).

Oil content (total fatty acid methyl esters as a percentage of dry weight) and fatty acid composition were determined by quantitative gas chromatography for yeast strains with high Nile Red staining.

Example 2

Evaluation of DGAT Variants in Tobacco Leaf Transient Expression by Measuring Oil Accumulation DGAT variants were evaluated in planta by *Agrobacterium* mediated transient expression in tobacco (*N. benthamiana*) leaves. Gene variants were first cloned into a binary vector between the GM-UBQ promoter and UBQ14 terminator. The constructs also contained DsRed under control of the SCP1 promoter as marker gene. Vectors were transformed into *Agrobacterium* strain AGL1 by electroporation. Liquid cultures were grown at 28 C overnight in a shaking incubator at 250 rpm. Cells were then pelleted and resuspended in infiltration buffer (5 mM MgSO4, 5 mM MES (pH 5.6), and 150 µM acetosyringone). Cultures were then incubated at room temperature for 2-4 hours and diluted to a final OD 600 of 0.2 prior to infiltration. Tobacco plants were grown for approximately 5 weeks before infiltration in a growth chamber under a 16-hour photoperiod, light intensity of 180 µmol·m-2·s-1, 24 C/20 C light/dark temperature, and 65% relative humidity. The youngest fully expanded leaf was chosen for infiltration (one leaf per plant). *Agrobacterium* suspensions were injected into the underside of leaves using a syringe without a needle while applying counter pressure. The Agrobacterium suspension can be seen filling airspaces inside the leaf, which is a visible wetting of the area. Infiltrated leaves were harvested 3 days post-infiltration, frozen on dry ice, and lyophilized. Lipids were extracted from 20 mg dry weight in 2:1 chloroform:methanol after the addition of 0.05 mg tri-C17 TAG as an internal standard. Extracts were loaded on a silica TLC plate and resolved with 70:30:1 hexane:diethylether:acetic acid. The plate was stained with primuline and visualized under UV light. TAG spots were scraped from the plate and derivatized with 5% sulfuric acid in methanol followed by GC-FID. Protein was extracted and analyzed by the Protein Mass Spectrometry.

Example 3

Deletion of amino Acids in N-Terminal of DGAT Improves DGAT Protein Stability and Produces More Oil in Tobacco Leaf Oil was measured in a tobacco leaf assay according to Example 2. Different DGAT variants were expressed transiently in tobacco leaf under the same soybean UBQ promoter. DGAT protein level was determined by mass spectrometry. The results are presented in FIG. 1. Deletion of AA25-44 at the N-terminus of the DGAT1b WT protein resulted in a 66 percent increase in DGAT protein level, indicating increased DGAT1b stability. The AA25-44 deletion resulted in a similar increase in protein in the GmDGAT1b mod backbone with 14 amino acid substitutions, where a 61 percent increase in protein was observed. The unmodified DGAT1a protein is more stable and expressed at a higher level in tobacco leaf compared to DGAT1b.

Oil content in tobacco leaf expressing different DGAT variants was determined by GC-FID. The results are presented in FIG. 2. Expression of DGAT1b WT increases oil slightly in tobacco leaf. Deletion of AA25-44 in N-terminal of DGAT1b increases oil content in tobacco leaf by 100%. Similarly, Substitution of 14 AA in DGAT1b mod increases oil content by 149%. The stack of AA25-44 deletion with 14 AA substitution provided an increase in oil more than either the AA25-44 deletion or 14 AA substitution. DGAT1b mod and stack of AA25-44 deletion with 14 AA substitution showed a much higher oil content than wild type DGAT1a in tobacco leaves.

Example 4

Substitution of a Single Amino Acid in DGAT Increases Oil Accumulation in Yeast DGAT variants with a single amino acid substitution at various position was expressed under PGK1 promoter in a yeast double mutant as described in Example 1. Oil content in yeast cells were determined by Nile Red staining. Out of 33 variants in DGAT1b backbone tested, 7 DGAT variants show a significant increase in oil content compared to wild type DGAT1b. Similarly, out of 29 variants in DGAT1a backbone tested, 12 DGAT variants showed a significant increase in oil content compared to wild type DGAT1a in yeast (Table 4). The 15 amino acid substitutions showing positive effect on oil accumulation in either DGAT1a or DGAT1b are listed in Table 3.

TABLE 3

List of positive single amino acid substitutions in soybean DGAT1a or DGAT1b

| GmDGAT1B (SEQ ID NO: 2) | GmDGAT1a (SEQ ID NO: 4) |
|---|---|
| BAE93461.1 | AAS78662.1 |
| S58N * | S55N |
| P181A | P175A * |
| A210V * | A204V |
| T216V * | T210V * |
| D258E * | D252E * |
| S264T * | S258T * |
| K328N | K322N * |
| L364V | L358V * |
| D387E | D381E * |
| I440M * | I434M |
| R467Q | R461Q * |
| I479S * | I473S * |
|  | T24A * |
|  | S31A * |
|  | S238A * |

* indicates DGAT with a single amino acid substitution shows a significant increase in oil content compared to wild type DGAT at P < 0.05

TABLE 4

Soybean DGAT with a single amino acid substitution increases oil accumulation in yeast

| DGAT Allele | AA Change | % of WT oil content | Significance |
|---|---|---|---|
| DGAT1b | S58N | 123.68 | * |
| DGAT1b | A210V | 119.52 | * |
| DGAT1b | T216V | 136.83 | * |
| DGAT1b | D258E | 134.39 | * |
| DGAT1b | S264T | 121.01 | * |
| DGAT1b | I440M | 114.97 | * |
| DGAT1b | I479S | 146.61 | * |
| DGAT1a | T24A | 107.63 | * |
| DGAT1a | S31A | 114.75 | * |
| DGAT1a | P175A | 107.21 | * |
| DGAT1a | T210V | 107.85 | * |
| DGAT1a | S238A | 105.45 | * |
| DGAT1a | D252E | 115.97 | * |
| DGAT1a | S258T | 112.78 | * |
| DGAT1a | K322N | 113.19 | * |
| DGAT1a | L360V | 106.90 | * |
| DGAT1a | D381E | 105.06 | * |
| DGAT1a | R461Q | 109.47 | * |
| DGAT1a | I473S | 111.07 | * |

* indicates DGAT with a single amino acid substitution shows a significant increase in oil content compared to wild type DGAT at P < 0.05

Example 5

Substitution of a Single Amino Acid in DGAT Increases Oil Accumulation in Tobacco Leaf Four positive amino acid substitutions in DGAT1a and 6 positive amino acid substitutions in DGAT1b backbones were further tested in tobacco leaf transient expression as described in Example 2. The results are presented in FIG. 3. Amino acid changes from Threonine to valine at position 210, aspartate to glutamate at position 252, serine to valine at position 258, and isoleucine to serine in DGAT1a protein increases oil accumulation in tobacco leaves compared to DGAT1a wild type (FIG. 3). The corresponding amino acid substitutions in DGAT1b backbone show a similar oil increase compared against wild type DGAT1b in tobacco leaves.

Example 6

Identification of Positive Amino Acid Substitution in Plant DGAT

Plant DGAT amino acid sequences can be identified from public databases, for example using BLAST® (Basic Local Alignment Search Tool) using the soybean DGAT1a and DGTA1b sequences. The DGAT amino acid sequences can be pairwise aligned using alignment software. Corresponding amino acids which can be changed to increase DGAT activity in other plant DGAT proteins are marked with an asterisk in FIG. 4. The modified nucleotides encoding these polypeptides can be expressed in plant cells to produce cells containing modified DGAT polypeptides which show one or more of increased stability, increased specific activity and increased fatty acid content of the cell.

Example 7

Combination of 2-4 Amino Acid Changes in DGAT in Yeast

DGAT variants with 2-4 amino acid changes were expressed in yeast as described in Example 1. The different combinations tested and the results are presented in Table 5. Compared to WT DGAT, 8 out of 19 stack variants show an increase in oil accumulation. The stack variants contain at least one amino acid changes from the list in Table 3 of Example 4.

TABLE 5

DGAT variants with 2-4 amino acid changes increase oil content in yeast

| Soybean DGAT Allele | Amino Acid Changes | | | | % of WT oil content | Significance |
|---|---|---|---|---|---|---|
| GmDGAT1b | T216V | I479S | | | 98.75 | |
| GmDGAT1b | C355S | I479S | | | 93.14 | |
| GmDGAT1b | T216V | D258E | | | 98.72 | |
| GmDGAT1b | T216V | S264T | | | 91.90 | |
| GmDGAT1b | D258E | S264T | | | 89.61 | |
| GmDGAT1b | D258E | I479S | | | 128.06 | * |
| GmDGAT1b | K328N | C355S | I479S | | 127.54 | * |
| GmDGAT1b | C355S | N473S | I479S | | 84.80 | |
| GmDGAT1b | T216V | D258E | I479S | | 125.85 | * |
| GmDGAT1b | S58N | I170M | S264T | | 101.39 | |
| GmDGAT1b | R206K | Y231F | S264T | I440M | 70.12 | |
| GmDGAT1b | T216V | K328N | C355S | I479S | 99.37 | |
| GmDGAT1b | V273L | I303V | L364V | R467K | 111.96 | * |
| GmDGAT1b | T216V | D258E | S264T | I479S | 90.85 | |
| GmDGAT1a | T210V | I473S | | | 119.31 | * |
| GmDGAT1a | C349S | I473S | | | 104.03 | * |
| GmDGAT1a | T210V | D252E | | | 107.33 | * |
| GmDGAT1a | V267L | I297V | L358V | R461K | 100.41 | |
| GmDGAT1a | T210V | D252E | S258T | I473S | 125.59 | * |

* indicates DGAT with 2-4 amino acid substitutions show a significant increase in oil content compared to wild type DGAT at P < 0.05

Example 8

Combination of 2-4 Amino Acid Changes in DGAT in Tobacco Leaf Assay

The DGAT1b variants with 2-4 amino acid changes used in Example 7 were also tested in tobacco leaf transient expression. The results are presented in FIG. 5. Seven out of eleven DGAT1b variants with 2-4 amino acid substitutions show more oil accumulation than wild type DGAT1b. One DGAT1b variant with 3 amino acid substitutions, C355S, N473S, and I479S-increased oil more than the GmDGAT1b mod with 14 amino acid changes.

Example 9

Combination of N-Terminal Deletion with Amino Acid Substitution

The DGAT variant with N-terminal deletion at AA25-44 improves DGAT stability and increase oil accumulation in tobacco transient expression. DGAT variants which combined an N-terminal deletion with amino acid substitutions were tested to determine whether further increases DGAT activity and oil accumulation would occur. As shown in FIG. 6, GmDGAT1b mod with AA25-44 deletion accumulates more oil than either GmDGAT1b mod or GMDGAT1b with AA25-44 deletion. Similarly, GmDGAT1b with stack of C355S, N473S and I479S substitutions and the AA25-44 deletion increases oil more than either GmDGAT1b with AA25-44 deletion or GmDGAT1b with C355S, N473S and I479S substitutions. The combination of N-terminal deletion with C-terminal amino acid substitutions can further improve DGAT for higher oil accumulation.

Example 10

Soybean Optimized Expression Cassettes for Guide RNA/Cas Endonuclease based Genome Modification in Soybean Plants For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) Proc. Natl. Acad. Sci. USA 109: E2579-86, Jinek et al. (2012) Science 337:816-21, Mali et al. (2013) Science 339:823-26, and Cong et al. (2013) Science 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into the target site.

To use the guide RNA/Cas endonuclease system in soybean, the Cas9 gene from *Streptococcus pyogenes* M1 GAS (SF370) was soybean codon optimized per standard techniques known in the art. To facilitate nuclear localization of the Cas9 protein in soybean cells, a simian virus 40 (SV40) large T-antigen nuclear localization signal, representing the amino acid molecules of PKKKRKV (with a linker SRAD (SRADPKKKRKV), was added to the carboxyl terminus of the codon optimized Cas9 to facilitate transporting the codon optimized Cas9 protein to the nucleus. The soybean optimized Cas9 gene was operably linked to a soybean constitutive promoter such as the strong soybean constitutive promoter GM-EF1A2 (US patent application 20090133159). or regulated promoter by standard molecular biological techniques.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in soybean, the soybean U6 polymerase III promoter and U6 polymerase III terminator were used.

Plant U6 RNA polymerase III promoters have been cloned and characterized from such as Arabidopsis and Medicago truncatula (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using Arabidopsis U6 gene coding sequence. Approximately 0.5 kb genomic DNA sequence upstream of the first G nucleotide of a U6 gene was selected to be used as a RNA polymerase III promoter for example, GM-U6-13.1 promoter, to express guide RNA to direct Cas9 nuclease to designated genomic site. The guide RNA coding sequence was 76 bp long and comprised a 20 bp variable targeting domain from a chosen soybean genomic target site on the 5' end and a tract of 4 or more T residues as a transcription terminator on the 3' end. The first nucleotide of the 20 bp variable targeting domain was a G residue to be used by RNA polymerase III for transcription. Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct.

Example 11

Selection of Soybean DGAT1a and DGAT1b Target Sites to be Cleaved by the Guide RNA/Cas Endonuclease System Specific gRNAs are designed to target the two soybean DGAT genes (Glyma.13g106100 for DGAT1a and Glyma.17g053300 for DGAT1b). The GM-DGAT-CR1 is targeting the N-terminal region of DGAT1a gene. The GM-DGAT-CR3 is targeting the N-terminal region of the DGAT1b gene. The GM-DGAT-CR4 is targeting downstream of the N-terminal region of both DGAT1a and DGAT1b gene (Table 6).

TABLE 6

Guide RNA/Cas9 endonuclease target sites on soybean DGAT1a and DGAT1b genes a

| Name of gRNA-Cas9 endonuclease target site | Sequences (without PAM) |
|---|---|
| GM-DGAT-CR1 | GGAATTGAAGAGGCCAGCGG (SEQ ID NO: 31) |
| GM-DGAT-CR3 | GCGGCGGTGGAGGTGGCGGA (SEQ ID NO: 32) |
| GM-DGAT-CR4 | GGACAGTTCCGGTGATGACT (SEQ ID NO: 33) |

The soybean U6 small nuclear RNA promoter, GM-U6-13.1, was used to express the guide RNAs to direct Cas9 nuclease to designated genomic target sites. A soybean codon optimized Cas9 endonuclease expression cassette and a guide RNA expression cassette were linked in the plasmid (RTW1630, RTW1632 or RTW1633).

Example 12

Delivery of the Guide RNA/Cas9 Endonuclease System DNA to Soybean by Stable Transformation Soybean somatic embryogenic suspension cultures were induced from a DuPont Pioneer proprietary elite cultivar 93Y21 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8-hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 µl of a 60 mg/ml 1.0 mm gold particle suspension were added in order: 30 µl of equal amount (30 ng/µl) plasmid DNA, 20 µl of 0.1 M spermidine, and 25 µl of 5 M CaCl2. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or T0 leaf stage for molecular analysis.

Example 13

Detection of Site-Specific Dropout Mutations Mediated by the Guide RNA/Cas9 System in Stably Transformed Soybean Genomic DNA was extracted from somatic embryo samples and leaf samples and analyzed by PCR analyses using primers specific respectively to DGAT1a and DGAT1b genes (Tables 7 and 8).

TABLE 7

PCR primers for the deletion in the N-terminal region of the DGAT1a and DGAT1b genes

| Target Gene | Primer1 | SEQ ID NO: | Primer2 | SEQ ID NO: |
|---|---|---|---|---|
| DGAT1a | WOL1469 | 34 | WOL1470 | 35 |
| DGAT1b | WOL1471 | 36 | WOL1009 | 37 |

TABLE 8

Detection of the deletion in the N-terminal region of the DGAT1a and DGAT1b genes

| Target Site | Primer set | PCR band size of WT | PCR band size of band containing N-terminal deletion |
|---|---|---|---|
| DGAT1a | WOL1469/ WOL1470 | 485 bp (position 34-518 of SEQ ID NO: 30) | 437 bp (position 34-518 SEQ ID NO: 30) |
| DGAT1b | WOL1471/ WOL1472 | 557 bp (position 11-567 SEQ ID: 29) | 497 bp (position 11-567 SEQ ID: 29) |

The PCR bands were cloned into pCR2.1 vector using a TOPO-TA cloning kit (Invitrogen) and multiple clones were sequenced to check for target site sequence changes. The 48 bp dropout of the DGAT1a N-terminal region (corresponding to positions 77 to 124 of SEQ ID NO: 3) and 60 bp deletion of the DGAT1b (corresponding to positions 74 to 133 of SEQ ID NO: 1) N-terminal region were detected in the 2.1 variant, in which the DGAT1b N-terminal region deletion were presented as bi-allelic and the DGAT1a N-terminal region deletion was shown as mono-allelic, with the second DGAT1a allelic as a 1 bp deletion knockout (Table 9). For the 2.2 variant, mono-allelic dropout of the DGAT1a gene was detected, with the second DGAT1a allele as a WT. All other variants were detected either as frameshift knockouts or as WT alleles.

TABLE 9

N-terminal deletion or knockout variants of the DGAT1a and DGAT1b genes

| Variant | DGAT1a | DGAT1b |
|---|---|---|
| 2.1 | 48 bp dropout/1 bp del | 60 bp dropout/ 60 bp dropout |
| 2.2 | 48 bp dropout/WT | 2 bp del |
| 4.2 | WT | 1 bp del |
| 4.3 | WT | WT |

Example 14

Expression of Novel DGAT Genes in Soybean Seed

The expression of DGAT variants in soybean was described in detail previously (Roesler et al Plant Physiol. 2016 878-893). Briefly, DGAT variants were cloned into an expression vector flanked by seed specific soybean Ole 2b promoter and soybean MYB2 terminator. The expression vectors containing constructs as listed in Table 10 were introduced into soybean by Ochrobacteria transformation. Transgenic T1 seed oil content was determined by SS-NIR as described previously (Roesler et al Plant Physiol. 2016 878-893). While 75% of T1 seeds are transgenic, 25% of T1 seeds are wild type segregates. The average of all T1 seeds oil content is thus an underestimate of DGAT efficacy. Compared to untransformed 93Y21 wild type, overexpression of Gm-DGAT1b WT under the oleosin promoter does not increase seed oil content significantly. Gm-DGAT1b Mod with 14 amino acid substitutions shows a significant improvement in increasing oil compared to wild type DGAT1b (Table 10). To reduce number of amino acid substitutions to facilitate efficient gene editing, a few DGAT variants with 1-4 amino acid substitutions were tested in transgenic plants for increasing seed oil content. Gm-DGAT1b-I479S, Gm-DGAT1b-C355S-I479S, Gm-DGAT1b-C355S-N473S-I479S, and Gm-DGAT1b-T216V-D258E-S264T-I479S show a significant increase in seed oil content compared to wild type DGAT1b. Overexpression of Gm-DGAT1b-S264T and Gm-DGAT1b-D258E-I479S, however, does not increase seed oil content. In addition, substitution of 14 amino acids or a single amino acid substitution I473S in DGAT1a backbone increases seed oil content significantly compared to wild type DGAT1b and untransformed 93Y21 (Table 10)

TABLE 10

DGAT variants increases seed oil content in stable transgenic events

| Constructs | | | Average T1 seed oil % | Significance |
|---|---|---|---|---|
| Wild type 93Y21 | | | 19.75 ± 1.03 | |
| Gm-Ole2b promoter | Gm-DGAT1b-WT | Gm-MYB2 Term | 19.72 ± 0.97 | |
| Gm-Ole2b promoter | Gm-DGAT1b Mod | Gm-MYB2 Term | 21.52 ± 0.96 | ** |
| Gm-Ole2b promoter | Gm-DGAT1b-S264T | Gm-MYB2 Term | 19.88 ± 1.05 | |
| Gm-Ole2b promoter | Gm-DGAT1b-I479S | Gm-MYB2 Term | 21.01 ± 1.61 | ** |
| Gm-Ole2b promoter | Gm-DGAT1b-D258E-I479S | Gm-MYB2 Term | 20.06 ± 0.88 | |
| Gm-Ole2b promoter | Gm-DGAT1b-C355S-I479S | Gm-MYB2 Term | 20.86 ± 1.27 | ** |
| Gm-Ole2b promoter | Gm-DGAT1b-C355S-N473S-I479S | Gm-MYB2 Term | 21.02 ± 0.97 | ** |
| Gm-Ole2b promoter | Gm-DGAT1b-T216V-D258E-S264T-I479S | Gm-MYB2 Term | 21.20 ± 1.24 | ** |
| Gm-Ole2b promoter | Gm-DGAT1a Mod | Gm-MYB2 Term | 20.92 ± 1.37 | ** |
| Gm-Ole2b promoter | Gm-DGAT1a-I473S | Gm-MYB2 Term | 20.48 ± 1.13 | ** |

Example 15

Deletion Studies of N-Terminal Region of DGAT for Increasing DGAT Protein Stability The N-terminal region of DGAT before the first conserved membrane domain (e.g. from positions 1-108 of SEQ ID NO: 2) is variable and impacts DGAT protein stability. Different size deletions from one amino acid to 107 amino acids are made in this region. The efficacy of DGAT deletion variants are tested in tobacco leaf transient expression or in stable transgenic expression as described in Example 2 or in Roesler et al Plant Physiol. 2016 878-893. The deletion variants with improved stability are identified based on oil accumulation in tobacco leaf assay or transgenic plants. DGAT polypeptides with deletions ranging from 1 amino acid to 107 amino acids will show improved stability evidenced by increased protein levels or oil content in transformed cells compared with a comparable DGAT not comprising an N-terminal deletion. When expressed in a seed, DGAT polypeptides with deletions ranging from 1 amino acid to 107 amino acids will result in increased oil content in the seed compared with a comparable seed expressing the wild-type or native DGAT sequences.

Example 16

Methods for Separating and Quantifying TAG from Leaf Lipids

In addition to TLC according to Example 2 followed by GC-FID other methods were used to separate lipid classes and quantify TAG. These methods include use of Solid Phase Extraction (SPE) followed by quantitative gas chromatography and high performance liquid chromatography equipped with an evaporative light scattering detector (HPLC-ELSD). Sample collection and lipid extraction methods were modified to enable sample collection and analysis in a 96-well plate format. Approximately 10 mg leaf tissue was sampled into pre-weighed 1.2 ml polypropylene tubes. The tissue was lyophilized and the exact dry weight was obtained. Four monophasic extractions of 100% hexane were used to extract the neutral lipids from lyophilized leaf discs, and were pooled in a clean 96-well plate. For the SPE method, an internal standard, 0.02 mg tri-C17 TAG, was added prior to extraction of neutral lipids. TAG was isolated by SPE using 96-well aminopropyl SPE plates (Thermo). Columns were preconditioned with 1 mL of hexane prior to loading samples as a 0.5 mL hexane fraction. Columns were washed with 1 mL of hexane:dichloromethane: chloroform (88:10:4 v/v), then TAG was eluted with 1 mL of Hexane: ethyl acetate (96:4 v/v). The TAG fraction was concentrated and resuspended in 180 μl heptane. Fatty acids were derivatized by the addition of 20 μl of approximately 0.25 M trimethylsulfonium hydroxide in methanol (Sigma-Aldrich) was added, followed by GC-FID for quantification. For the HPLC-ELSD procedure, the hexane-extracted lipids were filtered through a PTFE 0.2 μm filter plate. Samples were then dried down and resuspended in 80 μL of heptane. A cyanopropyl column (Luna 5 μM CN 100 Å 250×4.6 mm; Phenomenx) was used to separate lipid species on an HPLC-ELSD with hexane as mobile phase A and methyl tertiary-butyl ether (MTBE):isopropanol (95:5 v/v) plus 0.2% acetic acid as mobile phase B, with a gradient of 0% to 100% B, with re-equilibration of the column to 0% B. A standard curve of tri-C17 TAG was run with each sample set to quantify TAG as Oil Content (% of DW).

TAG quantification procedures including TLC/GC-FID procedure of Example 2 were compared by transiently expressing empty vector (EV), GmDGAT1b WT (SEQ ID NO:2), and GmDGAT1b mod (SEQ ID NO:27) in tobacco leaf. The oil content values are shown in (FIG. 7). The SPE and HPLC procedures were found to effectively quantify TAG in the leaves and modified leaves disclosed herein and enabled high-throughput analysis of TAG accumulation.

Example 17

Additional Single to Quadruple Amino Acid Changes in DGAT Increase Oil Content in Tobacco Leaf Assay Additional GmDGAT1b variants were tested in the tobacco leaf assay and directly compared using the SPE/GC-FID and HPLC-ELSD procedures. Similar trends were observed between the two procedures for any of the samples tested (FIG. 8). Single amino acid substitution variants GmDGAT1b S264T and GmDGAT1b N473S significantly increased oil content in tobacco leaves compared to GmDGAT1b WT (FIG. 8). Using the SPE/GC-FID procedure, single amino acid substitution GmDGAT1b variant S264T, double variants C355S I479S and D258E I479S, triple variant C355S N473S I479S, and quadruple variant T216V D258E S264T I479S all had significant increases in oil content compared to the WT (FIG. 9). The triple GmDGAT1b variant C355S N473S I479S had comparable oil content as GmDGAT1b mod, with 14 amino acid substitutions, and N473S almost reached GmDGAT1b mod oil content levels (FIG. 9). This triple amino acid substitution DmDGAT1b variant C355S N473S I479S also had a significantly increased oil/protein ratio (FIG. 10), suggesting that this variant may have improved DGAT activity. These results show that 1-4 amino acid substitutions are sufficient to improve GmDGAT1b WT in planta.

---

What is claimed is:

1. A modified polynucleotide encoding a diacylglycerol acyltransferase-1 (DGAT1) polypeptide having at least 95% identity to SEQ ID NO:2, the polynucleotide encoding a modification comprising a non-asparagine at the position corresponding to position 473 of SEQ ID NO:2, wherein when expressed in a plant cell, the polynucleotide increases the fatty acid content of the plant cell compared to a plant cell comprising a comparable polynucleotide without the modification.

2. The modified polynucleotide of claim 1, wherein the polypeptide encoded by the modified polynucleotide has at least 98% identity to SEQ ID NO:2.

3. The modified polynucleotide of claim 1, wherein the polynucleotide encodes a serine at the position corresponding to position 473 of SEQ ID NO: 2.

4. The modified polynucleotide of claim 1, wherein the polynucleotide comprises a further modification encoding a non-cysteine at the position corresponding to position 355 of SEQ ID NO: 2.

5. The modified polynucleotide of claim 4, wherein the further modification encodes a serine at the position corresponding to position 355 of SEQ ID NO:2.

6. The modified polynucleotide of claim 1, wherein the polynucleotide further comprises a modification encoding a non-isoleucine at the position corresponding to position 479 of SEQ ID NO: 2.

7. The modified polynucleotide of claim 6, wherein the further modification encodes a serine at the position corresponding to position 479 of SEQ ID NO: 2.

8. The modified polynucleotide of claim 1, wherein the polypeptide further comprises a deletion of at least 1 and less than 107 amino acids corresponding to the region at positions 1 to 107 of SEQ ID NO: 2, wherein the DGAT1 polypeptide has increased stability when expressed in a plant cell.

9. The modified polynucleotide of claim 1, wherein the DGAT1 further comprises (i) at least one amino acid motif selected from the group consisting of APTLCYQ (SEQ ID NO: 38), FGDREFYXDWWNA (SEQ ID NO: 39) and LLYYHD (SEQ ID NO: 40), where X is any amino acid; (ii) at least one amino acid motif selected from the group consisting of APTLCYQ (SEQ ID NO: 38), FGDREFYXDWWNA (SEQ ID NO: 39) and LLYYHD (SEQ ID NO: 40), where X is K or Q; or (iii) at least one amino acid motif selected from the group consisting of ESPLSSDX'IFX'QSHAGLX'NLCX'WLX'AVNX'R-LIIENLMKYGX'LI (SEQ ID NO: 41) and GFIIEQYIN-PIVX'NSX'HPL (SEQ ID NO: 42), wherein X' is any amino acid.

10. A plant cell comprising the modified polynucleotide of claim 1.

11. A soybean seed comprising the cell of claim 10, wherein the soybean seed has an increased oil content compared to a seed comprising the comparable polynucleotide without the modification.

12. The soybean seed of claim 11, wherein the oil content is increased by at least 5%.

13. A plant cell comprising the modified polynucleotide of claim 3.

14. A soybean seed comprising the cell of claim 13, wherein the soybean seed has an increased oil content compared to a seed comprising the comparable polynucleotide without the modification.

15. The soybean seed of claim 14, wherein the oil content is increased by at least 5%.

16. A plant cell comprising the modified polynucleotide of claim 6.

17. A soybean seed comprising the cell of claim 16, wherein the soybean seed has an increased oil content compared to a seed comprising the comparable polynucleotide without the modification.

18. The soybean seed of claim 17, wherein the oil content is increased by at least 5%.

19. A polypeptide encoded by the polynucleotide of claim 1.

20. A method for increasing the oil content of a soybean cell comprising a polynucleotide encoding a DGAT1 polypeptide, the method comprising
   a. inducing a break in the genome of the soybean cell and repairing the break, wherein the repair of the break results in at least one nucleotide substitution in the polynucleotide, the substitution encoding a non-asparagine at the position corresponding to position 473 of SEQ ID NO:2, to produce a modified polynucleotide encoding a modified polypeptide;
   b. expressing the modified polypeptide in the soybean cell using an endogenous promoter of the polynucleotide, wherein the fatty acid content of the soybean cell is increased compared to a soybean cell expressing a comparable polypeptide without the substitutions.

* * * * *